(12) United States Patent
Swanson et al.

(10) Patent No.: US 12,031,970 B2
(45) Date of Patent: Jul. 9, 2024

(54) AGRICULTURAL SAMPLING SYSTEM AND RELATED METHODS

(71) Applicant: Precision Planting LLC, Tremont, IL (US)

(72) Inventors: Todd Swanson, Morton, IL (US); Timothy A. Schaefer, Tremont, IL (US); Riley Litwiller, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 452 days.

(21) Appl. No.: 17/343,536

(22) Filed: Jun. 9, 2021

(65) Prior Publication Data

US 2021/0341452 A1 Nov. 4, 2021

Related U.S. Application Data

(63) Continuation-in-part of application No. PCT/IB2021/052876, filed on Apr. 7, 2021, and a
(Continued)

(51) Int. Cl.
*G01N 33/24* (2006.01)
*A01B 79/00* (2006.01)
(Continued)

(52) U.S. Cl.
CPC ........... *G01N 33/24* (2013.01); *A01B 79/005* (2013.01); *B01L 3/50273* (2013.01);
(Continued)

(58) Field of Classification Search
CPC .............. G01N 33/24; G01N 2033/245; A01B 79/005; B01L 3/50273; B01L 3/502738;
(Continued)

(56) References Cited

U.S. PATENT DOCUMENTS 3,338,171 A 8/1967 Conklin et al.
3,363,769 A 1/1968 Wilmot et al.
(Continued)

FOREIGN PATENT DOCUMENTS

CA 2147726 A1 10/1995
CN 204900224 U 12/2015
(Continued)

OTHER PUBLICATIONS

UK Intellectual Property Office, Search Report prepared for related Application No. GB2007213.8, dated Sep. 23, 2020.
(Continued)

*Primary Examiner* — Jonathan M Dunlap

(57) ABSTRACT

An automated computer-controlled sampling system and related methods for collecting, processing, and analyzing agricultural samples for various chemical properties such as plant available nutrients. The sampling system allows multiple samples to be processed and analyzed for different analytes or chemical properties in a simultaneous concurrent or semi-concurrent manner. Advantageously, the system can process soil samples in the "as collected" condition without drying or grinding to produce a sample slurry. The system includes a chemical analysis sub-system which processes and analyzes the prepared slurry for quantifying multiple analytes and/or chemical properties of the sample. The chemical analysis sub-system may be embodied in a multi-layered microfluidic manifold processing substrate comprising microfluidic devices which extract and quantify the concentration of analytes or other chemical parameters associated with the sample. The system can be used to analyze various type of agricultural-related samples including soil, vegetation, manure, milk or other.

19 Claims, 41 Drawing Sheets

Related U.S. Application Data continuation-in-part of application No. PCT/IB2021/052875, filed on Apr. 7, 2021, and a continuation-in-part of application No. PCT/IB2021/052874, filed on Apr. 7, 2021, and a continuation-in-part of application No. PCT/IB2021/052872, filed on Apr. 7, 2021.

(60) Provisional application No. 63/018,153, filed on Apr. 30, 2020, provisional application No. 63/017,789, filed on Apr. 30, 2020, provisional application No. 63/017,840, filed on Apr. 30, 2020, provisional application No. 63/018,120, filed on Apr. 30, 2020.

(51) Int. Cl.
| | |
|---|---|
| *B01L 3/00* | (2006.01) |
| *F04B 13/02* | (2006.01) |
| *F04B 19/00* | (2006.01) |
| *F04B 43/073* | (2006.01) |
| *F16K 99/00* | (2006.01) |

(52) U.S. Cl.
CPC ...... *B01L 3/502738* (2013.01); *F04B 19/006* (2013.01); *B01L 2200/0605* (2013.01); *B01L 2300/0816* (2013.01); *B01L 2300/0877* (2013.01); *B01L 2300/0883* (2013.01); *B01L 2300/0887* (2013.01); *F04B 13/02* (2013.01); *F04B 43/073* (2013.01); *F16K 99/0015* (2013.01); *F16K 99/0059* (2013.01); *F16K 2099/0084* (2013.01); *G01N 2033/245* (2013.01)

(58) Field of Classification Search
CPC ..... B01L 2300/0816; B01L 2300/0877; B01L 2300/0883; B01L 2300/0887; B01L 2200/0605; F01B 19/006; F16K 2099/0084; F16K 99/0015; F16K 99/0059; F04B 13/02; F04B 43/073
See application file for complete search history.

(56) References Cited

U.S. PATENT DOCUMENTS

| | | | |
|---|---|---|---|
| 3,583,209 A | 6/1971 | Banks | |
| 3,605,815 A | 9/1971 | Von Forell | |
| 3,625,296 A | 12/1971 | Mabry et al. | |
| 3,874,417 A | 4/1975 | Clay | |
| 4,074,562 A | 2/1978 | North, Jr. | |
| 4,123,204 A | 10/1978 | Scholle | |
| 4,163,461 A | 8/1979 | Jacobellis | |
| 4,243,533 A | 1/1981 | Savolainen et al. | |
| 4,727,758 A | 3/1988 | Murdock | |
| 4,981,418 A | 1/1991 | Kingsford et al. | |
| 5,033,319 A | 7/1991 | Ireland | |
| 5,186,615 A | 2/1993 | Karliner | |
| 5,332,372 A | 7/1994 | Reynolds | |
| 5,526,705 A | 6/1996 | Skotnikov et al. | |
| 5,863,443 A | 1/1999 | Mainwaring | |
| 5,932,799 A | 8/1999 | Moles | |
| 7,401,543 B2 | 7/2008 | Curtis | |
| 8,325,336 B2 | 12/2012 | Preiner et al. | |
| 8,822,230 B2 | 9/2014 | Miyoshi et al. | |
| 9,028,224 B2 | 5/2015 | Headley et al. | |
| 9,044,752 B2 | 6/2015 | Wimberger-Friedl et al. | |
| 9,116,078 B1 | 8/2015 | Scheiderer et al. | |
| 9,383,232 B2 | 7/2016 | Hoshika et al. | |
| 9,891,155 B2 | 2/2018 | Eising | |
| 10,065,186 B2 | 9/2018 | Kolb et al. | |
| 10,870,113 B1* | 12/2020 | Gentalen | G01N 27/44791 |
| 11,529,579 B2 | 12/2022 | Kawaguchi et al. | |
| 11,549,871 B2 | 1/2023 | Sogaard et al. | |
| 2005/0255004 A1* | 11/2005 | Yao | B01L 3/50273 422/503 |
| 2006/0219642 A1 | 10/2006 | Farnham et al. | |
| 2007/0017277 A1 | 1/2007 | Francisco, Jr. et al. | |
| 2008/0053221 A1 | 3/2008 | Allen | |
| 2008/0262783 A1 | 10/2008 | Alexander Lambert | |
| 2010/0224256 A1 | 9/2010 | Tseng et al. | |
| 2010/0303687 A1 | 12/2010 | Blaga et al. | |
| 2012/0051390 A1 | 3/2012 | Coursey et al. | |
| 2012/0103077 A1 | 5/2012 | Koshnick et al. | |
| 2012/0132597 A1 | 5/2012 | Byalskiy et al. | |
| 2012/0177543 A1 | 7/2012 | Battrell et al. | |
| 2013/0078125 A1 | 3/2013 | Headley et al. | |
| 2013/0284651 A1 | 10/2013 | Lin et al. | |
| 2015/0041380 A1 | 2/2015 | Lin et al. | |
| 2015/0109877 A1 | 4/2015 | Multner et al. | |
| 2015/0151223 A1 | 6/2015 | Eckman | |
| 2015/0160056 A1 | 6/2015 | Schollenberger et al. | |
| 2016/0252914 A1 | 9/2016 | Padgett et al. | |
| 2016/0361715 A1 | 12/2016 | Shi et al. | |
| 2017/0241929 A1 | 8/2017 | Qui et al. | |
| 2018/0008945 A1 | 1/2018 | Bergamini | |
| 2018/0124992 A1 | 5/2018 | Koch et al. | |
| 2018/0224419 A1 | 8/2018 | Gerber-Siff et al. | |
| 2019/0120737 A1 | 4/2019 | White et al. | |
| 2019/0176149 A1 | 6/2019 | Shachar et al. | |
| 2021/0048424 A1 | 2/2021 | Koshnick et al. | |
| 2021/0123936 A1 | 4/2021 | Swanson et al. | |
| 2021/0208037 A1 | 7/2021 | Swanson et al. | |
| 2021/0208123 A1 | 7/2021 | Swanson et al. | |
| 2021/0269331 A1 | 9/2021 | Anderson et al. | |
| 2021/0341452 A1 | 11/2021 | Swanson et al. | |
| 2022/0072545 A1 | 3/2022 | Keller et al. | |
| 2022/0364998 A1 | 11/2022 | Koch et al. | |
| 2023/0213495 A1 | 7/2023 | Pluta | |

FOREIGN PATENT DOCUMENTS

| | | | | |
|---|---|---|---|---|
| CN | 107413269 A | 12/2017 | | |
| CN | 110987560 A | 4/2020 | | |
| DE | 2936145 B1 | 10/1980 | | |
| DE | 2931049 A1 | 2/1981 | | |
| DE | 202010002930 U | 9/2011 | | |
| EP | 0525815 A1 | 2/1993 | | |
| EP | 0570335 A1 | 11/1993 | | |
| EP | 3636602 A1 | 4/2020 | | |
| GB | 751895 A | 7/1956 | | |
| GB | 850518 A | 10/1960 | | |
| GB | 2555816 A | 5/2018 | | |
| JP | S6293501 A | 4/1987 | | |
| JP | H02191511 A | 7/1990 | | |
| JP | H05317672 A | 12/1993 | | |
| JP | 2003210912 A | 7/2003 | | |
| JP | 2007029848 A | 2/2007 | | |
| WO | 2000069547 A1 | 11/2000 | | |
| WO | 2005/089389 A | 9/2005 | | |
| WO | 2006043900 A1 | 4/2006 | | |
| WO | WO-2012051218 A2 * | 4/2012 | ........ | B01L 3/502715 |
| WO | 2013098487 A1 | 7/2013 | | |
| WO | 2015/175470 A1 | 11/2015 | | |
| WO | 2015171908 A1 | 11/2015 | | |
| WO | WO-2019196850 A1 * | 10/2019 | ......... | F16K 99/0003 |
| WO | 2020/012369 A2 | 1/2020 | | |
| WO | 2021074722 A1 | 4/2021 | | |
| WO | 2021171120 A1 | 9/2021 | | |
| WO | 2021171121 A1 | 9/2021 | | |
| WO | 2021220082 A1 | 11/2021 | | |
| WO | 2021220083 A1 | 11/2021 | | |
| WO | 2021220084 A1 | 11/2021 | | |
| WO | 2021220085 A1 | 11/2021 | | |
| WO | 2022243792 A1 | 11/2022 | | |
| WO | 2022243793 A1 | 11/2022 | | |
| WO | 2022243794 A1 | 11/2022 | | |
| WO | 2022243795 A1 | 11/2022 | | |
| WO | 2022243796 A1 | 11/2022 | | |
| WO | 2022243797 A1 | 11/2022 | | |
| WO | 2022243806 A1 | 11/2022 | | |
| WO | 2022243807 A1 | 11/2022 | | |
| WO | 2022243808 A1 | 11/2022 | | |
| WO | 2022243809 A1 | 11/2022 | | |
| WO | 2022259071 A1 | 12/2022 | | |

(56) References Cited

FOREIGN PATENT DOCUMENTS

| WO | 2022259073 A1 | 12/2022 |
|---|---|---|
| WO | 2022259074 A1 | 12/2022 |
| WO | 2022269388 A1 | 12/2022 |
| WO | 2023031725 A1 | 3/2023 |
| WO | 2023031726 A1 | 3/2023 |
| WO | 2023031727 A1 | 3/2023 |
| WO | 2023042036 A1 | 3/2023 |
| WO | 2023042037 A1 | 3/2023 |
| WO | 2023042038 A1 | 3/2023 |
| WO | 2023042039 A1 | 3/2023 |
| WO | 2023161727 A1 | 8/2023 |
| WO | 2023161728 A1 | 8/2023 |

OTHER PUBLICATIONS

UK Intellectual Property Office, Search Report prepared for related Application No. GB2007439.9, dated Nov. 18, 2020.
UK Intellectual Property Office, Search Report prepared for related Application No. GB2007210.4, dated Oct. 29, 2020.
European Patent Office, Search report for related PCT Application No. PCT/IB2022/054921, dated Sep. 6, 2022, 10 pages.
Provolo et al: "In situ determination of slurry nutrient content by electrical conductivity", Bioresource Technology, Elsevier, Amsterdam, NL, vol. 98, No. 17, Aug. 23, 2007, pp. 3235-3242, ISSN: 0960-8524, DOI: 10.1016/J.BIORTECH.2006.07.018.
Iain R. G. Ogilvie, "Novel fabrication techniques for microfluidic based in-situ oceanographic nutrient sensors", Sep. 1, 2012, 2012.

* cited by examiner

AGRICULTURAL SAMPLING SYSTEM AND RELATED METHODS

CROSS REFERENCE TO RELATED APPLICATIONS

This application is a continuation in part of International Application Nos. PCT/IB2021/052872, filed 7 Apr. 2021; PCT/IB2021/052874, filed 7 Apr. 2021; PCT/IB2021/052875, filed 7 Apr. 2021; and PCT/IB2021/052876, filed 7 Apr. 2021 each of which claim priority to U.S. Provisional Application Nos. 63/017,789, filed 30 Apr. 2020; 63/017,840, filed 30 Apr. 2020; 63/018,120, filed 30 Apr. 2020; and 63/018,153, filed 30 Apr. 2020, the disclosure of all of the preceding applications are incorporated herein by reference in their entireties.

BACKGROUND

The present invention relates generally to agricultural sampling and analysis, and more particularly to a fully automated system for performing soil and other types of agricultural related sampling and chemical property analysis.

Periodic soil testing is an important aspect of the agricultural arts. Test results provide valuable information on the chemical makeup of the soil such as plant-available nutrients and other important properties (e.g. levels of nitrogen, magnesium, phosphorous, potassium, pH, etc.) so that various amendments may be added to the soil to maximize the quality and quantity of crop production.

In some existing soil sampling processes, collected samples are dried, ground, water is added, and then filtered to obtain a soil slurry suitable for analysis. Extractant is added to the slurry to pull out plant available nutrients. The slurry is then filtered to produce a clear solution or supernatant which is mixed with a chemical reagent for further analysis.

Improvements in testing soil, vegetation, and manure are desired.

BRIEF SUMMARY

The present invention provides an automated computer-controlled sampling system and related methods for collecting, processing, and analyzing soil samples for various chemical properties such as plant available nutrients (hereafter referred to as a "soil sampling system"). The sampling system allows multiple samples to be processed and analyzed for different analytes (e.g. plant-available nutrients) and/or chemical properties (e.g. pH) in a simultaneous concurrent or semi-concurrent manner, and in relatively continuous and rapid succession. Advantageously, the system can process soil samples in the "as collected" condition without the drying and grinding steps previously described.

The present system generally includes a sample preparation sub-system which receives soil samples collected by a probe collection sub-system and produces a slurry (i.e. mixture of soil, vegetation, and/or manure and water) for further processing and chemical analysis, and a chemical analysis sub-system which receives and processes the prepared slurry samples from the sample preparation sub-system for quantification of the analytes and/or chemical properties of the sample. The described chemical analysis sub-system can be used to analyze soil, vegetation, and/or manure samples.

In one embodiment, the sample preparation system generally includes a mixer-filter apparatus which mixes the collected raw soil sample in the "as sampled" condition (e.g. undried and unground) with water to form a sample slurry. The mixer-filter apparatus then filters the slurry during its extraction from the apparatus for processing in the chemical analysis sub-system. The filter may be separate The chemical analysis sub-system processes the slurry and performs the general functions of extractant and color-changing reagent addition/mixing, centrifugating or filtering the slurry sample via microporous filter to yield a clear supernatant, and finally sensing or analysis for detection of the analytes and/or chemical properties such as via colorimetric analysis. In various embodiments, all or part of the chemical analysis sub-system may be incorporated into one or more microfluidic devices of suitable configuration.

Although the sampling systems (e.g. sample collection, preparation, and processing) may be described herein with respect to processing soil samples which represents one category of use for the disclosed embodiments, it is to be understood that the same systems including the apparatuses and related processes may further be used for processing other types of agricultural related samples including without limitation vegetation/plant, forage, manure, feed, milk, or other types of samples. The embodiments of the invention disclosed herein should therefore be considered broadly as an agricultural sampling system. Accordingly, the present invention is expressly not limited to use with processing and analyzing soil samples alone for chemical properties of interest.

BRIEF DESCRIPTION OF THE DRAWINGS

The present invention will become more fully understood from the detailed description and the accompanying drawings, wherein like elements are labeled similarly and in which.

Figure 1:
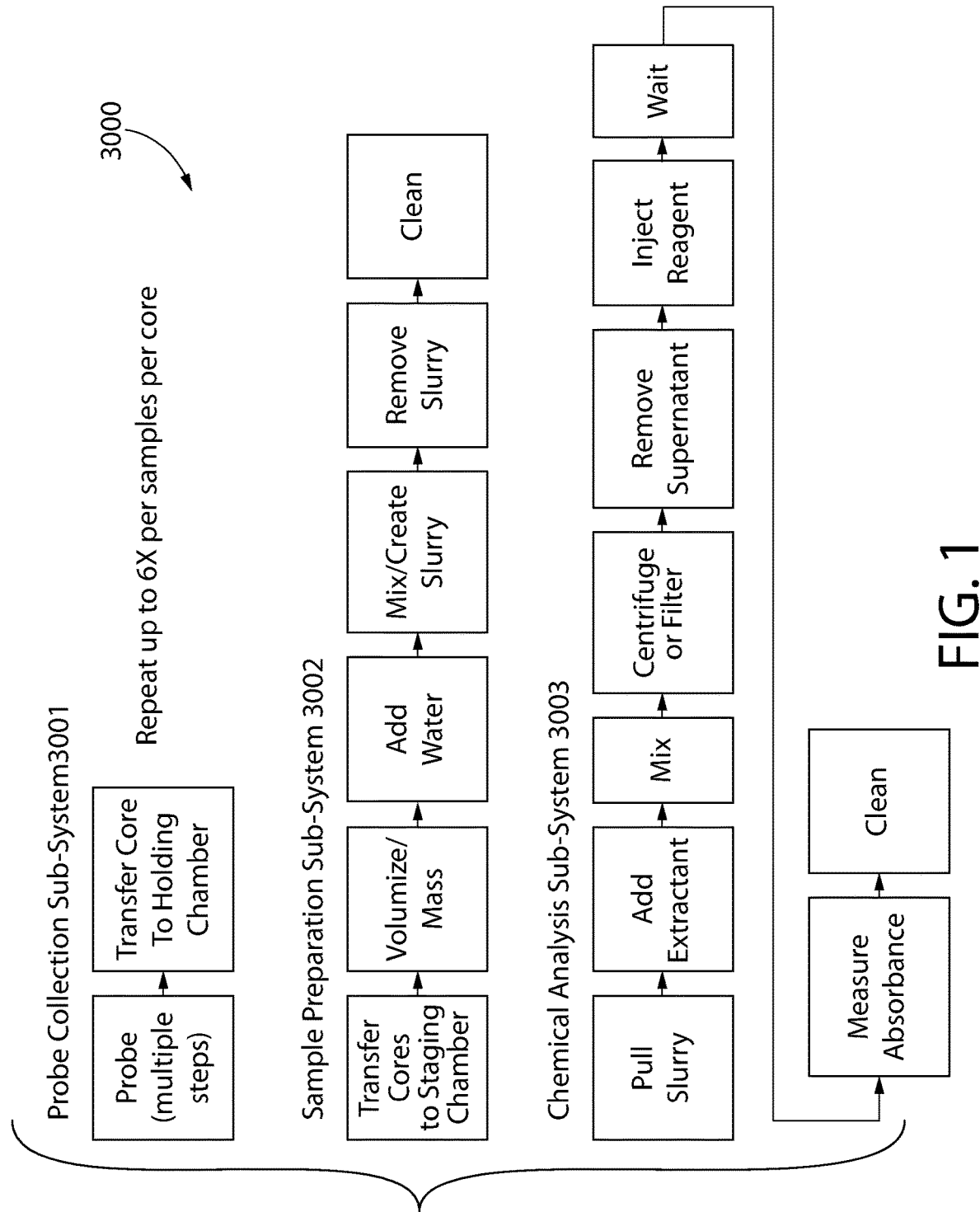
FIG. 1 is a schematic flow diagram of an agricultural sampling analysis system according to the present disclosure showing high-level functional aspects of each sub-system of the sampling analysis system.

All drawings are not necessarily to scale. Components numbered and appearing in one figure but appearing un-numbered in other figures are the same unless expressly noted otherwise. A reference herein to a figure by a whole figure number which appears in multiple figures bearing the same whole number but with different alphabetical suffixes shall be construed as a general reference to all of those figures unless expressly noted otherwise.

DETAILED DESCRIPTION

The features and benefits of the invention are illustrated and described herein by reference to exemplary ("example") embodiments. This description of exemplary embodiments is intended to be read in connection with the accompanying drawings, which are to be considered part of the entire written description. Accordingly, the disclosure expressly should not be limited to such exemplary embodiments illustrating some possible non-limiting combination of features that may exist alone or in other combinations of features.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

As used throughout, any ranges disclosed herein are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

FIG. 1 is a high level schematic diagram flow chart describing the functional aspects of an agricultural sampling system 3000 according to the present disclosure. The system includes multiple sub-systems which operate in concert and sequence. The sub-systems disclosed herein collectively provide complete processing and chemical analysis of soil samples from collection in the agricultural field, sample preparation and processing, and final chemical analysis. The agricultural material sampled may be soil in one embodiment; however, other types of agricultural materials may be processed and analyzed in the same system including without limitation vegetation/plants, crop residues, forage, manure, feed, milk, and other agricultural related materials of interest in the agricultural, livestock, diary or similar arts. In the context of soil sampling for example which is important to crop production and yield, the agricultural sampling system 3000 advantageously allows multiple samples to be processed and chemically analyzed simultaneously for different various plant-available nutrients or other parameters such as for example without limitation pH, BpH (buffer pH), etc. This information may be used to generate nutrient/parameter maps for the agricultural field to determine the appropriate quantities of soil amendments needed in different regions of the field to maximize overall crop production.

In one embodiment, portions of the agricultural sampling system 3000 may be incorporated onboard a motorized sampling vehicle configured to traverse an agricultural field for collecting and processing soil samples from various zones of the field. This allows a comprehensive nutrient and chemical profile of the field to be accurately generated "on-the-fly" in order to quickly and conveniently identify the needed soil amendments and application amounts necessary in real-time for each zone or region of the field based on quantification of the plant-available nutrient and/or chemical properties in the sample.

The soil sampling system 3000 generally includes a sample probe collection sub-system 3001, a sample preparation sub-system 3002, and a chemical analysis sub-system 3003. The sample collection sub-system 3001 and motorized sampling vehicle are fully described in U.S. Patent Application Publication No. 2018/0124992A1. Sample collection sub-system 3001 generally performs the function of extracting and collecting soil samples from the field. The samples may be in the form of soil plugs or cores. The collected cores are transferred to a holding chamber or vessel for further processing by the sample preparation sub-system 3002. Other sampling systems are described in U.S. Application Nos. 62/983,237, filed on 28 Feb. 2020; 63/017,789, filed on 30 Apr. 2020; 63/017,840, filed on 30 Apr. 2020; 63/018,120, filed on 30 Apr. 2020; 63/018,153, filed on 30 Apr. 2020; PCT/IB2021/051076, filed on 10 Feb. 2021; and PCT Application Nos. PCT/IB2021/051077, filed on 10 Feb. 2021; PCT/IB2021/052872, filed on 7 Apr. 2021; PCT/IB2021/052874, filed on 7 Apr. 2021; PCT/IB2021/052875, filed on 7 Apr. 2021; PCT/IB2021/052876, filed on 7 Apr. 2021.

The sample preparation sub-system 3002 generally performs the functions of receiving the soil sample cores in a mixer-filter apparatus, volumetric/mass quantification of the soil sample, adding a predetermined quantity or volume of filtered water based on the volume/mass of soil, and mixing the soil and water mixture to produce a soil sample slurry, removing or transferring the slurry from mixer-filter apparatus, and self-cleaning the mixer-filter apparatus for processing the next available soil sample. In some embodiments, the filter may be separate from the mixer.

The chemical analysis sub-system 3003 generally performs the functions of receiving the soil slurry from a mixer-filter apparatus of sub-system 3002, adding extractant, mixing the extractant and slurry in a first chamber to pull out the analytes of interest (e.g. plant available nutrients), centrifuging the extractant-slurry mixture to produce a clear liquid or supernatant, removing or transferring the supernatant to a second chamber, injecting a reagent, holding the supernatant-reagent mixture for a period of hold time to allow complete chemical reaction with reagent, measure the absorbance such as via colorimetric analysis, and assist with cleaning the chemical analysis equipment. In some embodiments, the chemical analysis sub-system 3003 may be embodied in a microfluidic device or apparatus, as further described herein.

Figure 4:
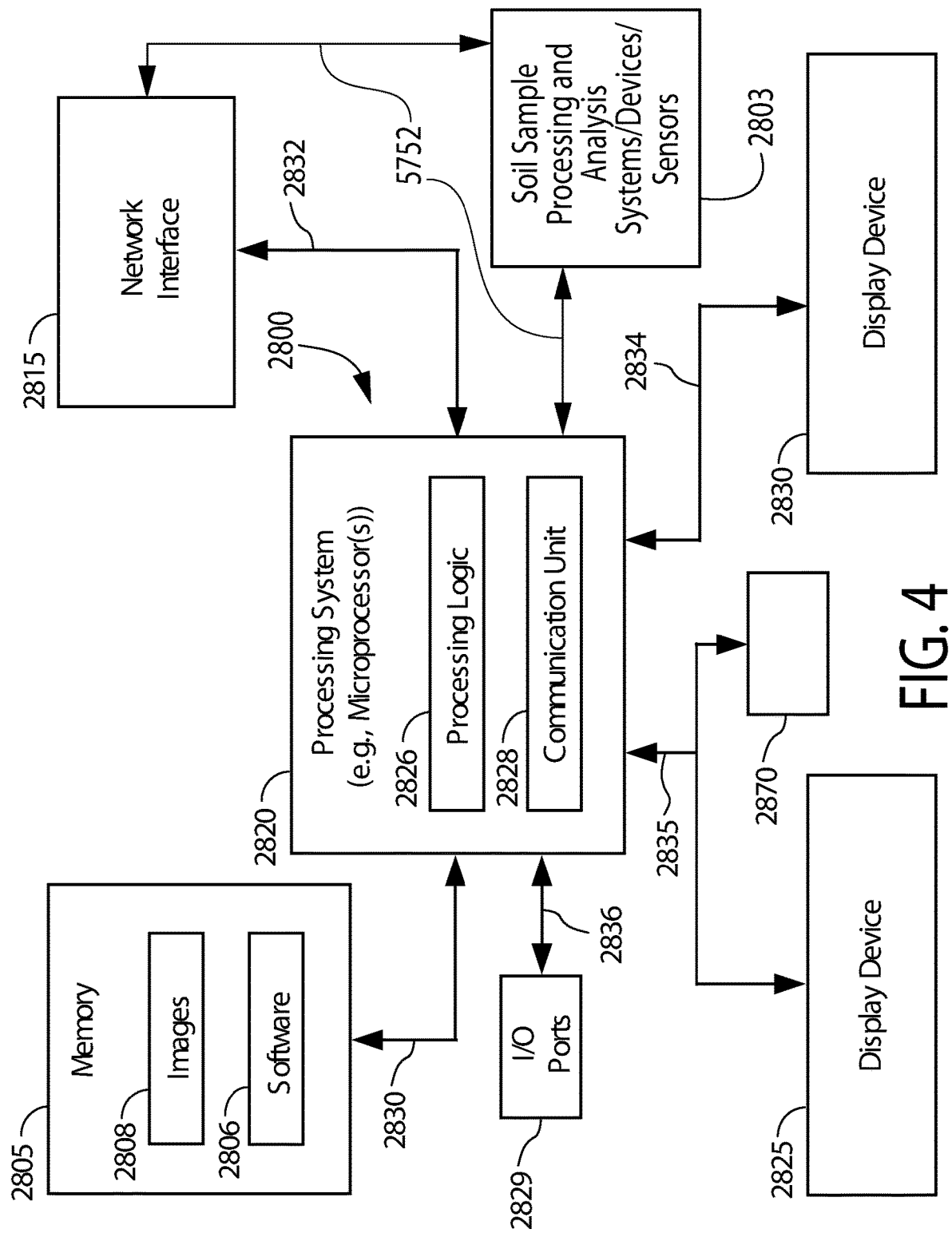
FIG. 4 is a schematic system diagram of a programmable processor-based central processing unit (CPU) or system controller configured and operable for controlling the microfluidic devices of the microfluidic processing manifold systems and apparatuses disclosed herein.
Figure 5:
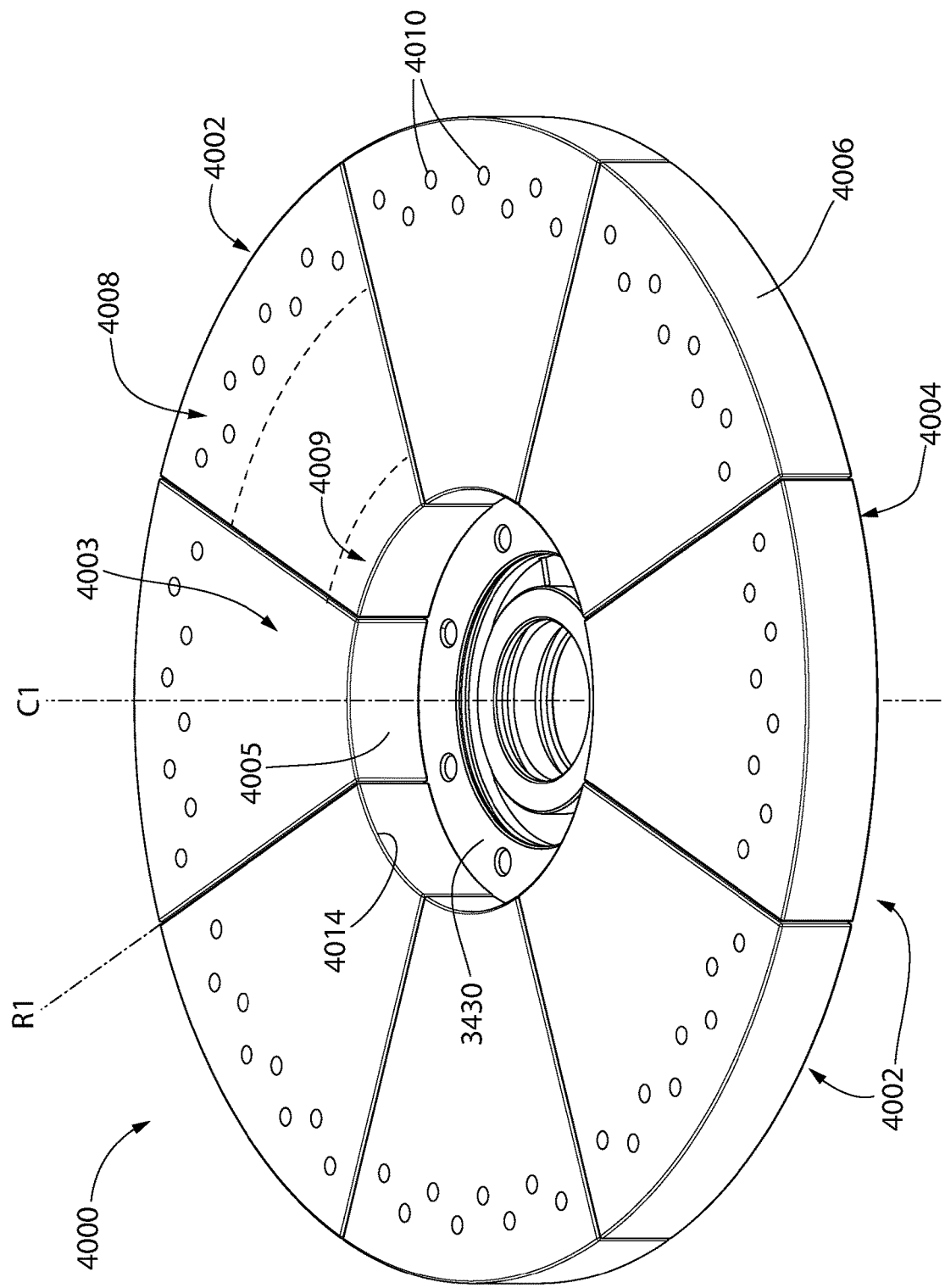
FIG. 5 is a top perspective view of a microfluidic processing disk with plurality of chemical analysis processing wedges each configured as a stand alone processing training for performing complete soil slurry processing and chemical analysis.
Figure 6:
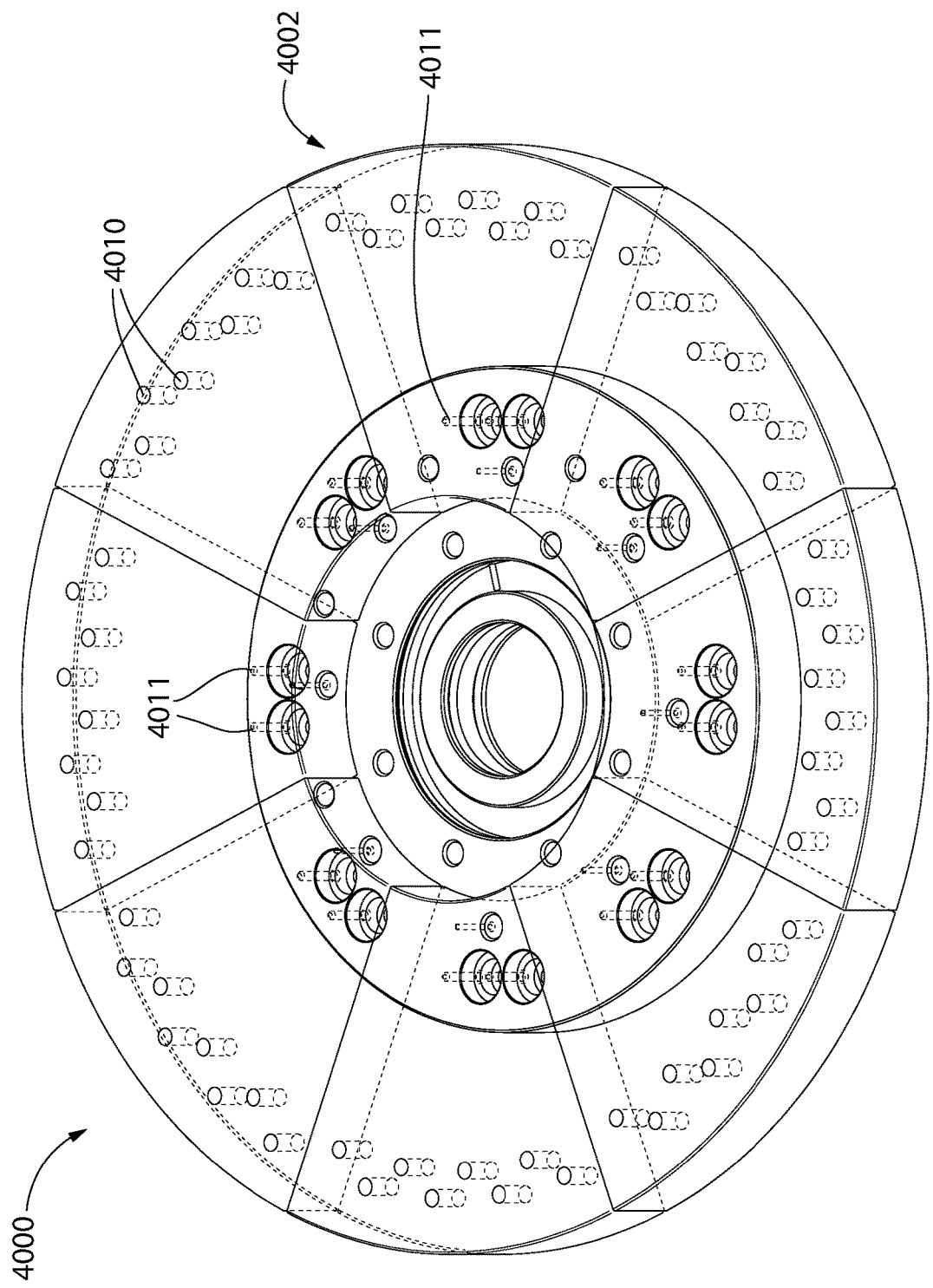
FIG. 6 is a bottom perspective view thereof.
Figure 7:
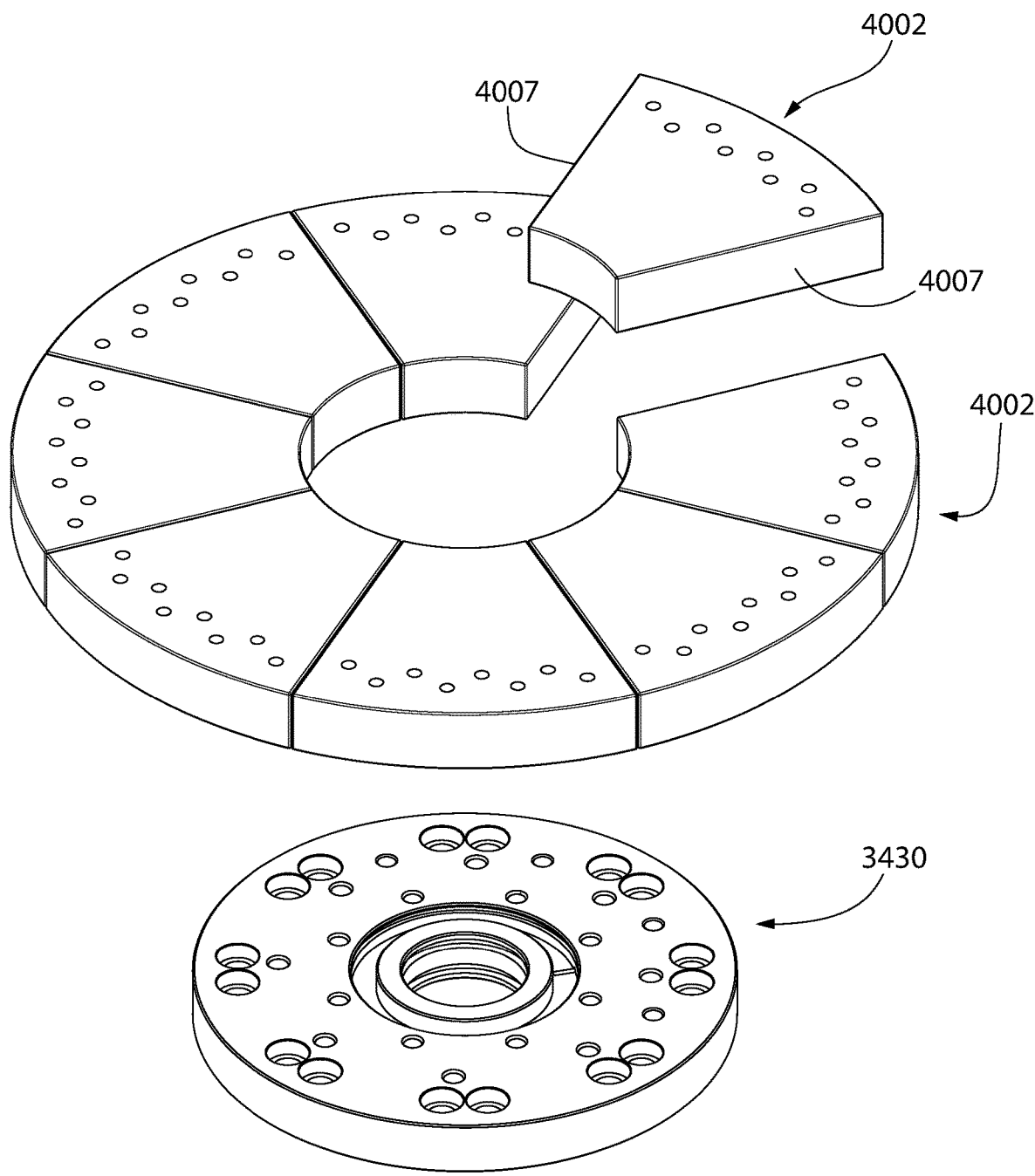
FIG. 7 is a partially exploded perspective view thereof with fluid exchange dock which fluidly couples to the microfluidic processing disk shown below.
Figure 8:
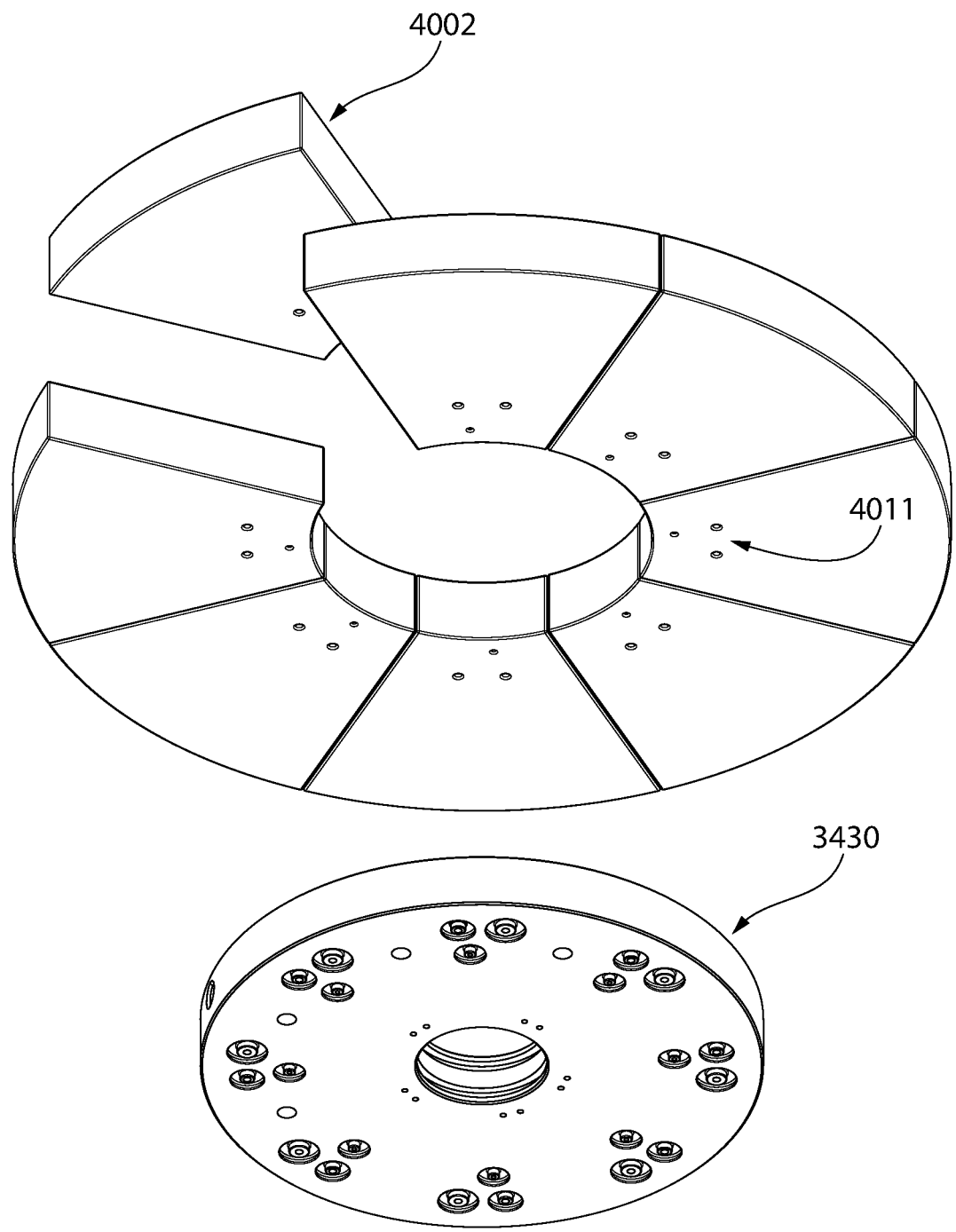
FIG. 8 is a bottom perspective view thereof.
Figure 9:
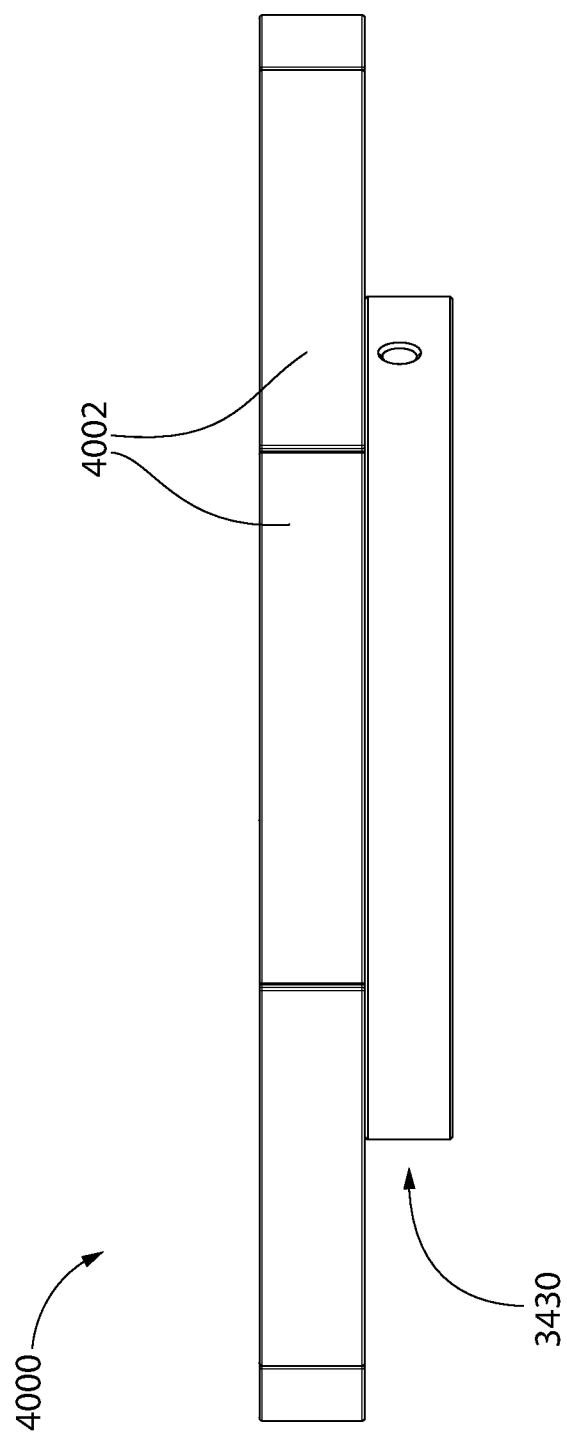
FIG. 9 is a side view of the microfluidic processing disk.
Figure 10:
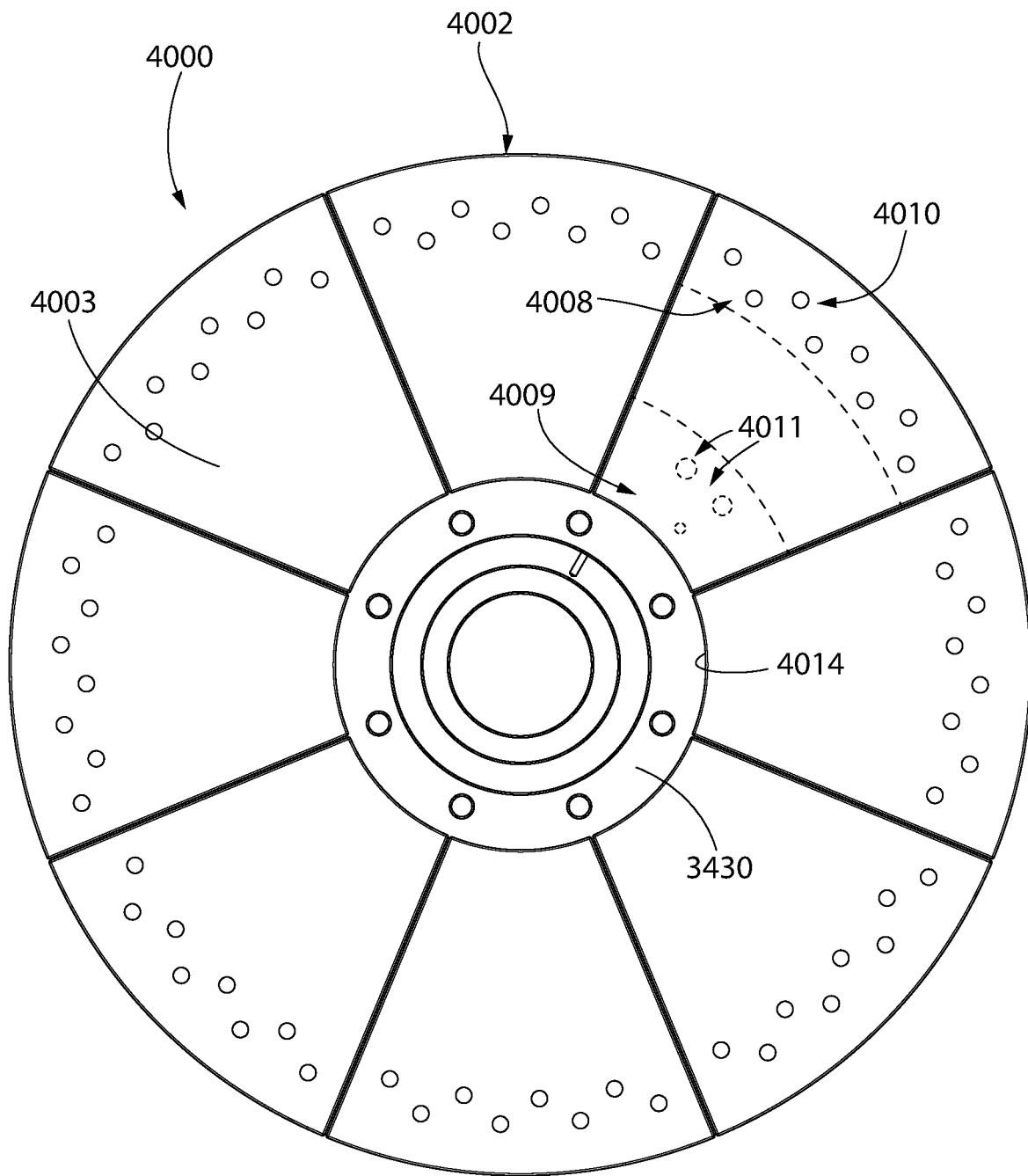
FIG. 10 is a top view thereof.
Figure 11:
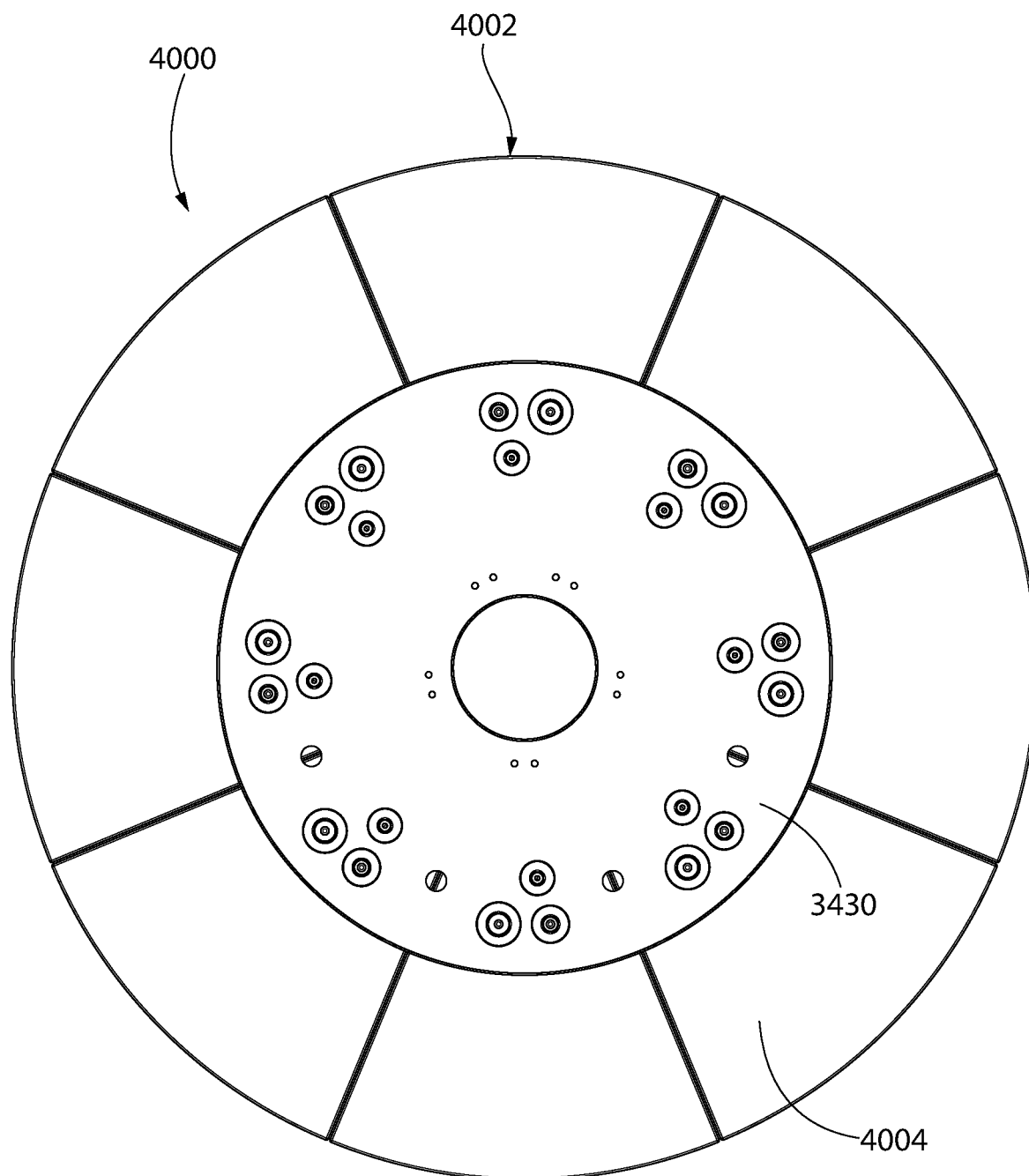
FIG. 11 is a bottom view thereof.

The process described below and in the flow diagrams may be automatically controlled and executed by the programmable system controller 2820. The controller may be part of a controller processing system such as that further described herein and shown in FIG. 4, or as disclosed in copending U.S. Patent Application Publication No. 2018/0124992A1. The controller 2820 is operably coupled to the components of the chemical analysis sub-system 3003 disclosed herein (e.g., pumps, valves, centrifuge, compressor (air supply), etc.) for controlling the process sequence and flow of fluids (e.g., water, air, slurry, extractant, reagent, supernatant, etc.) through the system to fully process and analyze the soil or other type agricultural sample. FIG. 4 depicts one embodiment of a programmable system controller 2820 applicable to the present application.

Supernatant Separators

Figure 2:
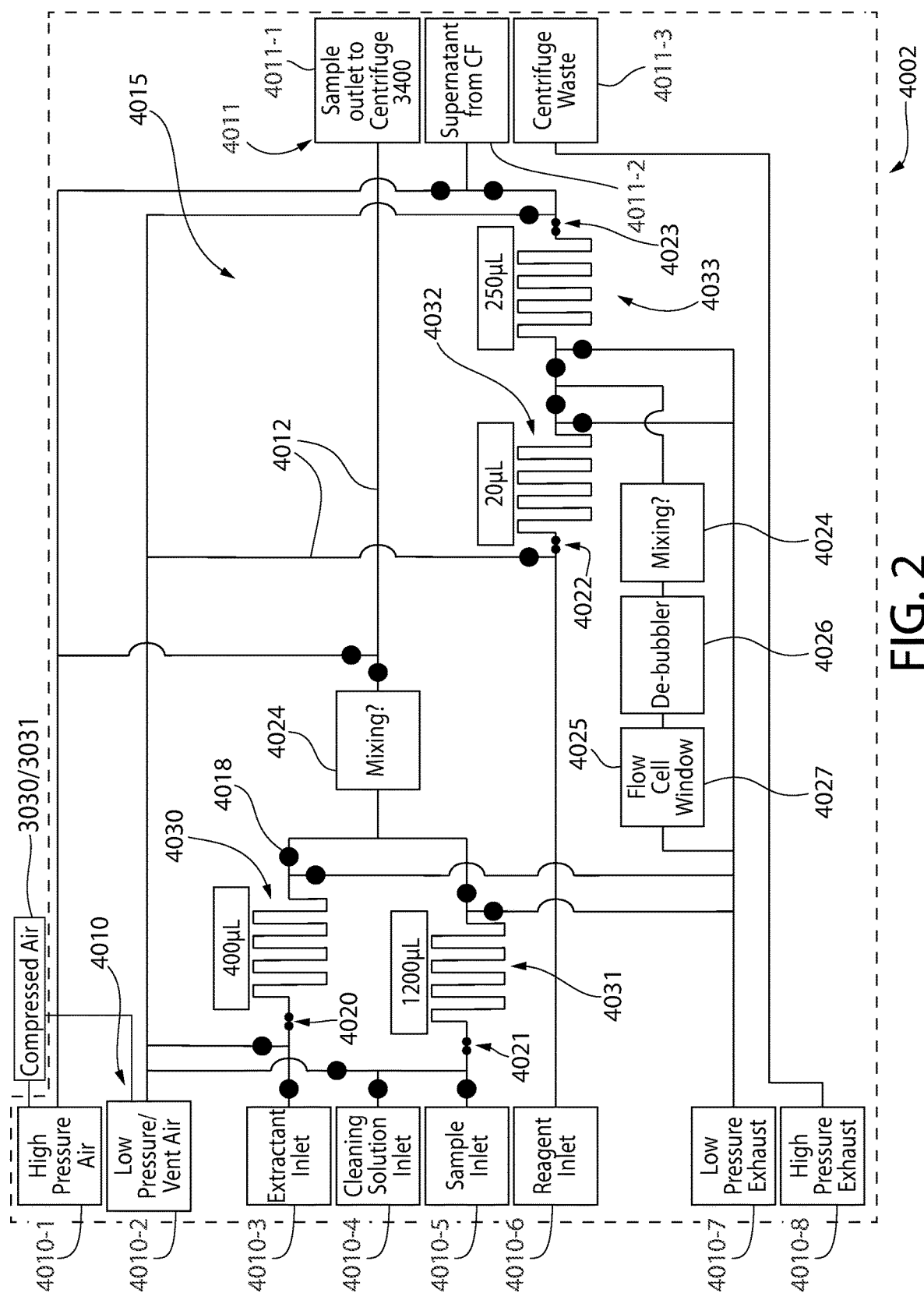
FIG. 2 is a schematic flow diagram showing a first embodiment of a microfluidic flow distribution network of a microfluidic manifold and its microfluidic devices for processing an agricultural sample slurry.
Figure 3:
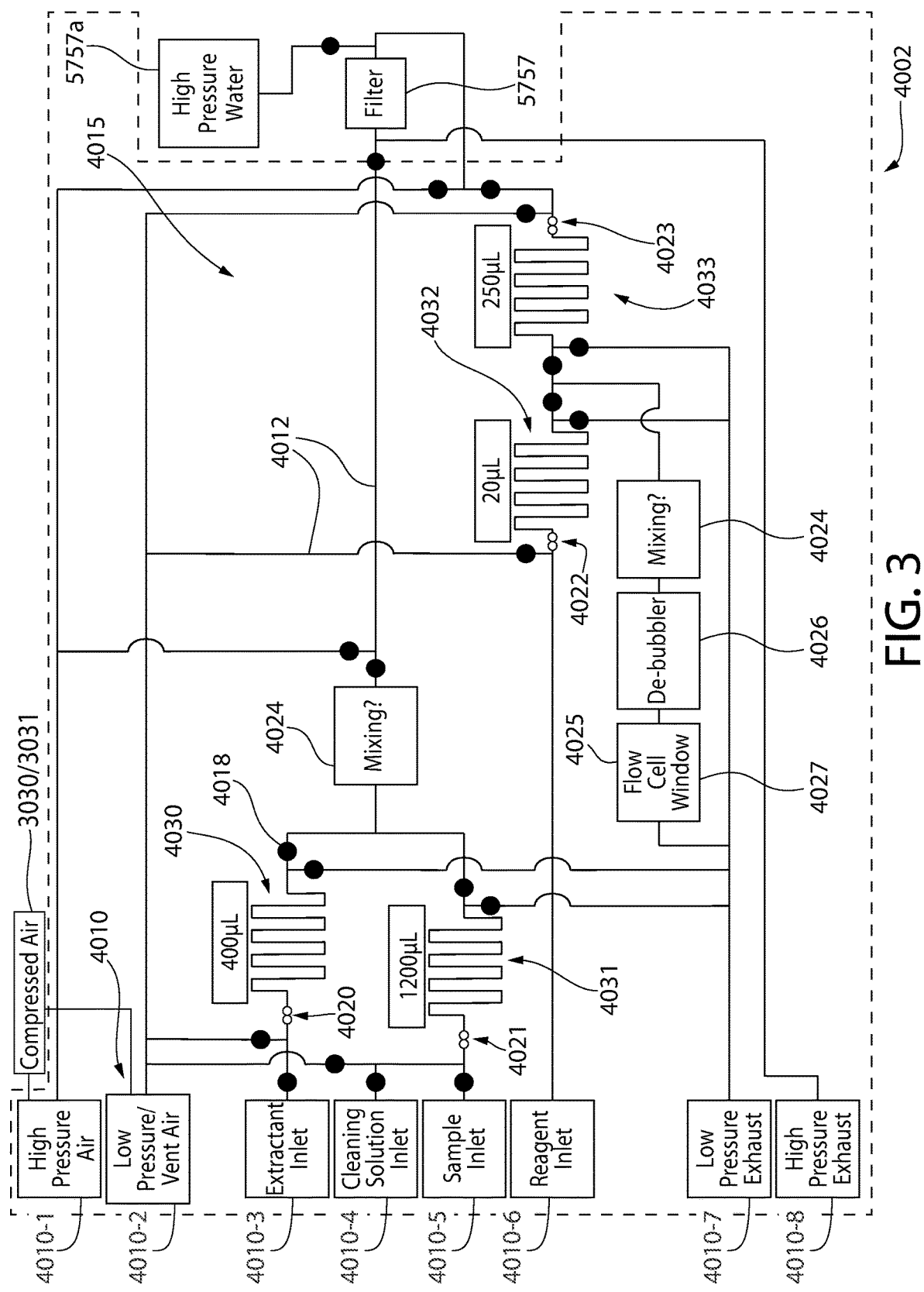
FIG. 3 is a schematic flow diagram showing a second embodiment of a microfluidic flow distribution network of a microfluidic manifold and its microfluidic devices for processing an agricultural sample slurry.

In some alternative embodiments, the liquid portion may be separated from the soil sample slurry and extractant mixture to produce clear supernatant for chemical analysis using a centrifuge or suitable filter media such an ultrafine microporous filter 5757 in lieu of the centrifuge. Suitable centrifuges include centrifuge 3400 and centrifuge tubes 3450 described in commonly-owned WO2020/012369. FIG. 2 shows chemical analysis sub-system 3003 of the agricultural system 3000 operably interfaced with a centrifuge. FIG. 3 shows the same but operably interfaced with microporous filter 5757 instead for producing the supernatant.

In some embodiments, a microporous sintered metal filter media of suitable shape and structure may be used for the microporous filter 5757. Of course, numerous other suitable types and configurations of filters may be used to suit the apparatus used to mount and retain the filter (e.g. disk shaped, cone shaped, solid cylinder shape, etc.). Other types of porous filter media may be used which are suitable for pressure requirements of the system (e.g., polymeric, etc.). Preferably, the filter media material and shape selected are suitable for backwashing. The microporous filter media selected is configured to produce a clear supernatant suitable for chemical analysis from the slurry and extractant mixture.

Once the supernatant is separated from the soil slurry, the filter may be back-flushed with clean high pressure liquid (e.g. filtered water) clean the filter media for reuse during the next soil sample run. To accomplish a backwash cycle, the flow paths formed in the system may be reconfigured by selectively opening/closing certain valves in combination to reverse filtered water flow through the filter media of filter 5757. The filter backwash is exhausted from the system.

Microfluidic Chemical Analysis Devices

FIGS. 3 and 4 previously described herein are flow diagrams showing the fluid flow paths (e.g., slurry, water, air, chemicals, etc.) and fluidic components of the chemical analysis sub-system 3003 incorporated in an analysis processing device such as a microfluidic manifold in the form of a processing wedge 4002 in one non-limiting embodiment. When using the microporous filter 5757 in FIG. 4 in lieu of the centrifuge shown in FIG. 3, the filter may be separate from and not incorporated into the processing wedge 4002 in one implementation as an integral part thereof (dashed lines schematically connoting the boundary of the wedge). In alternative implementations, however, the filter 5757 may be configured and constructed for integrating directly into the processing wedge 4002. Since the layers of microfluidic devices are typically permanently bonded together, the non-integrated filter arrangement allows the filter media to be readily replaced as needed without having to discard the entire processing wedge. Where a compact form factor is desired due to spatial constraints, however, the integrated filter arrangement may be preferable.

A suitable external off-disk high pressure filtered water source 5757a as shown in FIG. 3 may be provided for the filter backwash operations to clean the filter between different agricultural sample runs for chemical analysis. The microporous filter 5757 may be cleaned in a similar manner to that already described herein by reversing flow instead through the filter media of filter 5757 using high pressure water in a direction opposite that that used for filtering the agricultural slurry.

FIGS. 5-12 generally depict one non-limiting embodiment of a microfluidic processing disk 4000 comprised of a plurality of chemical analysis processing devices such as wedges 4002 in one non-limiting embodiment and configuration. Each wedge 4002 comprises a fluidly isolated chemical analysis sub-system 3003 which may be operably interfaced with either a centrifuge 3400 or microporous filter 5757 previously described herein for filtering the agricultural slurry and extractant mixture to produce the clear supernatant for chemical analysis. Advantageously, the microfluidic processing disk 4000 is a microfluidic device (e.g. M2D2) which is configured and operable to integrate and incorporate the entire slurry analysis system including substantially all aspects of fluid pumping, mixing, valving, and flow distribution and control shown in FIGS. 2 and 3 associated with handling the air, water, slurry, extractant, reagent, and supernatant fluids. The pumps, valving, mixing, and flow distribution functions for example are thus integrated into each processing wedge 4002 of the microfluidic processing disk 4000 in a known manner of constructing such microfluidic devices with active micro-components (e.g. pumps, valves, mixing chambers, etc.). This eliminates the need for the multiplicity of physically discrete and separate flow control devices (e.g. pumps, valves, mixing chambers, etc.) which conventionally need to be fluidly interconnected via extensive runs of tubing and tube connection, thereby allowing for improved compactness of the chemical processing analysis portion of the system.

The microfluidic processing disk 4000 advantageously provides single unified platform or device for processing and controlling flow of all the foregoing fluids in addition to chemical analysis and quantification of the analytes of interest extracted from the agricultural sample. The microfluidic processing disk 4000 further provides parallelization of the agricultural sample processing to reduce analysis time and quantification of all chemical parameters associated with the sample. Accordingly, the sample may be processed and chemically analyzed simultaneously in the plurality of processing wedges 4002 for all analytes of interest. Pressurized air provided by air compressor 3030 provides at least part the motive force for flowing and processing the foregoing fluids through each processing wedge of microfluidic processing disk 4000 in accordance with the flow charts of FIGS. 2 and 3, as further described herein. The air is also used to operate the micro-valving and micropumps which may be pneumatically actuated, as further described herein.

Referring initially to FIGS. 5-12, the microfluidic processing disk 4000 may have a generally annular disk-shaped composite body in one embodiment formed from multiple layers of material bonded or laminated together by any suitable means used in the art (e.g. adhesives, heat fusion, etc.). Each layer may be substantially planar or flat in the sandwiched construction, typical of such microfluidic devices (e.g. M2D2) sometimes referred to a "lab-on-a chip." The analysis processing wedges 4002 of microfluidic device are configured and operable to meter/measure, pumps, mix, and de-bubble the various fluids (air, water, slurry, extractant, reagent, etc.). One or more of the layers of each processing wedge are configured and patterned to create micro-sized channels, chambers/reservoirs, and air actuated diaphragm-operated valves and pumps embedded in the microfluidic device.

The materials used to construct the layers of the processing wedges 4002 of microfluidic processing disk 4000 may include a combination of rigid thermoplastics and flexible elastomeric material sheets. Transparent polymeric materials may be used in one embodiment to permit visual observation of the fluids being processed in the microfluidic processing disk 4000. The rigid plastics may be used to form the overall rigid substrate or body of microfluidic processing disk 4000 which defines its exposed exterior surfaces and includes an interior patterned to create a plurality of internal microchannels 4012 and chambers for creating the active microfluidic flow control devices (e.g. diaphragm-operated pumps, valves, mixing chambers, etc.). Examples of thermoplastics (polymers) which may be used include for example without limitation PMMA (polymethyl methacrylate commonly known as acrylic), PC (polycarbonate), PS (polystyrene), and others. Examples of suitable elastomeric materials which may be used include for example without limitation silicone, PDMS (polydimethylsiloxane), fluorosilicone, neoprene, and others. The pressurized air used to hold the microfluidic valves/pumps closed will permeate through elastomeric diaphragms over time, causing bubbles to develop in the liquid side of the device. These bubbles negatively affect the ability to volumize liquids properly, as the air bubbles displace the otherwise precise fluid volumes that are being manipulated. Fluorosilicone is one preferred non-limiting material due its low gas permeability property which aids in decreasing gas diffusion through the diaphragm over time to combat the foregoing problem.

The elastomeric materials used in each chemical analysis processing wedge 4002 may be used to form the flexible and deformable active portions of the microfluidic flow control devices such as the movable diaphragms of the micropumps and microvalves which are acted upon by air pressure (alternatively water pressure) to operate these pumps and valves for controlling fluid flow within the microfluidic processing disk 4000. This is typically achieved by forming a thin flexible elastomeric layer (e.g. silicon, PDMS, etc.) above a layer of the more rigid thermoplastic layer in disk 4000 which is patterned with the microchannels and microchambers associated with the pumps, valves, or mixing chambers, thereby forming a flexible roof portion thereof.

It bears noting that in some embodiments, the elastomeric material may be individually cut or otherwise formed to fit and complement the shape and size of each active microfluidic flow control devices in lieu of using an entire sheet or layer of the elastomeric material.

In one embodiment, the disk-shaped microfluidic processing disk 4000 comprises a plurality of generally interchangeable and separable triangular or "pie-shaped" chemical analysis processing wedges 4002. The wedges 4002 may be detachably interlocked together such as via suitable mechanical interlock features (e.g. snap-fit tabs/slots, etc.) and/or fasteners to collectively form the annular disk-shaped body of the processing disk 4000. In other embodiments, the wedges 4002 may be permanently joined together such as via adhesives or ultrasonic welding as some examples.

Each processing wedge 4002 of microfluidic processing disk 4000 is a discrete microfluidic device which may be fluidly isolated from every other processing wedge in one embodiment within the confines of the processing disk structure (i.e. no cross flow through the disk between wedges). Beyond the microfluidic processing disk physical boundary, however, individual processing wedges may fluidly share common inlet manifolds connected to a source fluid flow (e.g. water, slurry, air, chemical, etc.) or outlet manifolds (e.g. waste/exhaust manifold) for convenience of construction and cost efficiency. Each processing wedge 4002 is a complete chemical processing device or train operable to process and analyze a soil sample initially provided in slurry form (from one of the mixing stations previously described herein) for a different analyte. Advantageously, this provides a plurality of chemical processing trains (i.e. wedges 4002) capable of processing and analyzing soil samples simultaneously in parallel for different analytes (e.g. plant-available nutrients or other chemical constituents/properties) in conjunction with the centrifuge 3400. This parallelization reduces the time required for completely processing and analyzing a soil sample for multiple analytes.

With additional reference to FIGS. 13-16, it bears noting that when a centrifuge 3400 is used for producing the supernatant, microfluidic processing disk 4000 may be configured and operable to form a detachable fluid coupling to the centrifuge through intermediary fluid exchange dock 3430. Fluid exchange dock 3430 is fluidly coupled and interposed between the microfluidic processing disk 4000 and centrifuge 3400.

Centrifuge 3400 includes an aerodynamic cover assembly to streamline the tube hub 3500 assembly as it spins to reduce power input and noise due to aerodynamic losses since the tube hub which carries pivotable centrifuge tubes 3450 would act as an air impeller otherwise. The cover assembly comprises an upper cover 3520 and lower cover 3521 which are affixed to the hub such as via threaded fasteners in one embodiment or other mechanical fastening methods. The hub 3500 is thus sandwiched and compressed between the covers, as further shown in FIG. 66 which depicts the completed hub assembly.

Figure 15:
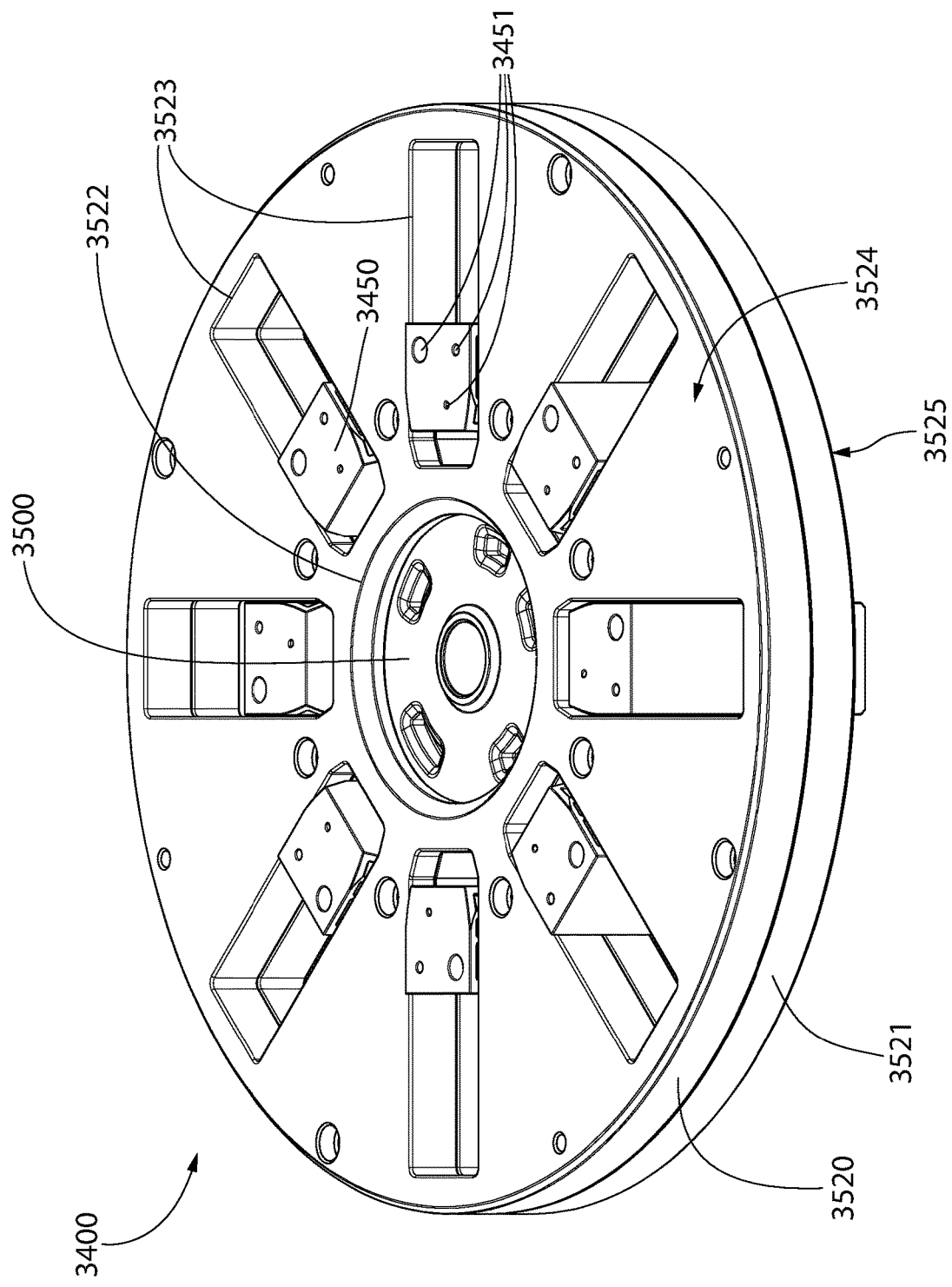
FIG. 15 is a top perspective view of a cover assembly for the tube hub showing the centrifuge tubes in a non-centrifugated vertical position.
Figure 16:
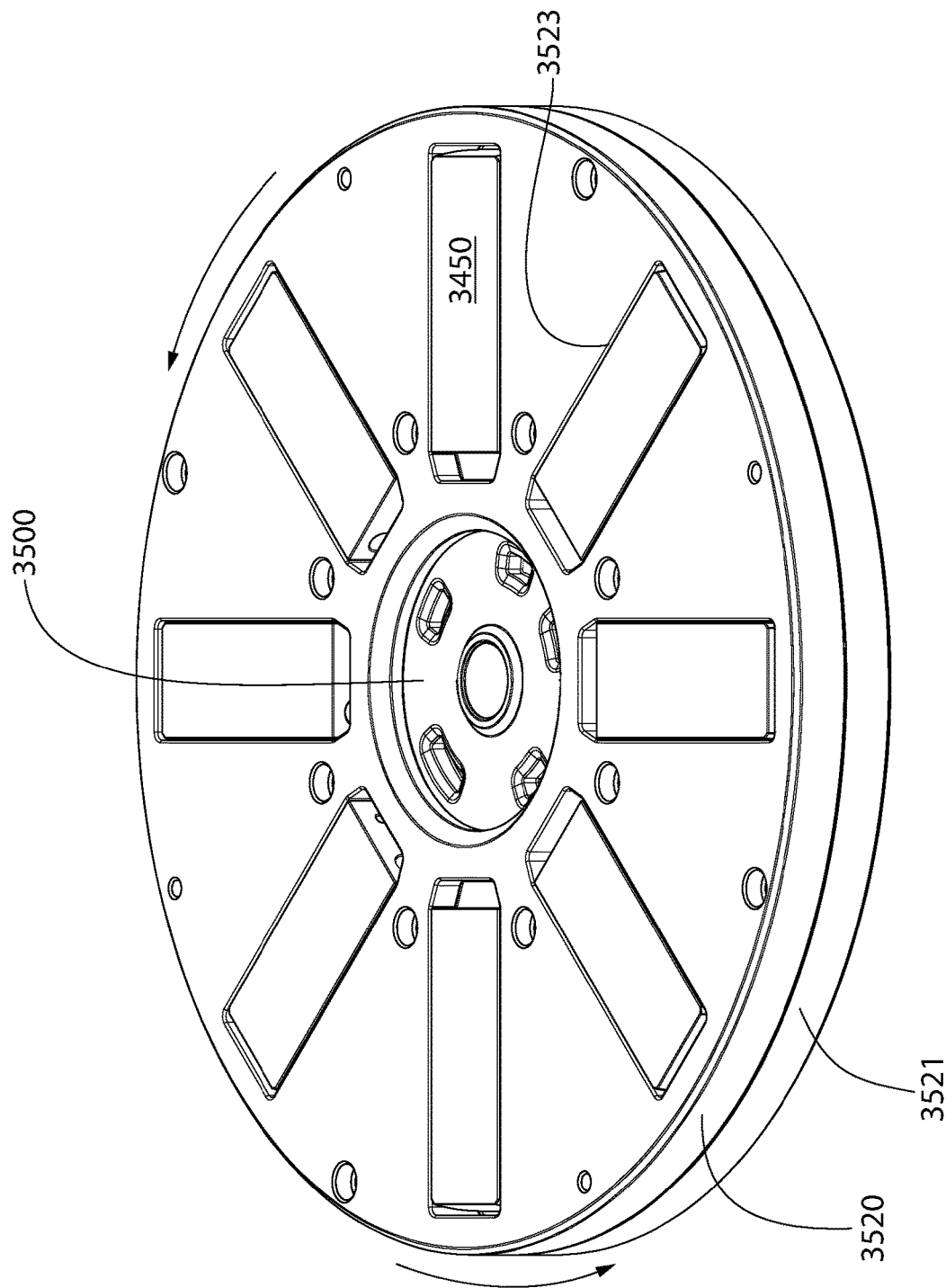
FIG. 16 is a view thereof showing the centrifuge tubes in a pivoted centrifugated horizontal position.

With continuing reference to FIGS. 13-16, each of the upper and lower covers 3520, 3521 may have a disk-shaped body including a central opening 3522 and plurality of rectangular tube openings 3523 formed completely through the cover between their top and bottom surfaces. Tube openings 3523 may be arranged in a circumferential pattern around central opening and are radially elongated as shown. The tube openings 3523 are arranged such that the mounted centrifuge tubes 3450 are exposed within the covers. Tube openings 3523 preferably have a radial length sized to allow the mounted centrifuge tube to fully swing outwards and upwards within the opening when rotated by the centrifuge 3400. Centrifuge tubes 3452 are each pivotably mounted in tube openings 3523 and angularly movable between a vertical position shown in FIG. 15 when the centrifuge 3400 is stationary, and a horizontal position shown in FIG. 16 when the centrifuge (e.g., cover assembly) and hub 3500 is rotated at full speed by the rotary centrifuge drive mechanism. This ensures that the acceleration experienced by the sample due to gravity or rotational acceleration is always away from the tube ports. The tubes 3450 are preferably configured such that the top surface is substantially flush with the top surface 3524 of the upper cover 3520, or preferably slightly raised and protruding above the top surface as seen in FIG. 15 to be engaged by the bottom surface 3432 of the fluid exchange dock 3430 to form a sealed connection between the flow ports 3451 of the tubes and flow passages 3434 of the dock 3500. In the vertical position, the centrifuge tubes 3450 project downwards below the bottom surface 3525 of the lower cover 3521 such that a majority of the height of the tube extends beneath the bottom surface 3525.

WO2020/012369 describes the centrifuge 3400 including the foregoing features and operation in greater detail.

Referring back now generally to FIGS. 5-16, each processing wedge 4002 of microfluidic processing disk 4000 may have a truncated wedge shape including a top major surface 4003, an opposing bottom major surface 4004, opposing arcuately curved inner and outer surfaces 4005, 4006, and a pair of converging radial side surfaces 4007. Side surfaces 4007 each define radial reference lines R1 which intersect at a geometric vertical centerline C1 of the processing wedge 4002. When the processing wedges 4002 are assembled together in microfluidic processing disk 4000, they collectively define a circular central opening 4014 (for purposes similar to central opening 3435 of dock 3430). Processing wedge 4002 defines an outer peripheral portion or region 4008 defined as proximate to outer surface 4006, and an inner hub portion or region 4009 defined as proximate to inner surface 4005. Although the non-limiting illustrated embodiment includes eight analysis processing wedges 4002, other embodiments may use more or less wedges.

A plurality of fluid exchange ports are formed in each processing wedge 4002. The ports may include a plurality of outer ports 4010 arranged in an array in peripheral region 4008 of the processing wedge, and a plurality of inner ports 4011 arranged in an array in the inner hub region 4009. In one embodiment, the outer ports 4010 may penetrate only the top major surface 4003 of the processing wedge 4002 and the inner ports 4010 may penetrate only the bottom major surface 4004. In one non-limiting implementation, as an example, eight outer ports 4010 and three inner ports 4011 may be provided as illustrated. Other numbers of ports may be used in other embodiments and is not limiting of the invention. The inner ports 4011 correspond in number and arrangement to the clusters 3433 of flow passages 3434 in the fluid exchange dock 3430 (see, e.g. FIGS. 13-14), which in turn match the flow ports 3451 formed in the top surface of centrifuge tubes 3450 for exchanging fluids when the tube hub 3500 is in the upper docked position. Inner ports 4011 may be mutually configured with the top inlets to the flow passages 3434 in the fluid exchange dock 3430 to form a detachable leak-resistant sealed joint therebetween. For example, inner ports 4011 may thus be configured with the same type nozzles 3436 shown in FIG. 56 on the bottom of fluid exchange dock 3430 to form a detachable sealed therewith in a similar manner.

Figure 12:
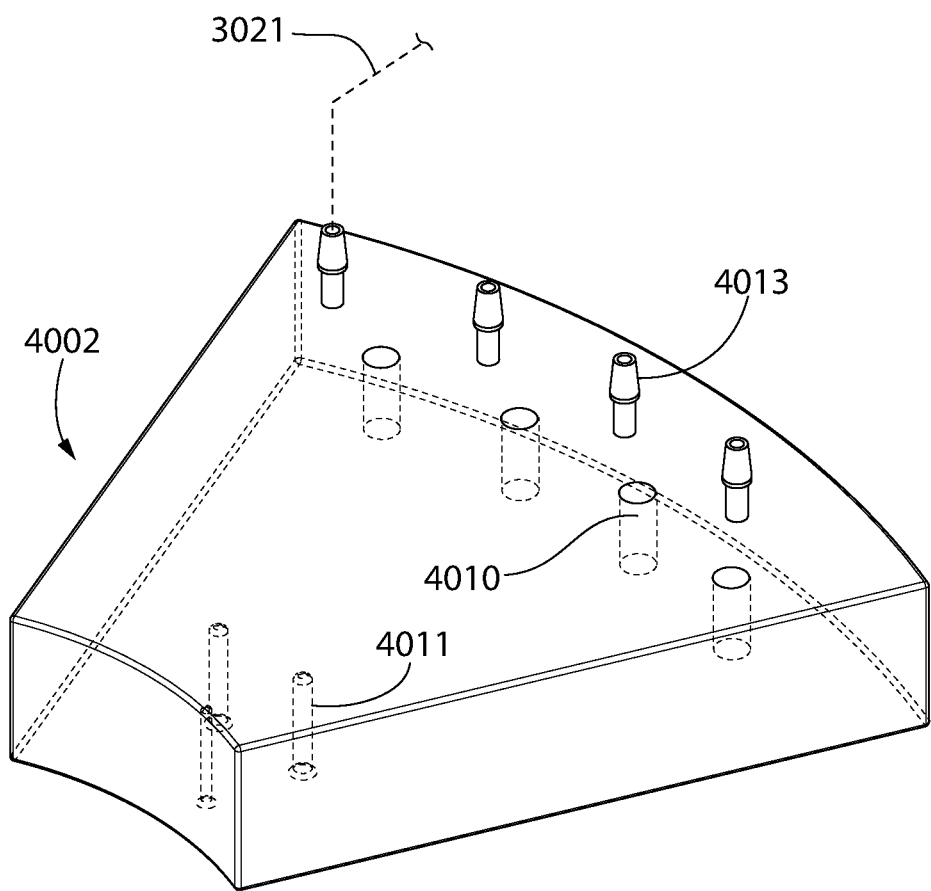
FIG. 12 is a perspective view of one processing wedge showing its flow conduits and external fluid connections.
Figure 13:
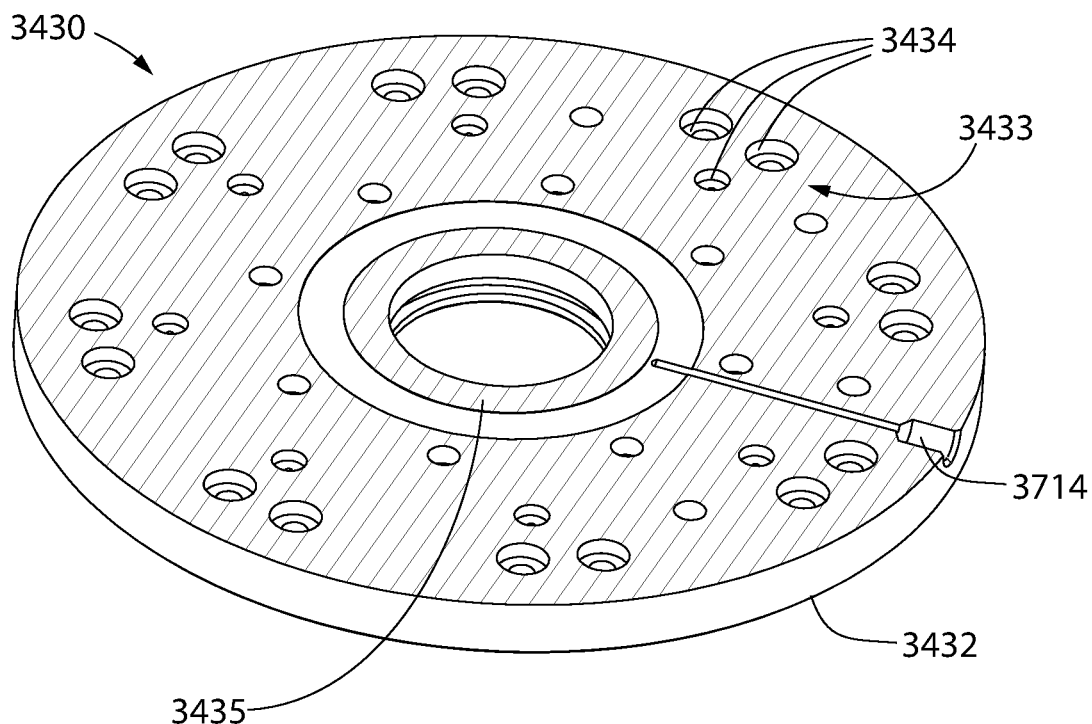
FIG. 13 is a top perspective view of a fluid exchange dock of the centrifuge.
Figure 14:
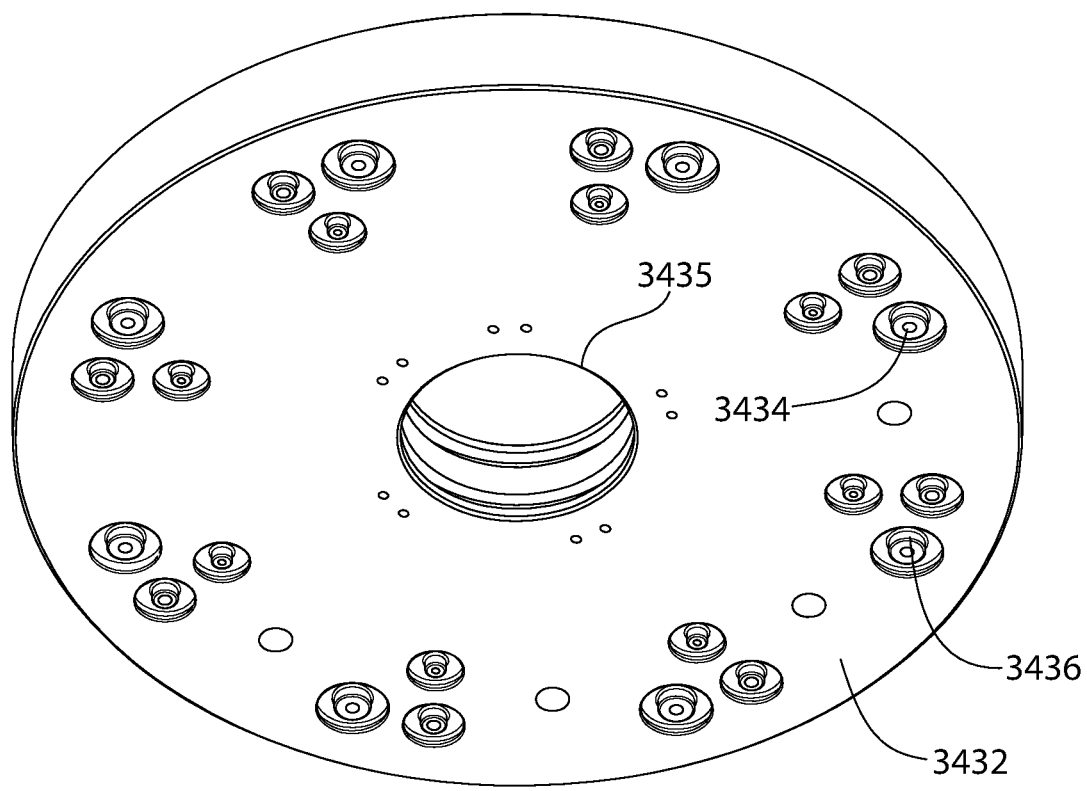
FIG. 14 is a bottom perspective view thereof.

Outer ports 4010 are configured for fluid connection to external process tubing 3021 (see, e.g. FIG. 12). In one embodiment, outer ports 4010 may optionally include upwardly protruding tubing barbs 4013 to facilitate the coupling (see, e.g. FIG. 12). Alternatively, outer ports 4010 may instead include recessed nozzles 3436 configured similarly to the inner ports 4011 which can also facilitate fluid connection to process tubing 3021 without having a protruding tubing barb.

Referring to the microfluidic processing wedge 4002 flow diagrams of FIGS. 2-3, the inner and outer ports 4010, 4011 are fluidly coupled together by a branched microchannel network 4015 of microchannels 4012 formed internally within the microfluidic processing disk 4000. On the liquid side, the microchannel network forms flow paths between the inner and outer ports, and fluidly couples the flow control microfluidic devices together embedded in microfluidic processing disk 4000. The flow network 4015 also includes air microchannels 4012 which forms air connections to the liquid microchannels and microfluidic flow control devices by the pneumatic system which may include sources of high pressure and low pressure air as shown. Pressurized air provided by air compressor 3030 (example shown in FIGS. 2-3) or another compressor/compressors which provide the motive force for flowing and processing the foregoing fluids through the microfluidic processing disk 4000 and analytical processing wedges 4002 in accordance with the flow diagrams and as described herein.

The microchannels 4012 (air and liquid) of each processing wedge 4002 are configured and patterned to form the functional layout and fluid connections represented in the flow diagrams of FIGS. 2 and 3 (recognizing that the physical layout may differ to create the functional connections shown). The blocks on the left of this figure represent the outer ports 4010 and those on the right represent the inner ports 4011 of each processing wedge 4002. It is well within the ambit of a microfluidic device manufacturer to create the depicted flow network (and flow control microfluidic devices shown) using computer-aided fabrication methods without undue further elaboration here. The microchannels 4012 may be formed in one or more of the layers of the microfluidic processing disk by any suitable process or combination of processes commonly used to construct microfluidic devices, such as for example without limitation micro-machining, laser milling, laser or chemical etching, lithography, hot embossing, injection molding, or other.

The microchannel network 4015 further includes a plurality of microfluidic valves, pumps, mixing chambers shown in FIGS. 2-3. In one embodiment, these microfluidic devices may be diaphragm operated and created using a flexible elastomeric flow control layer embedded within the microfluidic processing disk 4000 which is in communication with the microchannels and chambers created within the microfluidic processing disk 4000, as described elsewhere herein. The microfluidic devices may further include pneumatically-actuated diaphragm micropumps including extractant pump 4020, slurry pump 4021, reagent pump 4022, and transfer pump 4023. The microchannels 4012 are opened/closed by a plurality of pneumatically-actuated diaphragm microvalves 4018 schematically represented by circles (solid circle=closed; open circle=open). Pneumatically-actuated micro-mixing chambers 4024 may optionally be provided as required for mixing soil sample slurry with extractant, and/or upstream of the flow analysis cell 4027 and flow cell window 4025 each integrated into the processing wedge 4002 to ensure complete mixing of the color changing reagent (also sometimes referred to as "indicator") and supernatant if required. In some embodiments, the micro-mixing chambers 4024 may be formed by two closely fluidly coupled cells connected via a narrow short microchannel which is well known construction in the microfluidic arts. The cells are alternatingly pressurized by air to cyclically transfer the liquid back and forth multiple times between the cells, thereby providing thorough mixing. They mixers may or may not be diaphragm operated. It will be appreciated that other types of microfluidic mixers, pumps, and valves however may be used and the invention is not limited to the disclosed non-limiting examples.

Figure 17:
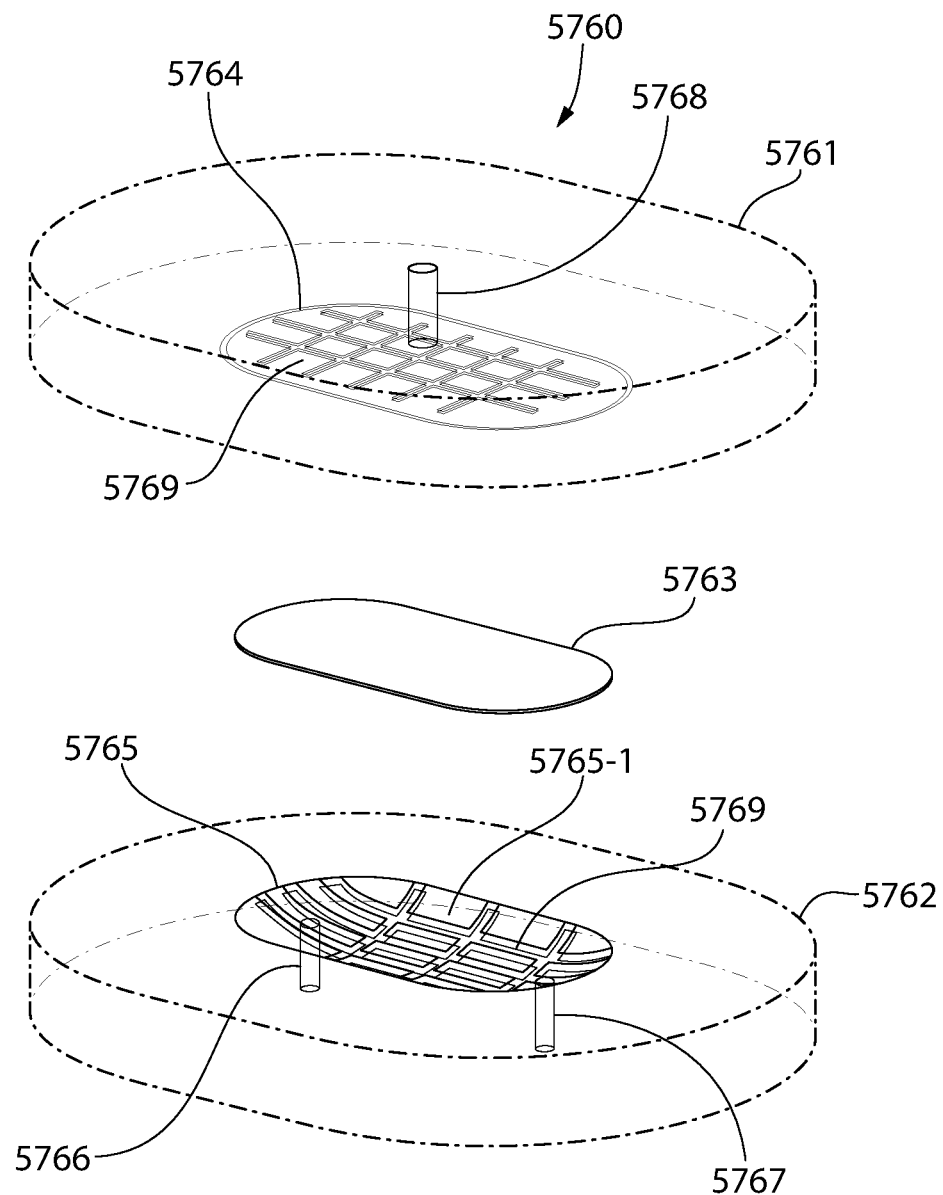
FIG. 17 is an exploded perspective view of an on-disk pneumatically-actuated diaphragm micropump mountable in the microfluidic processing disk of FIG. 96.
Figure 18:
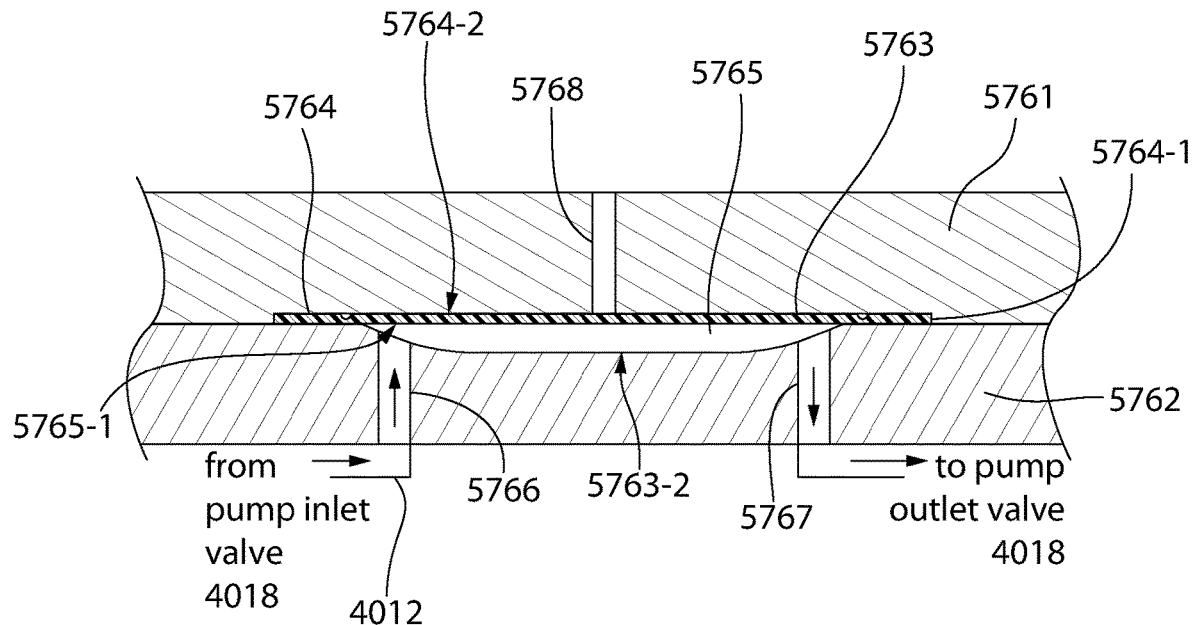
FIG. 18 is a side cross-sectional view thereof showing the micropump in an unactuated position.
Figure 19:
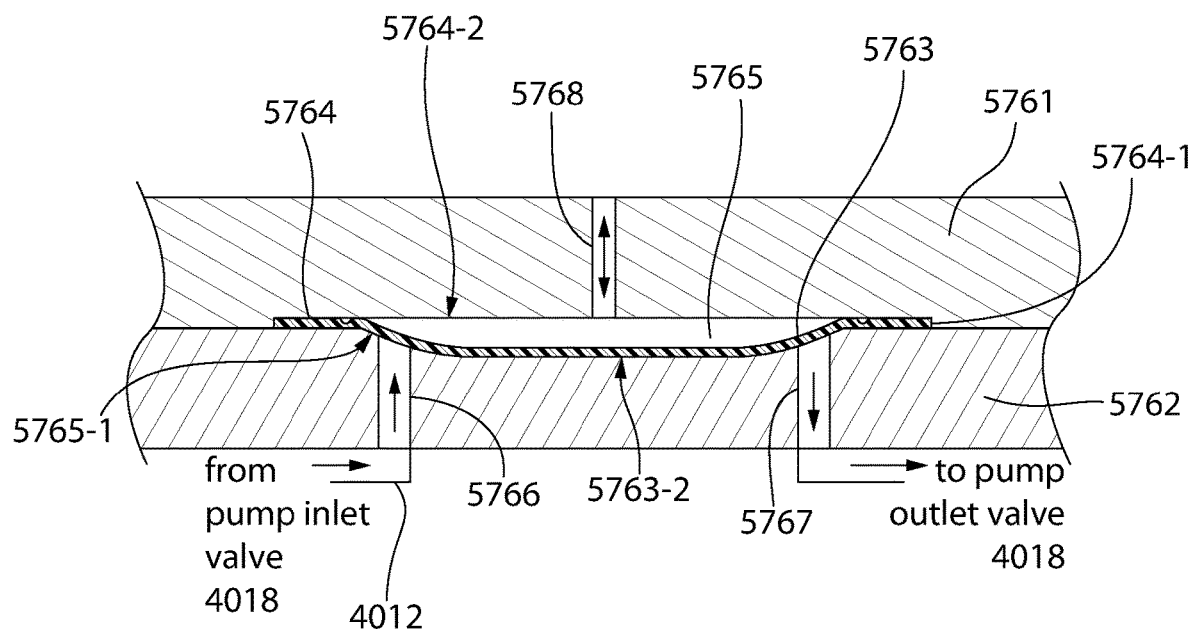
FIG. 19 is a view thereof showing the micropump in an actuated position.

FIGS. 17-19 are exploded and side cross-sectional views respectively of an on-disk pneumatically-actuated diaphragm micropump 5760, which may be used for the extractant pump 4020, slurry pump 4021, reagent pump 4022, transfer pump 4023, or other pumps that may be required. These pumps are incorporated into the microchannel network 4015 of each disk processing wedge 4002 and apply the motive force to the fluid to drive it through the microchannel network and various flow-related features of the disk. The micropumps and features shown are each integrally formed or molded within two adjacent layers of each wedge 4002 as unitary structural portions thereof.

Each micropump 5760 is a sandwiched structure including an upper layer 5761 of the microfluidic processing disk 4000 (e.g., processing wedge 4002), adjacent lower layer 5762 of the disk, and a thin resiliently deformable diaphragm 5763 having an elastic memory and defining a top surface 5763-1 and opposing bottom surface 5763-2. It bears particular note that the upper and lower layers 5761, 5762 are not necessary the uppermost (i.e. top) and lowermost (i.e. bottom) layers of the multi-layered microfluidic processing disk 4000, but instead may be two adjacent intermediate layers therebetween. In one non-limiting embodiments, the upper and lower layers 5761, 5762 are intermediate layers in a 5-layer processing disk 4000 recognizing that more or less layers may be used as needed to create the desired microfluidic devices and flow paths therein.

The diaphragm 5763 may be made of a suitable elastomeric material or polymer, such as silicone in some embodiments, and may have thicknesses less than 1 mm (0.04 inches). Diaphragm 5763 is resiliently movable between a normally flat standby condition when no pneumatic air pressure signal is applied and a deformed downwardly projecting convex actuated condition when air is applied to the top surface of the diaphragm. The diaphragm 5763 may be oval in one configuration; however, other shapes may be used.

The micropump 5760 further includes an upper pump chamber 5764 recessed into the bottom surface of the upper layer 5761 of microfluidic processing disk 4000, and a concavely shaped lower pump chamber 5765 directly opposing and vertically aligned with the upper chamber formed in the lower layer 5762. The upper chamber 5764 may have straight sidewall surfaces 5764-1 and a flat top surface 5764-2 in some embodiments. Lower chamber 5765 is recessed into the top surface of lower layer 5762 and may include including arcuately curved sidewall surfaces 5765-1 which extend perimetrically around the chamber to define the concavity. A flat bottom surface 5765-2 adjoins the sidewall surfaces around the perimeter of the lower chamber as shown. The curved sidewall surfaces ensure that the diaphragm 5763 does not tear or crack when actuated over multiple operating cycles. It bears noting that the lower chamber 5765 defines the volumetric pumping capacity of the micropump which is expelled with each actuation of the micropump.

The micropump 5760 further includes a pneumatic air pressure signal port 5768 formed in upper layer 5761 which in fluid communication with the upper chamber 5764. Port 5768 is preferably centered in the top surface of the upper chamber 5764 and in fluid communication with a pneumatic or air microchannel network 4015-1 formed in the disk layer immediately above the upper layer 5761 and fluidly coupled to an air source such as those described herein. The lower layer 5762 includes a fluid inlet port 5766 for introducing fluid into the lower chamber 5765, and a fluid outlet port 5767 for discharging fluid from the lower chamber caused by operation of the micropump 5760. Each port 5766, 5767 is thus in fluid communication with the lower chamber 5765. The fluid inlet port 5766 preferably penetrates the lower chamber 5765 at an opposite end of the chamber than its outlet port 5767 at the other end. Each of the fluid inlet and outlet ports is in fluid communication with the fluid microchannel network 4015 formed in the disk layer immediately below the lower layer 5762. In one embodiment, the upper and lower chambers 5761, 5762 may be oval shaped; however, other shapes may be used.

Operation of micropump 5760 will be briefly described. Each micropump has an associated fluid inlet diaphragm microvalve 4018 and fluid outlet diaphragm microvalves 4018 fluidly coupled to the fluid inlet and outlet ports 5766, 5767 respectively which are necessary for operation of the micropump. The diaphragm valves have the same general construction and operation as the micropumps including a diaphragm, air pressure signal port, and fluid inlet and outlet ports. Operation of the valves between an open and closed position is performed in the same manner as described below for the micropumps which are thus analogous in structure and function to the valves. The valves however are generally smaller in size due to the multitude of valves arranged in the microfluidic processing disk 4000 to conserve space, and typically utilize circular diaphragms and upper and lower chambers in contrast to the elongated features of the micropumps intended to hold a predetermined volume of fluid necessary for the chemical processes and soil analysis.

FIG. 18 shows the pump in the initial flat unactuated or standby condition. Diaphragm 5763 is fully nested inside upper pump chamber 5764 and does not project downwards into lower pump chamber 5765. The diaphragm is trapped in the upper chamber 5764 between the upper and lower disk layers 5761, 5762. No air is applied to the diaphragm at this stage. The fluid outlet diaphragm microvalve 4018 is first closed and the fluid inlet diaphragm valve is opened to fill the lower chamber 5765 beneath the diaphragm with the fluid to be pumped from the microchannel network 4015 (e.g. soil slurry, extractant, reagent, supernatant, or other fluid). The fluid inlet diaphragm microvalve 4018 is then closed and the fluid outlet diaphragm microvalve 4018 is opened.

To pump the fluid volume contained in the lower pump chamber 5765, air is supplied to the top of the diaphragm 5763 via the air pressure signal port 5768 from the air source which is controlled by an air valve. The air pressure drives the diaphragm downward, which deforms and generally conforms to the shape of the lower chamber 5765, thereby expelling the fluid through the fluid outlet port 5767 and its associated outlet microvalve 4018. The diaphragm 5763 is now in the deformed convex actuated condition shown in FIG. 19. After pumping is completed, the air pressure is relieved from the air pressure signal port 5768 and the diaphragm 5763 returns to its original undeformed flat standby condition ready for the next pumping cycle.

In testing, it was discovered that if smooth surfaces are provided within the lower pump chamber 5765, the flexible diaphragm 5763 tends on occasion to get sucked into the fluid outlet port 5767 for either the pneumatic signal or fluid liquid-side communication prematurely. This unfortunately blocks fluid flow and pumping before the diaphragm is fully displaced/deformed and prevents the liquid volume in the lower chamber from being fully expelled. This causes inconsistency in the volume of fluid pumped per actuation, which can adversely affect proper slurry processing and analysis since the volumetric capacity for each pump chamber is carefully predetermined and exacting to ensure the proper ratio of chemicals (e.g. reagent, extractant, etc.) are mixed with the slurry.

To combat the foregoing diaphragm and pumping problems, the concave lower pump chamber 5765 preferably is provided with a plurality of "anti-stall" grooves 5769 which act to keep the flexible diaphragm 5763 from getting sucked into the fluid outlet port 5767 and blocking flow. This also prevents the diaphragm from attaching via formation of suction to but not fully releasing from the generally flat bottom surface 5765-2 of the lower pump chamber. The anti-stall grooves 5769 are therefore configured to prevent adherence of the diaphragm 5763 to the lower pump chamber 5765, thereby advantageously allowing the diaphragm 5763 to fully and reliably displace substantially the entire volumetric fluid contents of the lower chamber with each pumping cycle, thereby ensuring accuracy of the amount of fluid dispensed and ultimate soil slurry analysis. The recessed anti-stall grooves 5769 are cut or otherwise formed into preferably all surfaces within the lower chamber 5765 (e.g. sidewall surfaces 5765-1 and flat bottom surface 5765-2), as shown in FIG. 17. In one embodiment, the grooves 5769 may be arranged in a two-directional perpendicularly intersecting grid array of grooves as shown forming a somewhat checkerboard pattern. In other embodiments, the grooves may be unidirectional and formed by a plurality of non-intersecting and spaced apart parallel grooves arranged either along the major axis or minor axis of the lower chamber 5765, or diagonally to the axes. In some embodiments, the upper pump chamber 5764 formed in the upper disk layer 5761 may include anti-stall grooves similar to or different in configuration than the grooves in the lower chamber 5765. Any suitable pattern and number of grooves may be provided.

The microchannel network 4015 may further include a plurality of microreservoirs of predetermined volume for holding and staging the extractant, reagent, slurry, etc. for processing. In one embodiment, this may include an extractant microreservoir 4030, soil slurry microreservoir 4031, reagent microreservoir 4032, and supernatant microreservoir 4033. The microreservoirs 4030-4033 may be formed by a series of closely spaced, undulating loops of microchannels as shown. Sample non-limiting volumetric capacities of each microreservoir are shown in FIG. 2. Other volumetric capacities, however, may of course be used.

The process described below and in the flow diagrams of FIGS. 2-3 may be automatically controlled and executed by the system programmable controller, such as for example processing system controller 2820 shown in FIG. 4 (see, e.g. system interface block 2803). The controller is operably coupled to the low and high pressure air supply, such as provided by air compressor 3030. The low pressure air may be created in any suitable known manner such as by employing a pressure reducing valve station taking suction from the air tank 3031 associated with compressor 3030, which may contain high pressure air produced by the compressor. All air supply related components (compressor, tank(s), and valves) may therefore be controlled by the system programmable controller (e.g. processing system 2820). Other sources of low and high pressure air for pneumatically controlling operation of the microfluidic processing disk 4000 such as separate compressors may of course be used. The controller 2820 via pneumatic operation of the microvalves 4018 shown in FIGS. 2-3 may further control operation of the various fluid inlets 4010-2 to 4010-6 of the processing wedge 4002, exhaust/waste outlets 4010-7 to 4010-8, and fluid interface with either the centrifuge 3400 or microporous filter 5757 each previously described herein.

To reiterate, as previously noted, the blocks on the left of the flow diagrams represent the outer ports 4010 of the respective processing wedge 4002 and blocks on the right represent the inner ports of the wedge. In one implementation, the outer ports 4010 may include a high pressure air inlet 4010-1, low pressure air inlet 4010-2 also configured to operate as an air vent when required, extractant inlet 4010-3, cleaning solution 4010-4, slurry sample inlet 4010-5, reagent (indicator) inlet 4010-6, low pressure exhaust outlet 4010-7, and high pressure exhaust outlet 4010-8. The cleaning solution provided to inlet 4010-4 may be any suitable solution including deionized water or other. The inner ports 4011 may include a slurry sample outlet 4011-1 from processing wedge 4002 to centrifuge 3400 (i.e. centrifuge tube 3450), supernatant inlet 4011-2 from centrifuge 3400, and centrifuge waste inlet 4011-3 from the centrifuge. Other types and numbers of outer and inner ports 4010, 4011 may of course be provided.

FIGS. 2-3 shows the provision of the microfluidic processing disk 4000 and one of the processing wedges 4002 with integrated microchannel network 4015 at the start and readied for processing and chemically analyzing an agricultural sample such as without limitation a soil sample in slurry form. An example of processing and analyzing the slurry for analytes of interest is previous described herein and in commonly-owned WO2020/012369.

In one non-limiting embodiment, the slurry sample and extractant measurement loops (reservoirs) are pumped together into an optional first micro-mixing chamber 4024 where they are mixed. In some situations, adequate mixing of the sample and extractant may be achieved within the microchannels 4012 to obviate the need to a separate micro-mixing chamber (hence designation of the same with a "?" in the figure). Diaphragm-operated micropumps 4020, 4021 are pressurized with low pressure air as shown to achieve pumping of the fluids. Complete mixing of the slurry sample and extractant is then performed. Next, the extractant/sample mixture is pumped from first micro-mixing chamber 4024 to the centrifuge 3400 for processing. The supernatant and reagent are staged and pumped into their respective measurement loops (i.e. microreservoirs 4033 and 4032 at a precise predetermined ratio of supernatant to reagent. Some supernatant and reagent are very briefly dumped to waste via the flow path to lower pressure exhaust outlet 4010-7 to ensure these microreservoirs are completely filled. The supernatant and reagent are then pumped to a second micro-mixing chamber 4024. Note that the microchannel flow path comprising the micro-mixing chamber 4024, de-bubbler 4026, and flow cell window 4025 are active and fluidly connected to low pressure exhaust outlet 4010-7. Complete mixing of the supernatant and reagent is performed in the second micro-mixing chamber 4024, thereby causing a color change in the solution for detection by the absorbance analysis flow cell 4027 via downstream flow cell window 4025. The supernatant and reagent mixture incorporating the analyte therein is then pumped through the de-bubbler 4026 in the de-bubbling station which removes any residual air bubbles entrained in the mixture. Bubbles in the liquid stream may cause volume anomalies in the downstream flow analysis cell 427 and adversely affect analytical accuracy. De-bubblers are well known devices in the art without further undue elaboration.

Figure 20:
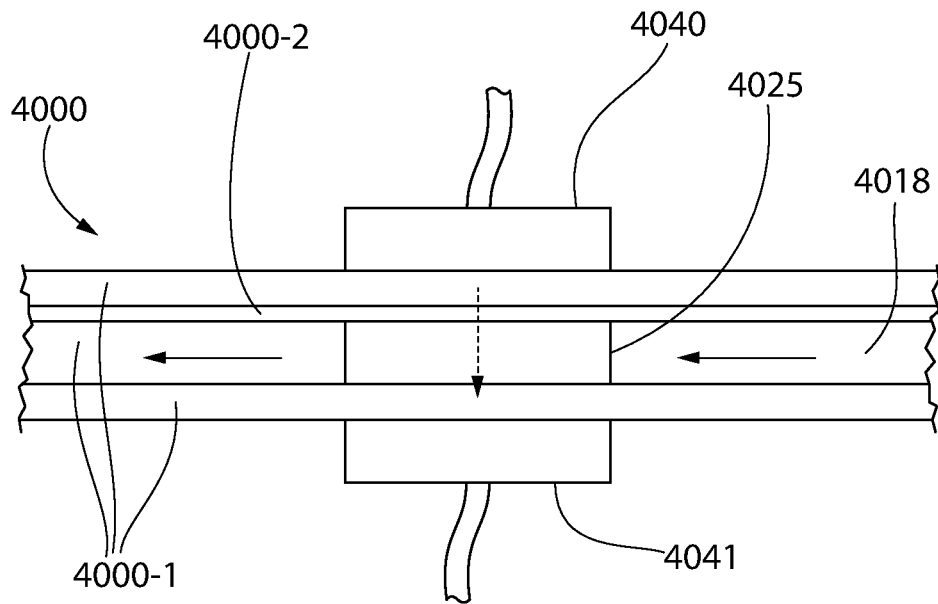
FIG. 20 is a side cross sectional view of an light emitting diode (LED) emitting diode assembly and LED receiving diode assembly associated with the flow analysis cell window shown in FIG. 2 or 3 for measuring an analyte.
Figure 21:
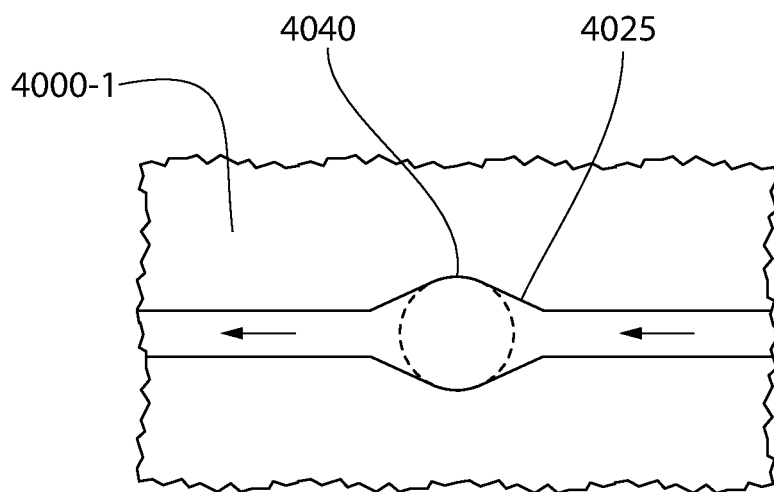
FIG. 21 is a top cross sectional view thereof.

The supernatant/reagent mixture incorporating the analyte is then pumped into flow cell window 4025 of absorbance flow analysis cell 4027 for colorimetric measurement by the absorbance flow analysis cell 4027. The present flow analysis cell 4027 may be formed integrally with and incorporated directly into a portion of processing wedge 4002. FIGS. 20 and 21 schematically depict the portion of wedge 4002 containing absorbance flow analysis cell 4027 and flow cells window 4025 formed within the bonded layer structure of the processing wedge. In the exemplary non-limiting construction shown, the layers comprises three hard plastic layers 4000-1 (e.g. PC, etc.) forming a top layer, bottom layer, and intermediate patterned with the foregoing microchannels and other fluid control devices such as the micropumps, microvalves, and micro-mixing chambers. The thin flexible elastomeric layer 4000-2 (e.g. silicon, etc.) is formed immediately on top of the intermediate hard layer 4000-1 for functioning as a diaphragm of the fluid control devices. In one embodiment, flow analysis window 4025 may be a laterally widened diamond-shaped chamber (see, e.g. FIG. 21). An LED emitting diode assembly 4040 and LED receiving diode assembly 4041 are mounted above and below the flow analysis window 4025 respectively. Diode assemblies 4040, 4041 are attached to the outmost top and bottom surfaces of processing wedge 4002 above and below window 4025 as shown, but fluidly isolated from the window and liquid flow stream in the processing wedge 4002. Layer 4000-2 may have a cutout formed directly above flow analysis window 4025 corresponding in size and shape to the emitting diode assembly 4040 to avoid possible reflective/refractive interference with the emitted analysis light beam.

In operation, the liquid reagent and supernatant mixture flows through flow analysis window 4025 (see, e.g. solid liquid flow arrows). As the flow passes through the window 4025, the emitting diode assembly 4040 transmits and shines light through the window and liquid therein to the receiving diode assembly 4041 for colorimetric measurement in a known manner. The measurement of the analyte in the sample mixture liquid stream is transmitted to the system programmable controller for analysis and quantification. During the analysis, it bears noting that the sample mixture flows continuously through the flow cell window 4025 to the low pressure exhaust outlet 41010-7 where it is then dumped to waste.

It bears noting that the micro-mixing chambers 4024 described above may be omitted in some instances if complete mixing can be achieved within the microchannels themselves. The micro-mixing chambers 4024 are therefore optional for use when required.

After the soil sample has been fully processed in the above manner, the system programmable controller 2820 is configured to initiate a cleaning cycle to prepare the microfluidic processing disk 4000 for processing a new soil sample. Cleaning solution and low pressure air are each selectively and alternately pumped into and through the emboldened active sample loop microchannels 4012 and through the centrifuge 3400 to the high pressure exhaust outlet 4010-8 as shown (FIG. 2). This clears residual soil slurry and chemicals from these components and microchannels. After several cycles of alternating cleaning solution and purge air is processed through the microchannels and centrifuge, at this point, the sample loop and flow paths upstream of the of the sample loop microchannels has only air in it. There is a column containing a mixture of air and cleaning solution remaining in the emboldened section of flow path. The microvalves 4018 open to allow high pressure air from high pressure air inlet 4010-1 to force the air/cleaning solution mixture column through the centrifuge 3400. The high pressure air then purges the centrifuge and flows to the high pressure exhaust outlet 4010-8, which completes the cleaning cycle.

The same microfluidic process described above with respect to FIG. 2 for processing wedge 4002 is generally applicable to a processing wedge which operably and fluidly interfaces with ultrafine microporous filter 5757 shown in FIG. 3 in line of a centrifuge for producing the supernatant for chemical analysis.

As already noted herein, the agricultural sampling system, sub-systems, and related processes/methods disclosed herein may be used for processing and testing soil, vegetation/plants, manure, feed, milk, or other agricultural materials for related parameters of interest. Particularly, embodiments of the chemical analysis portion of the system (chemical analysis sub-system 3003) disclosed herein can be used to test for multitude of chemical-related parameters and analytes (e.g. nutrients/chemicals of interest) in other areas beyond soil and plant/vegetation sampling. Some non-limiting examples (including soil and plants) are as follows.

Soil Analysis: Nitrate, Nitrite, Total Nitrogen, Ammonium, Phosphate, Orthophosphate, Polyphosphate, Total Phosphate, Potassium, Magnesium, Calcium, Sodium, Cation Exchange Capacity, pH, Percent Base Saturation of Cations, Sulfur, Zinc, Manganese, Iron, Copper, Boron, Soluble Salts, Organic Matter, Excess Lime, Active Carbon, Aluminum, Amino Sugar Nitrate, Ammoniacal Nitrogen, Chloride, C:N Ratio, Electrical Conductivity, Molybdenum, Texture (Sand, Silt, Clay), Cyst nematode egg counts, Mineralizable Nitrogen, and Soil pore space.

Plants/Vegetation: Nitrogen, Nitrate, Phosphorus, Potassium, Magnesium, Calcium, Sodium, Percent Base Saturation of Cations, Sulfur, Zinc, Manganese, Iron, Copper, Boron, Ammoniacal Nitrogen, Carbon, Chloride, Cobalt, Molybdenum, Selenium, Total Nitrogen, and Live plant parasitic nematode.

Manure: Moisture/Total Solids, Total Nitrogen, Organic Nitrogen, Phosphate, Potash, Sulfur, Calcium, Magnesium, Sodium, Iron, Manganese, Copper, Zinc, pH, Total Carbon, Soluble Salts, C/N Ratio, Ammoniacal Nitrogen, Nitrate Nitrogen, Chloride, Organic Matter, Ash, Conductance, Kjeldahl Nitrogen, *E. coli*, Fecal Coliform, *Salmonella*, Total Kjeldahl Nitrogen, Total Phosphate, Potash, Nitrate Nitrogen, Water Soluble Nitrogen, Water Insoluble Nitrogen, Ammoniacal Nitrogen, Humic Acid, pH, Total Organic Carbon, Bulk Density (packed), Moisture, Sulfur, Calcium, Boron, Cobalt, Copper, Iron, Manganese, Arsenic, Chloride, Lead, Selenium, Cadmium, Chromium, Mercury, Nickel, Sodium, Molybdenum, and Zinc Feeds: Alanine, Histidine, Proline, Arginine, Isoleucine, Serine, Aspartic Acid, Leucine, Threonine, Cystine, Lysine, Tryptophan, Glutamic Acid, Methionine, Tyrosine, Glycine, Phenylalanine, Valine (Requires Crude Protein), Arsenic, Lead, Cadmium, Antimony, Mercury Vitamin E (beta-tocopherol), Vitamin E (alpha-tocopherol), Vitamin E (delta-tocopherol), Vitamin E (gamma-tocopherol), Vitamin E (total), Moisture, Crude Protein, Calcium, Phosphorus, ADF, Ash, TDN, Energy (Digestible and Metabolizable), Net Energy (Gain, Lactation, Maintenance), Sulfur, Calcium, Magnesium, Sodium, Manganese, Zinc, Potassium, Phosphorus, Iron, Copper (not applicable to premixes), Saturated Fat, Monounsaturated Fat, Omega 3 Fatty Acids, Polyunsaturated Fat, Trans Fatty Acid, Omega 6 Fatty Acids (Requires Crude or Acid Fat), Glucose, Fructose, Sucrose, Maltose, Lactose, Aflatoxin (B1, B2, G1, G2), DON, Fumonisin, Ochratoxin, T2-Toxin, Zearalenone, Vitamin B2, B3, B5, B6, B7, B9, and B12, Calories, Chloride, Crude fiber, Lignin, Neutral Detergent Fiber, Non Protein Nitrogen, Selenium U.S. patent, Total Iodine, Total Starch, Vitamin A, Vitamin D3, and Free Fatty Acids.

Forages: Moisture, Crude Protein, Acid Detergent Fiber ADF, NDF, TDN, Net Energy (Gain, Lactation, Maintenance), Relative Feed Value, Nitrate, Sulfur, Copper, Sodium, Magnesium, Potassium, Zinc, Iron, Calcium, Manganese, Sodium, Phosphorus, Chloride, Fiber, Lignin, Molybdenum, Prussic Acid, and Selenium USP.

Milk: Butterfat, True Protein, Somatic Cell Count, Lactose, Other Solids, Total Solids, Added Water, Milk Urea Nitrogen, Acidity, pH, Antibiotic tests, and Micro-organisms.

Control System

FIG. 4 is a schematic system diagram showing the control or processing system 2800 including programmable processor-based central processing unit (CPU) or system controller 2820 as referenced to herein. System controller 2820 may include one or more processors, non-transitory tangible computer readable medium, programmable input/output peripherals, and all other necessary electronic appurtenances normally associated with a fully functional processor-based controller. Control system 2800, including controller 2820, is operably and communicably linked to the different soil sample processing and analysis systems and devices described elsewhere herein via suitable communication links to control operation of those systems and device in a fully integrated and sequenced manner.

Referring to FIG. 4, the control system 2800 including programmable controller 2820 may be mounted on a stationary support in any location or conversely on a translatable self-propelled or pulled machine (e.g., vehicle, tractor, combine harvester, etc.) which may include an agricultural implement (e.g., planter, cultivator, plough, sprayer, spreader, irrigation implement, etc.) in accordance with one embodiment. In one example, the machine performs operations of a tractor or vehicle that is coupled to an implement for agricultural operations. In other embodiments, the controller may be part of a stationary station or facility.

Control system 2800, whether onboard or off-board a translatable machine, generally includes the controller 2820, non-transitory tangible computer or machine accessible and readable medium such as memory 2805, and a network interface 2815. Computer or machine accessible and readable medium may include any suitable volatile memory and non-volatile memory or devices operably and communicably coupled to the processor(s). Any suitable combination and types of volatile or non-volatile memory may be used including as examples, without limitation, random access memory (RAM) and various types thereof, read-only memory (ROM) and various types thereof, hard disks, solid-state drives, flash memory, or other memory and devices which may be written to and/or read by the processor operably connected to the medium. Both the volatile memory and the non-volatile memory may be used for storing the program instructions or software. In one embodiment, the computer or machine accessible and readable non-transitory medium (e.g., memory 2805) contains executable computer program instructions which when executed by the system controller 2820 cause the system to perform operations or methods of the present disclosure including measuring properties and testing of soil and vegetative samples. While the machine accessible and readable non-transitory medium (e.g., memory 2805) is shown in an exemplary embodiment to be a single medium, the term should be taken to include a single medium or multiple media (e.g., a centralized or distributed database, and/or associated caches and servers) that store the one or more sets of control logic or instructions. The term "machine accessible and readable non-transitory medium" shall also be taken to include any medium that is capable of storing, encoding or carrying a set of instructions for execution by the machine and that cause the machine to perform any one or more of the methodologies of the present disclosure. The term "machine accessible and readable non-transitory medium" shall accordingly also be taken to include, but not be limited to, solid-state memories, optical and magnetic media, and carrier wave signals.

Network interface 2815 communicates with the agricultural (e.g. soil or other) sample processing and analysis systems (and their associated devices) described elsewhere (collectively designated 2803 in FIG. 4), and other systems or devices which may include without limitation implement 2840 having its own controllers and devices.

The programmable controller 2820 may include one or more microprocessors, processors, a system on a chip (integrated circuit), one or more microcontrollers, or combinations thereof. The processing system includes processing logic 2826 for executing software instructions of one or more programs and a communication module or unit 2828 (e.g., transmitter, transceiver) for transmitting and receiving communications from network interface 2815 and/or agricultural sample processing and analysis system 2803 which includes sample preparation sub-system 3002 and the components described herein further including the closed slurry recirculation flow loop 8002 components. The communication unit 2828 may be integrated with the control system 2800 (e.g. controller 2820) or separate from the programmable processing system.

Programmable processing logic 2826 of the control system 2800 which directs the operation of system controller 2820 including one or more processors may process the communications received from the communication unit 2828 or network interface 2815 including agricultural data (e.g., test data, testing results, GPS data, liquid application data, flow rates, etc.), and soil sample processing and analysis systems 2803 generated data. The memory 2805 of control system 2800 is configured for preprogrammed variable or setpoint/baseline values, storing collected data, and computer instructions or programs for execution (e.g. software 2806) used to control operation of the controller 2820. The memory 2805 can store, for example, software components such as testing software for analysis of soil and vegetation samples for performing operations of the present disclosure, or any other software application or module, images 2808 (e.g., captured images of crops), alerts, maps, etc. The system 2800 can also include an audio input/output subsystem (not shown) which may include a microphone and a speaker for, for example, receiving and sending voice commands or for user authentication or authorization (e.g., biometrics).

The system controller 2820 communicates bi-directionally with memory 2805 via communication link 2830, network interface 2815 via communication link 2832, display device 2830 and optionally a second display device 2825 via communication links 2834, 2835, and I/O ports 2829 via communication links 2836. System controller 2820 may further communicate with the soil sample processing and analysis systems 2803 via wired/wireless communication links 5752 either via the network interface 2815 and/or directly as shown.

Display devices 2825 and 2830 can provide visual user interfaces for a user or operator. The display devices may include display controllers. In one embodiment, the display device 2825 is a portable tablet device or computing device with a touchscreen that displays data (e.g., test results of soil, test results of vegetation, liquid application data, captured images, localized view map layer, high definition field maps of as-applied liquid application data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 2830 may be a display (e.g., display provided by an original equipment manufacturer (OEM)) that displays images and data for a localized view map layer, as-applied liquid application data, as-planted or as-harvested data, yield data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

Microfluidic System Modifications

The sections which follow describe various aspects to the foregoing agricultural sample analysis systems and associated devices previously described herein which process and analyze/measure the prepared agricultural sample slurry for analytes of interest (e.g. soil nutrients such as nitrogen, phosphorous, potassium, etc., vegetation, manure, etc.). Specifically, the modifications relate to microfluidic devices and manifolds previously described herein which comprises part of chemical analysis sub-system 3003 of agricultural sampling system 3000 shown in FIG. 1. These microfluidic devices include microfluidic processing disk 4000 and individual analysis processing devices such as processing wedges 4002, and alternative embodiments thereof described below.

FIGS. 22-41 show an alternative embodiment of a microfluidic manifold comprising a polygonal shaped microfluidic manifold slurry processing substrate 5000 for processing agricultural slurry sample. Processing substrate is constructed of a plurality of layers 5001 which may be permanently bonded together via adhesives, thermal/heat bonding, or other fabrication techniques previously described herein. Processing substrate 5000 may generally include the same internal pneumatically-actuated microfluidic devices as previously described herein for processing wedges 4002 such as diaphragm-operated micropumps 5015 including extractant pump 4020, slurry pump 4021, reagent pump 4022, and transfer pump 4023, microvalves 4018, optional micromixing chambers 4024, flow analysis cell 4027, and branched microchannels 4012 fluidly coupling the devices together. The arrangement/layout and fluidic passageways however may be different due to the block-shaped form factor of support structure 5000 in lieu of triangular wedge shape.

It bears noting that the chemical analysis sub-system 3003 is comprised of a plurality of processing substrates 5000 operable in parallel to process and analyze slurry samples simultaneously. In contrast to annular and circular microfluidic processing disk 4000 adapted for use with a centrifuge 3000, the block shape form substrate is amenable for use in any type and configuration of housing in a space efficient manner which may be provided when ultrafine microporous filter 5757 is used to produce the supernatant.

Figure 22:
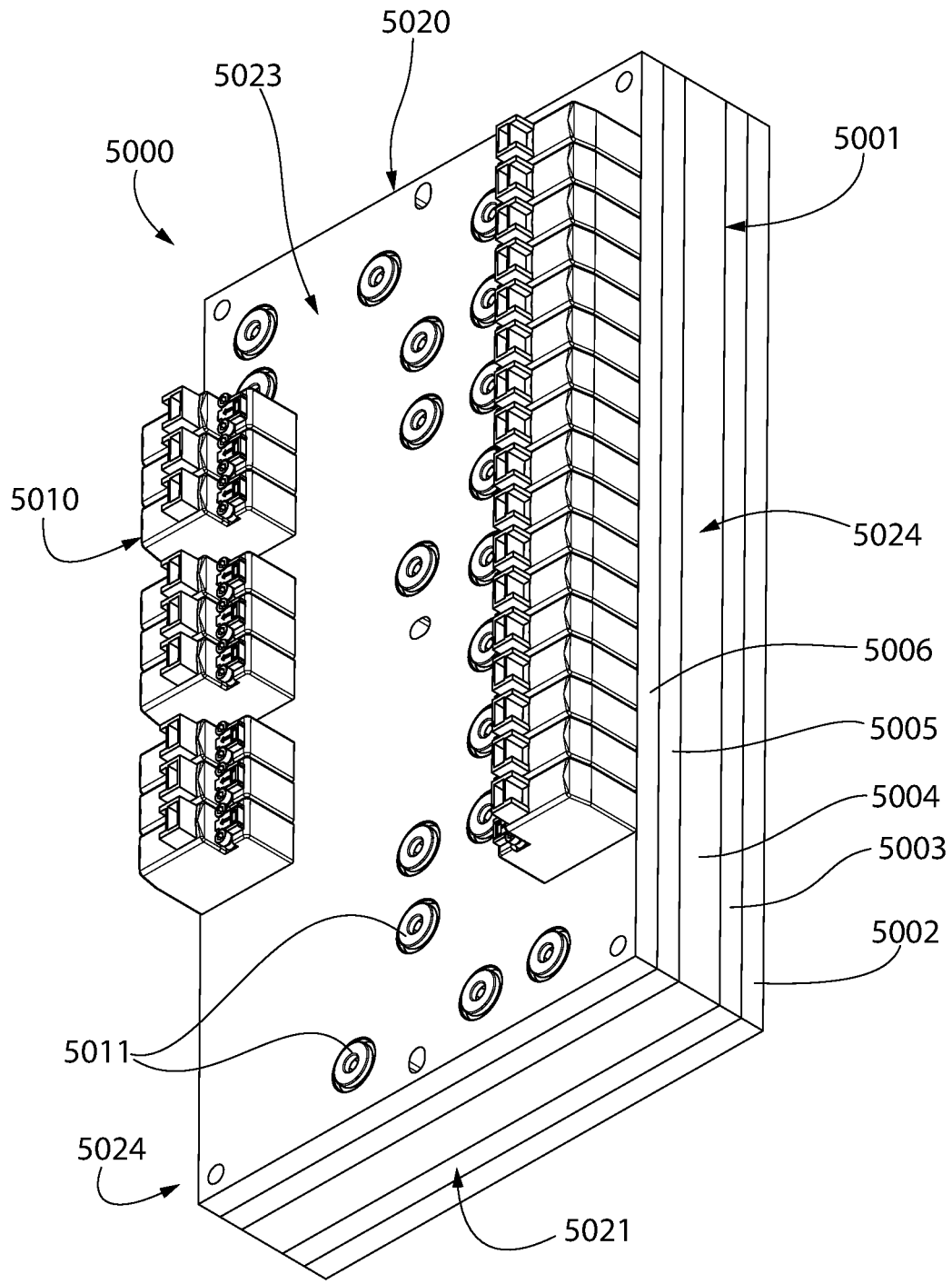
FIG. 22 is a first perspective view of a multi-layered microfluidic manifold slurry processing substrate for processing agricultural slurry sample.
Figure 23:
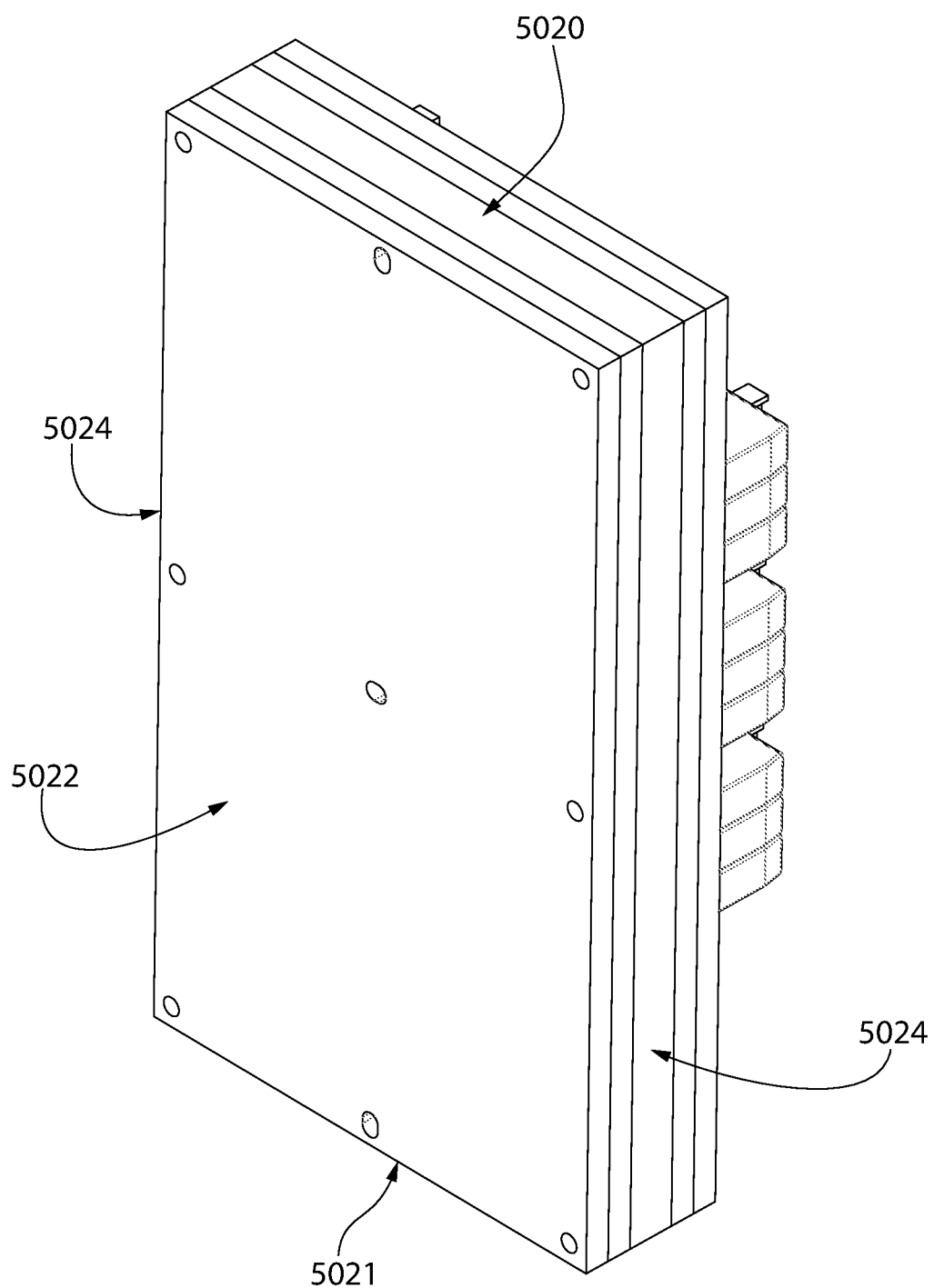
FIG. 23 is a second perspective view thereof.
Figure 24:
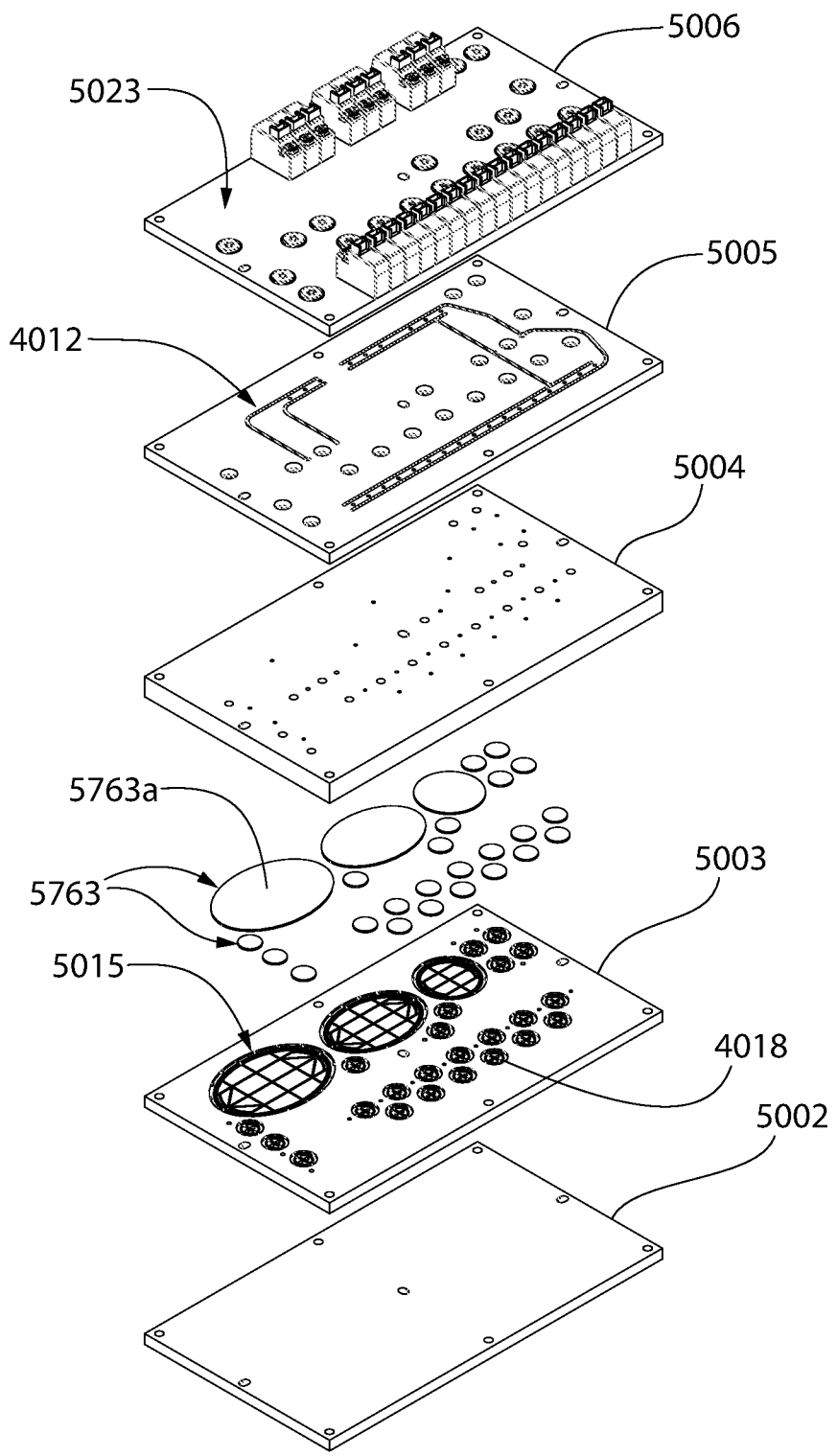
FIG. 24 is a first exploded perspective view thereof.
Figure 25:
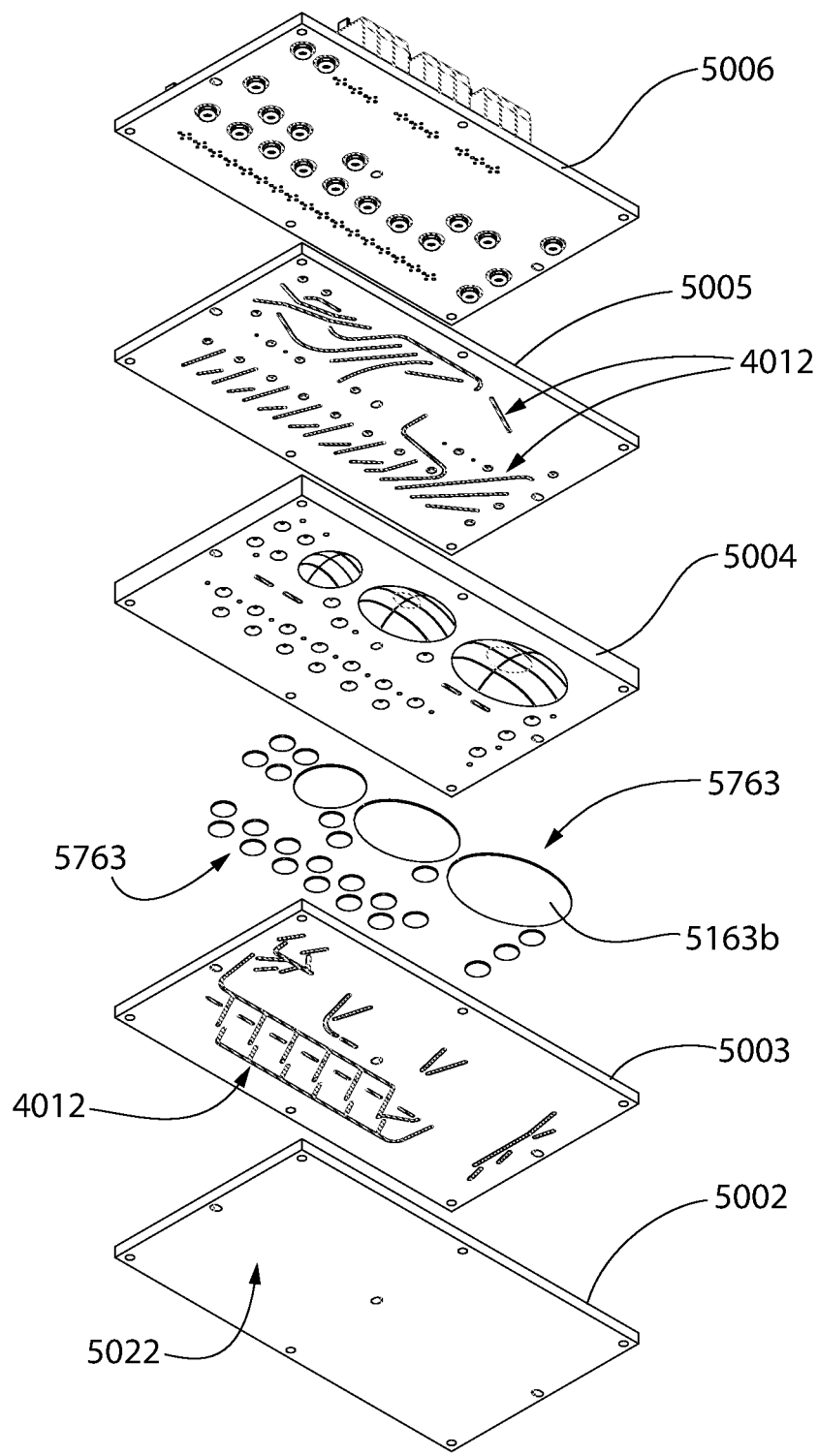
FIG. 25 is a second exploded perspective view thereof.
Figure 26:
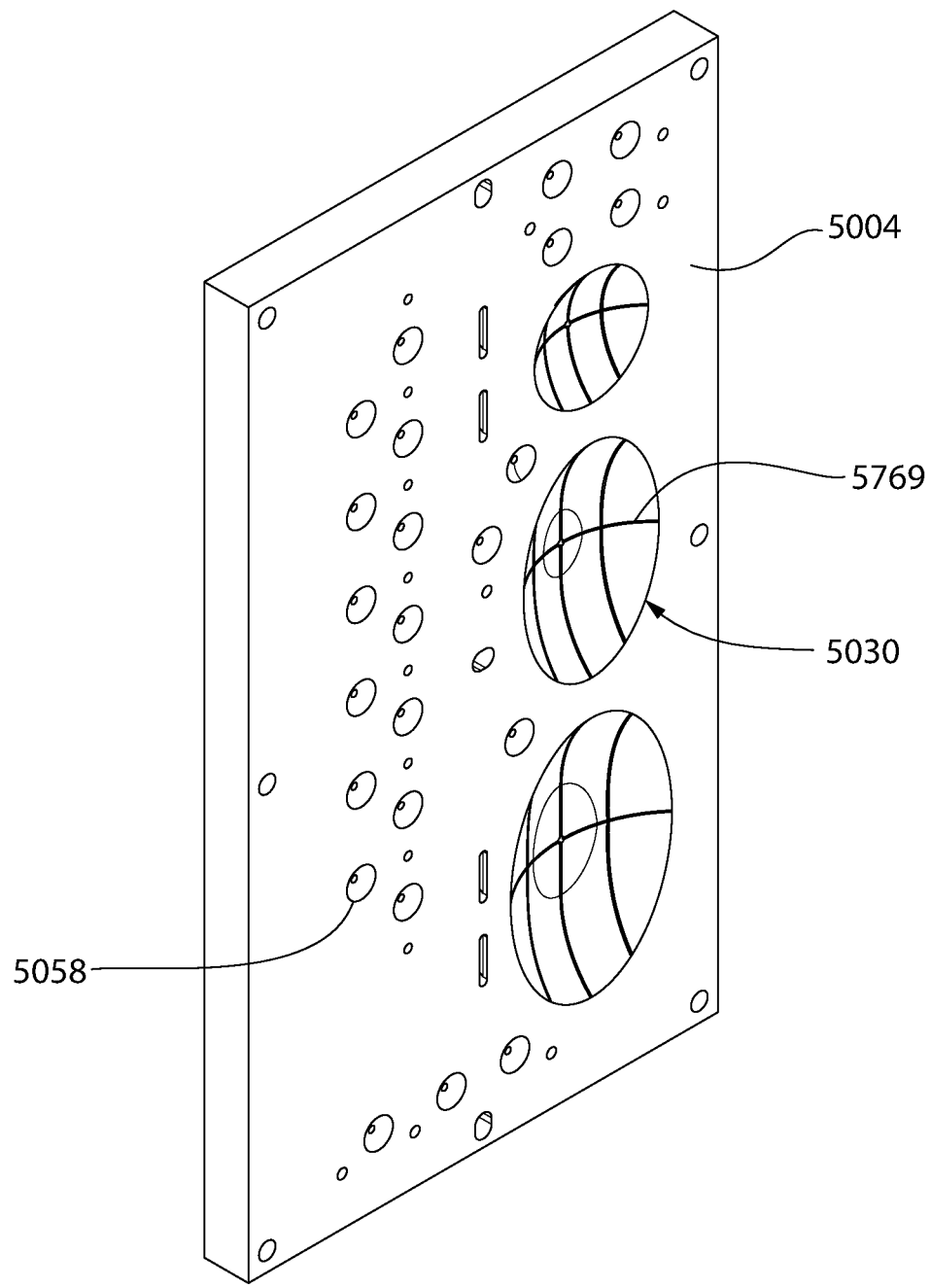
FIG. 26 is a perspective view of an air layer thereof.
Figure 27:
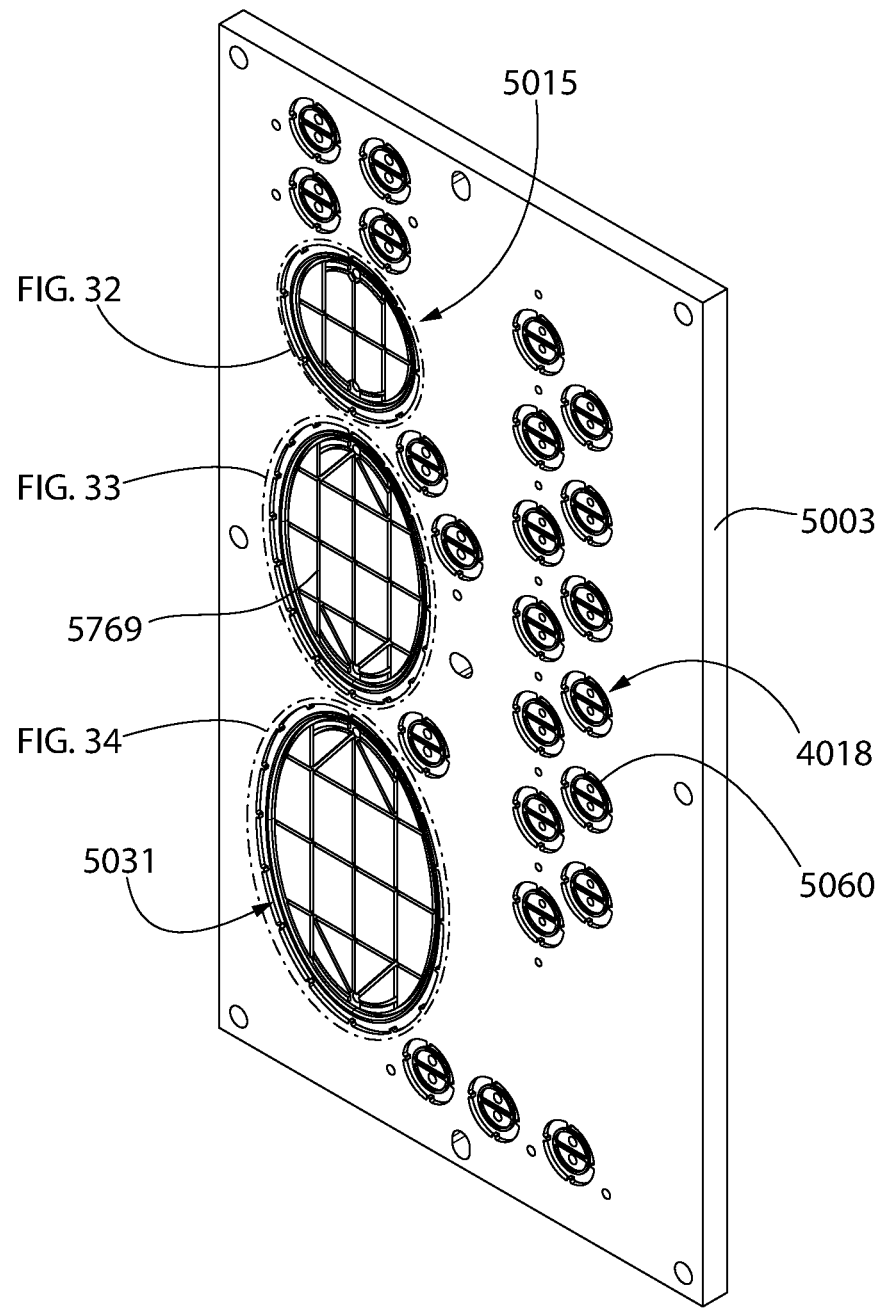
FIG. 27 is a perspective view of the first side of a liquid layer thereof showing a plurality of microfluidic devices for processing the agricultural slurry sample.
Figure 28:
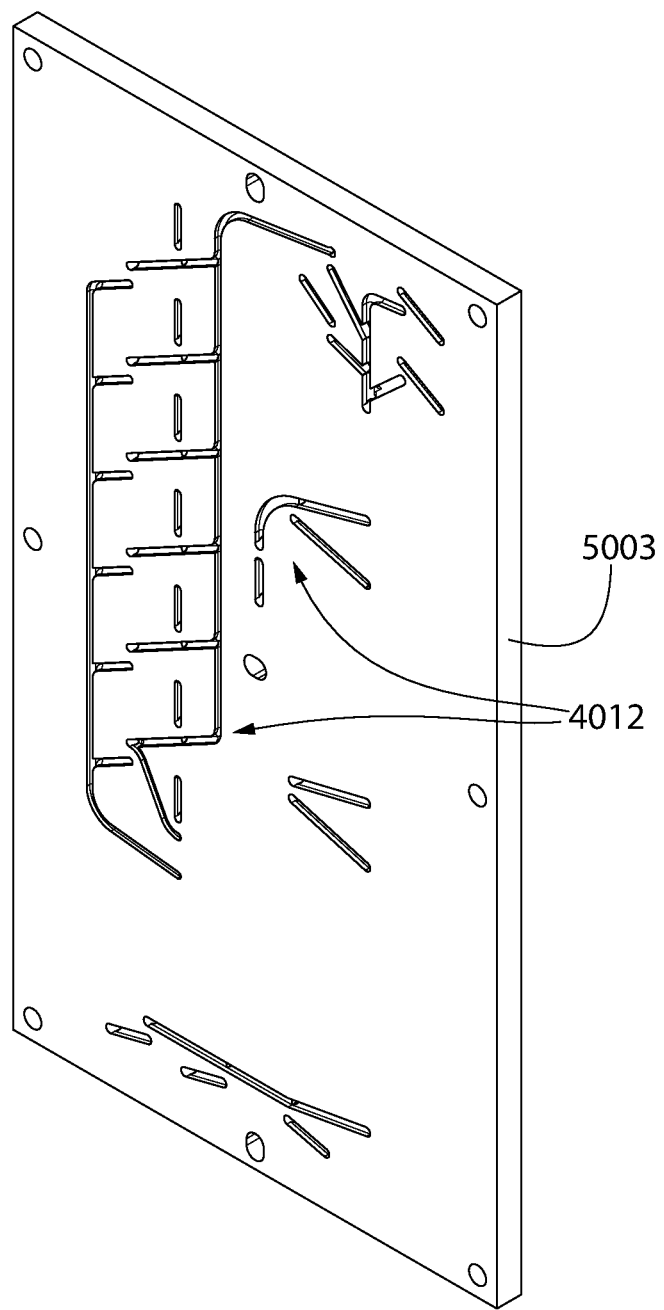
FIG. 28 is a perspective view of the opposite second side of the liquid layer showing a microchannel flow network which is fluidly coupled to the microfluidic devices.
Figure 29:
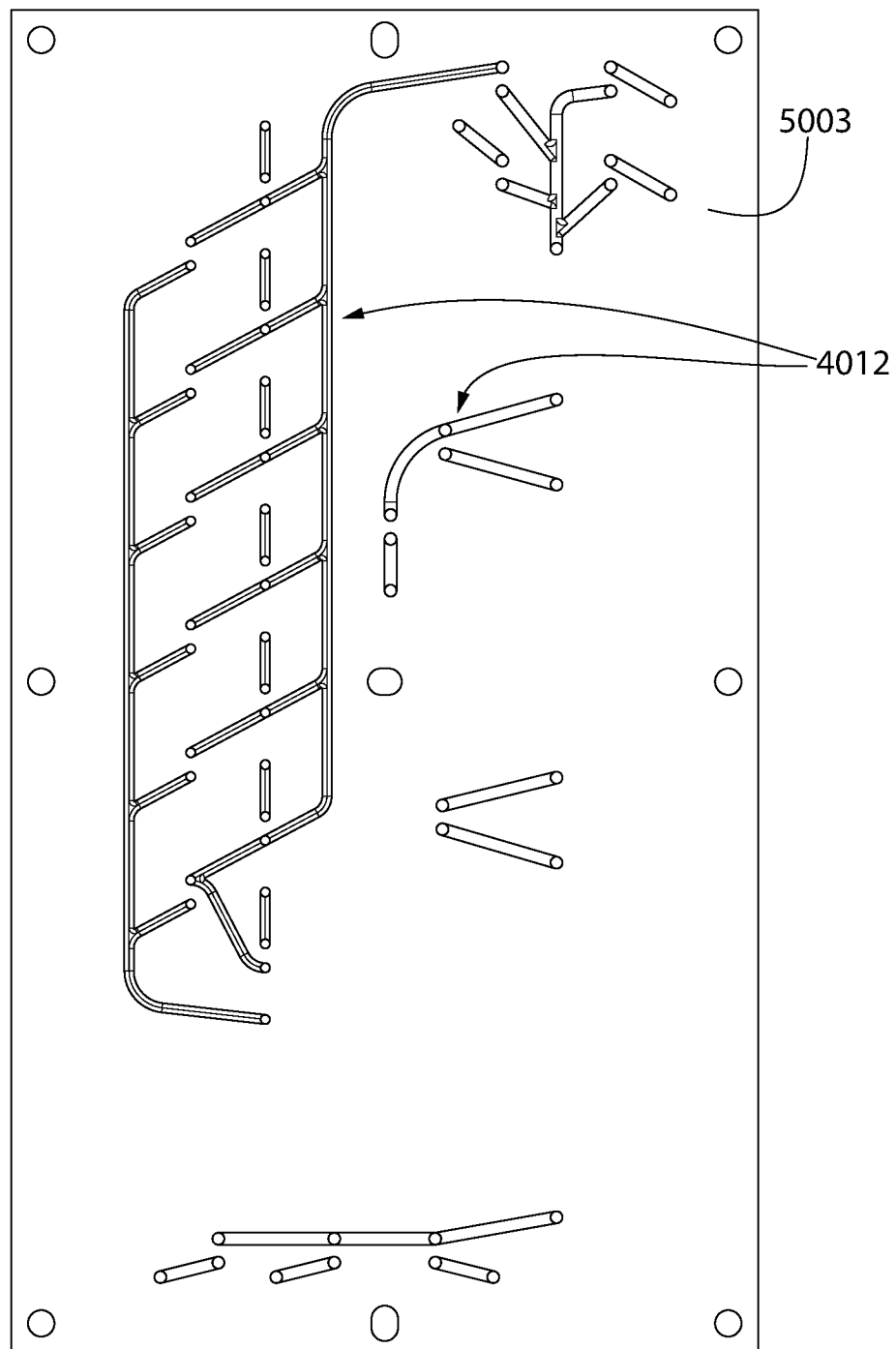
FIG. 29 is a plan view thereof.

Manifold processing substrate 5000 may have a rectangular cuboid configuration in one as shown; however, other polygonal shapes may be used. Substrate 5000 is intended to be used in an upright vertical orientation as shown in FIGS. 22-23 in one implementation for reasons further described herein with respect to slurry flow paths. Other orientations are possible however for operation of the microfluidic manifold processing substrate 5000. Similar to processing wedges 4002 previously described herein, each processing substrate is a standalone slurry analysis device or train which is fluidly isolated from every other processing substrate. This allows each substrate 5000 to process the slurry simultaneously in parallel for different analytes which advantageously decreases processing time and completion of chemical analyses.

A non-limiting example of a five-layer construction of microfluidic manifold processing substrate 5000 is shown recognizing that more of less layers may be provided in other embodiments as needed depending on the type of agricultural slurry processing intended to be performed. In order from the planar outer first major surface or side 5022 to opposite planar outer second major surface or side 5023, the adjacent layers of the packaged processing substrate 5000 include first outer layer 5002, liquid layer 5003 thereon, air layer 5004 thereon, fluid distribution layer 5005 (e.g., air and liquid—extractant, supernatant, slurry, etc.) thereon, and second outer layer 5006 thereon. Outer layer 5002 defines first major side 5022 while opposite outer layer 5006 defines second major side 5023. The remaining layers are inner layers. The substrate further includes top side 5020, opposite bottom side 5021, and pair of opposed lateral sides 5024. Major surfaces or sides 5022, 5023 have a greater surface area than other sides of substrate 5000.

Outer layer 5006 includes a plurality of quick-connect liquid fittings 5011 and quick connect air valves 5010. Liquid fittings 5011 are configured for detachable connection to liquid tubing from various liquid sources used in microfluidic manifold substrate 5000 (e.g., extractant, cleaning/flushing water, calibration standard liquid, etc.). Air valves 5010 are configured for detachable connection to air tubing for applying pneumatic pressure signals or vacuum signals to the microfluidic devices embedded in substrate 5000.

Fluid distribution layer 5005 is adjacent outer layer 5006 and includes a plurality of both fluidly separate and/or interconnected microchannels 4012 for transferring the air and liquids from their applicable sources via fittings 5010, 5011 to the and in turn the microfluidic devices (e.g., microvalves 4018 and micropumps 5015 in microfluidic manifold substrate 5000 seen in the flow diagram of FIGS. 2-3). Each micropump 5015 and microvalve 4018 comprises an individual thin and resiliently deformable elastomeric diaphragm 5763 having an elastic memory. The diaphragms are sandwiched and trapped between liquid layer 5003 and air layer 5004 when the processing substrate 5000 is fully assembled compressing the plural layers together.

Figure 30:
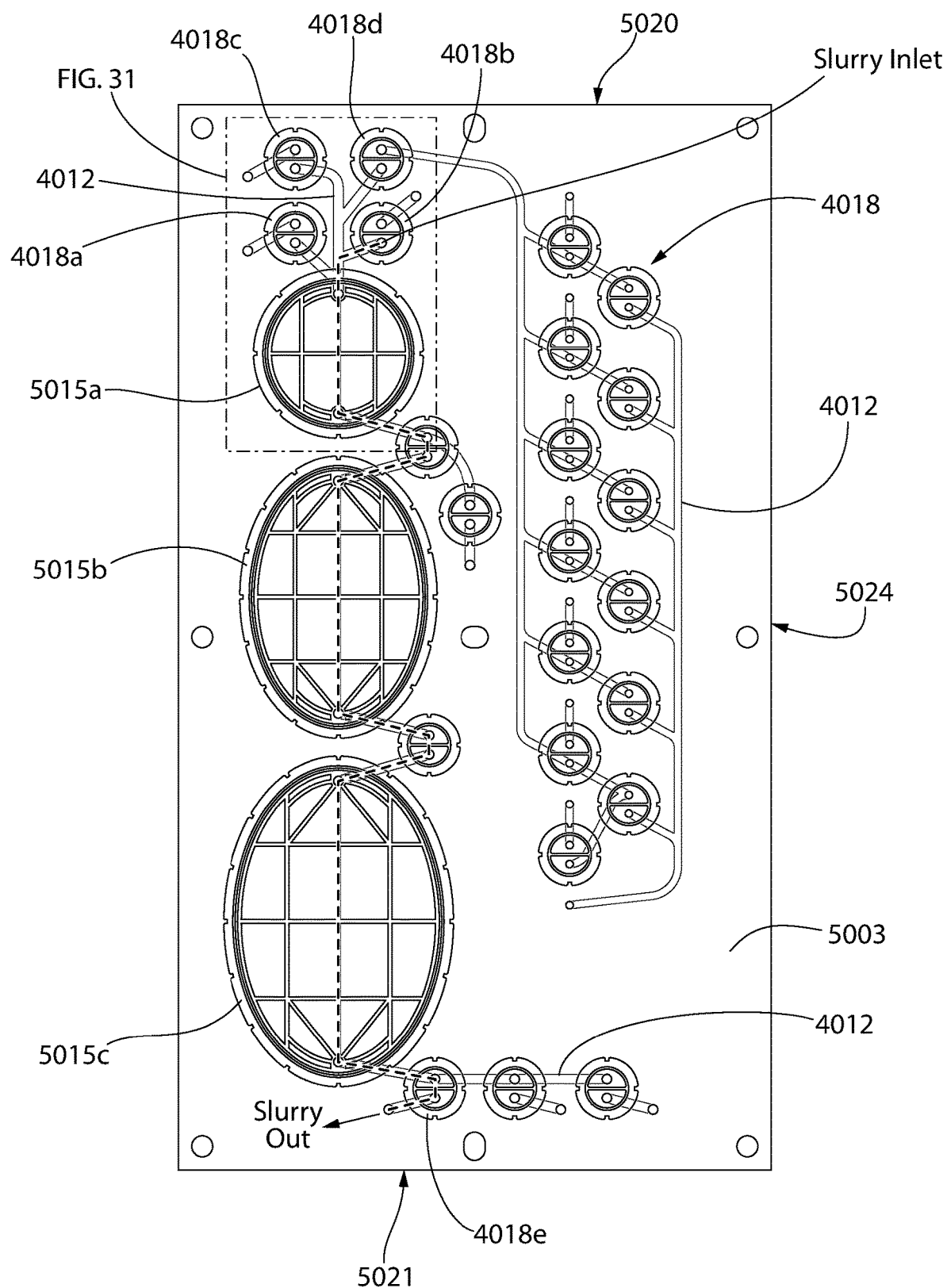
FIG. 30 is a plan view of the first side of the liquid layer showing the microfluidic flow network superimposed to show fluidly connections between the microfluidic devices.
Figure 31:
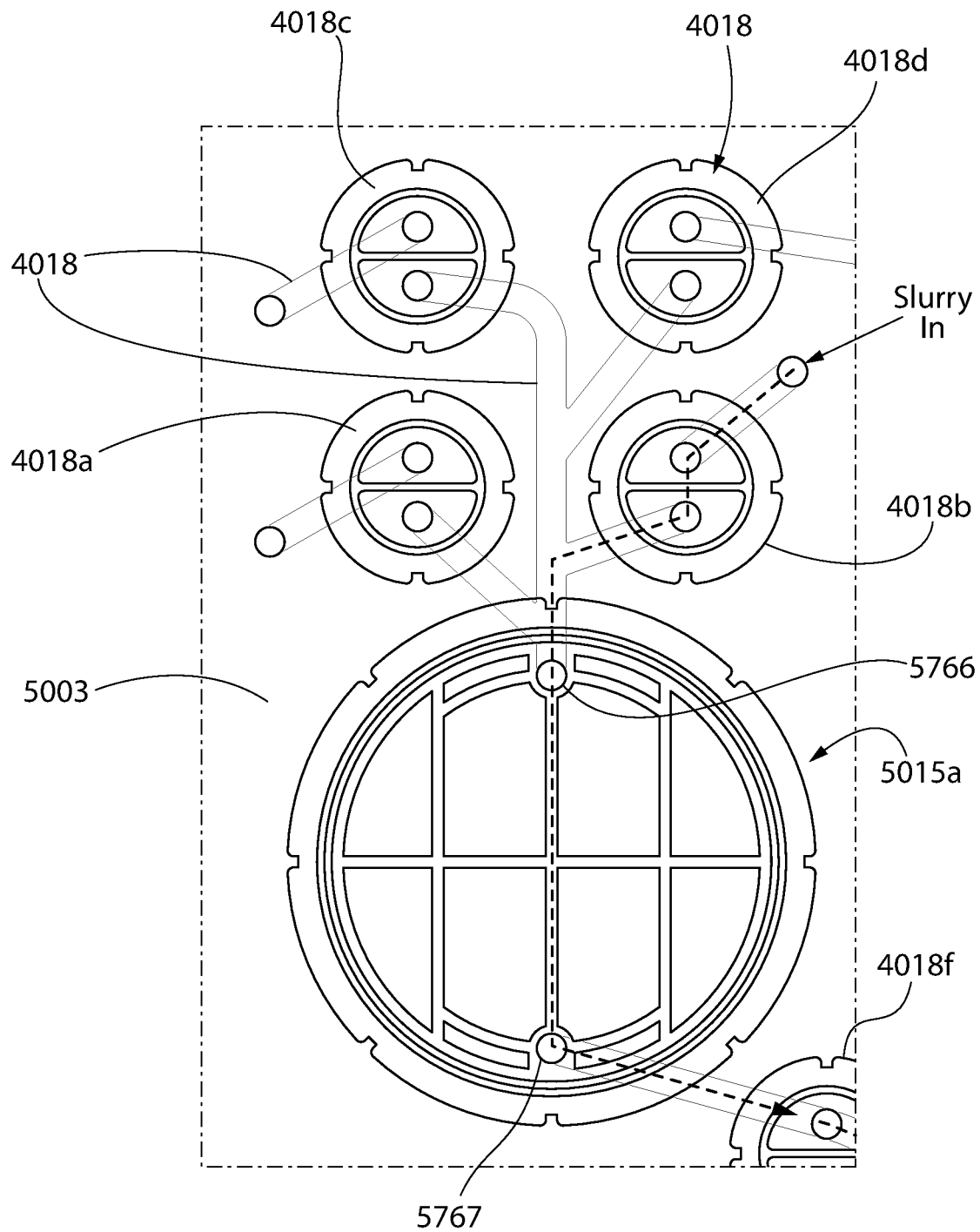
FIG. 31 is an enlarged detail taken from FIG. 30.
Figure 32:
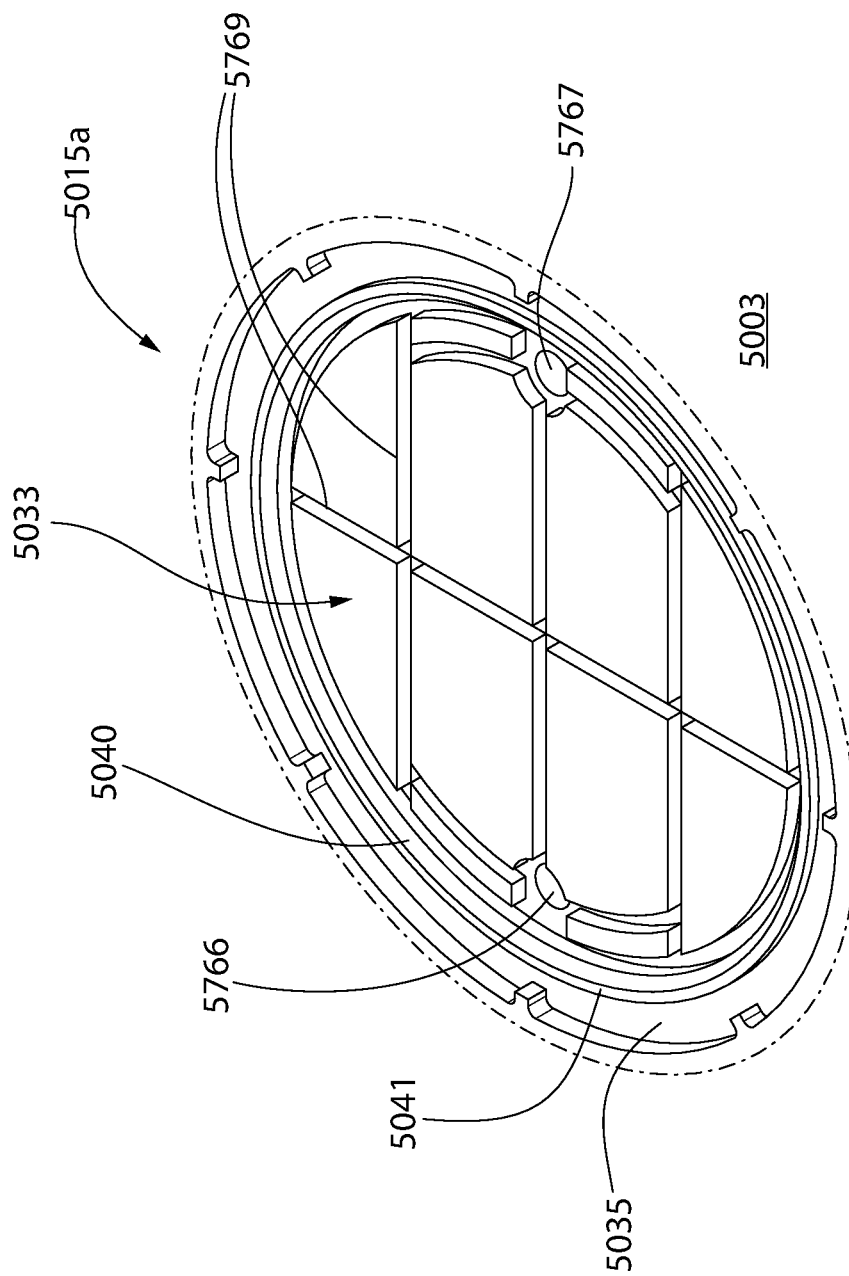
FIG. 32 is a perspective view of a microfluidic device comprising a first micropump formed in part by the liquid layer.
Figure 33:
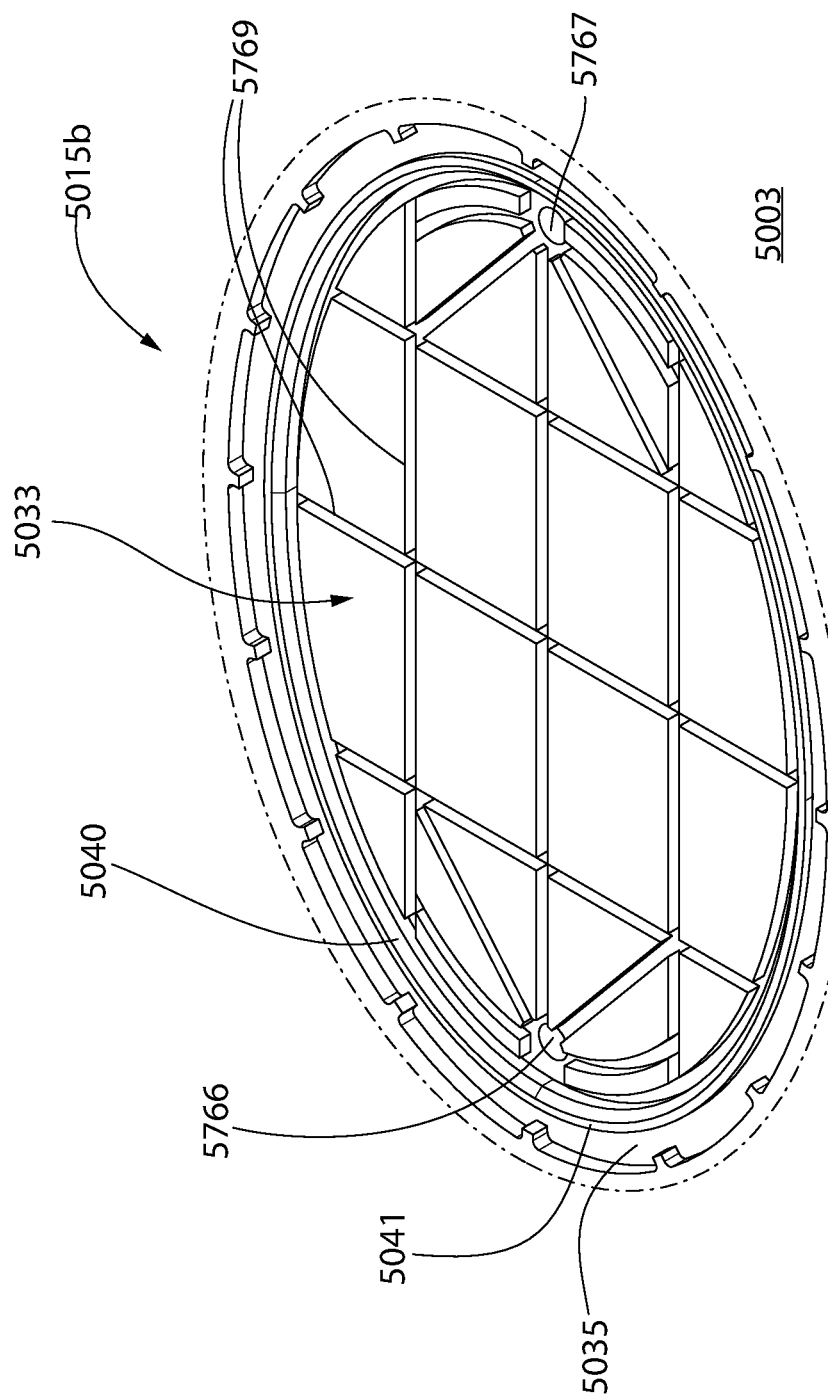
FIG. 33 is a perspective view of a microfluidic device comprising a second micropump formed in part by the liquid layer.
Figure 34:
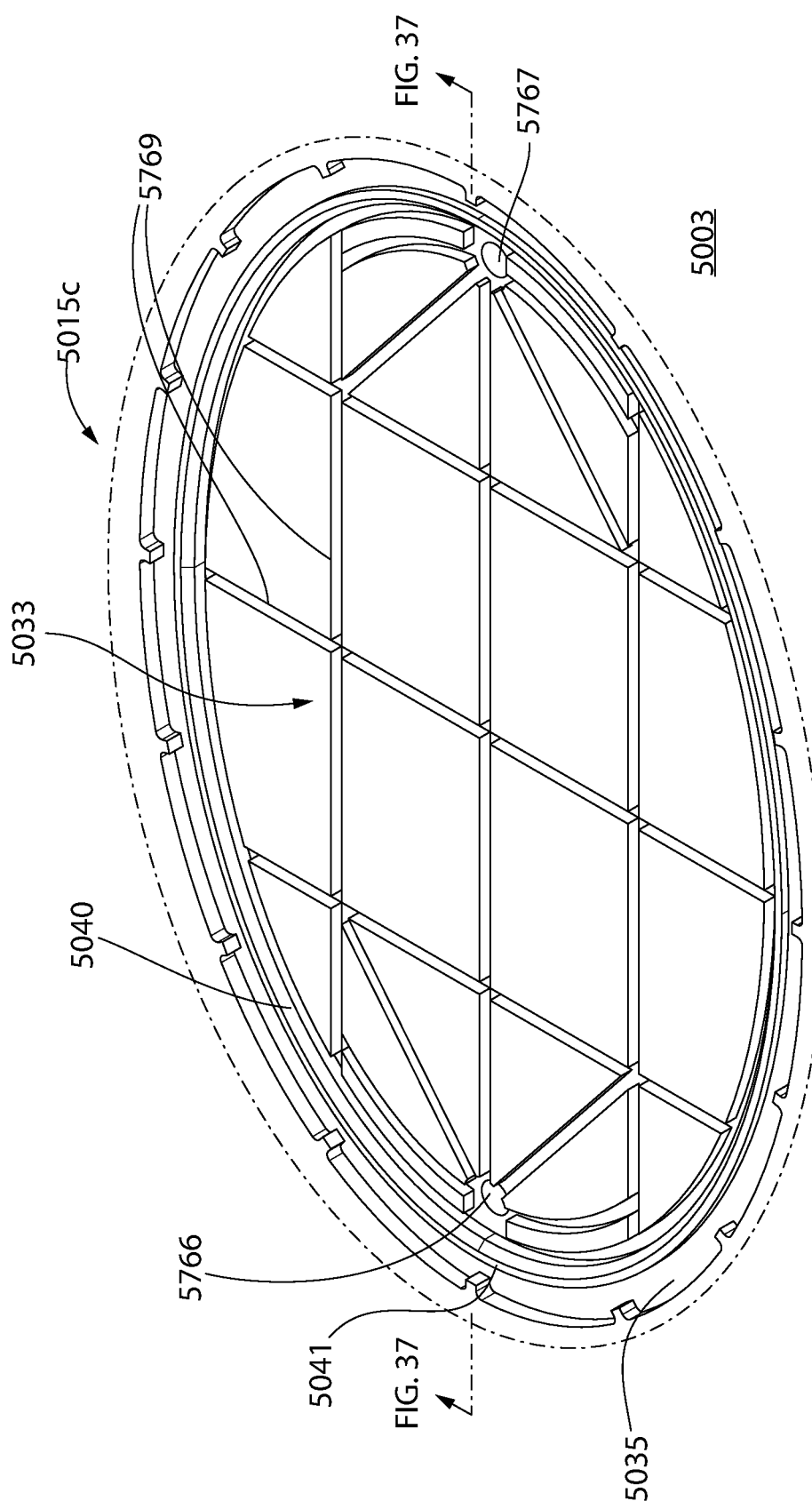
FIG. 34 is a perspective view of a microfluidic device comprising a third micropump formed in part by the liquid layer.

The underside of liquid layer 5003 comprises a plurality of microchannels 4012 which fluidly couple the microvalves 4018 and micropumps 5015 together. FIGS. 30-31 show the fluid interconnections between these microfluidic devices/components formed by the microchannels 4012. In one non-limiting embodiment, the devices and microchannels of the analysis processing substrates 5000 may be configured for mixing extractant with slurry to extract the analyte of interest for further chemical analysis processing to quantify the concentration of analyte (e.g., soil nutrients or other) and chemical properties such as pH and/or Bph. Substrate 5000 may have other used in the processing and analysis of the agricultural slurry. One non-limiting preferred vertical orientation of processing substrate 5000 for operation is shown in FIGS. 30-31.

The micropumps 5015 may include a group of three fluidly interconnected micropumps including first micropump 5015a, second micropump 5015b, and third micropump 5015c in one embodiment as shown. Micropumps 5015 are generally similar in construction and operation to pneumatically actuated micropumps 5760 previously described herein. Each micropump 5015 is a sandwiched structure including an air layer 5004, adjacent liquid layer 5003, and thin resiliently deformable diaphragm 5763 having an elastic memory and defining opposing top and bottom surfaces 5763a, 5763b.

In contrast to micropumps 5760, the present micropumps 5015 (which collectively refers to each of micropumps 5015a-5015c) includes a pump chamber 5037 collectively formed in one embodiment by concavely shaped air-side recess 5030 formed in the portion the air layer 5004 facing diaphragm 5763, and a liquid-side recess 5031 formed in liquid layer 5003. This arrangement is opposite to micropumps 5760. The inventors have discovered that with respect to the prior micropump 5760 design, there is a certain amount of air pressure required to deform the flat diaphragm into the concavity, followed by an additional amount of air pressure required to seal the diaphragm enough to prevent fluid flow through a valve when in the closed position. By inverting the design, the pressure advantageously required to effectively seal the valves when closed is less as the diaphragm is not forced to deform and stretch into the concavity prior to sealing. Recess 5031 is arranged directly opposing and vertically aligned with the air-side recess 5030. Liquid-side recess 5031 may have a circumferentially-extending peripheral sidewall 5032 extending perimetrically around the chamber and a flat base wall defining a flat top surface 5033 on which the diaphragm becomes engaged and seated during the pumping stroke. A flat-to-flat interface is formed between diaphragm 5763 and top surface 5033 during the pumping stroke. Air-side recess 5030 may include domed arcuately curved walls 5034 extending from side to side and circumferentially around the chamber to define the concavity. The curved sidewall surfaces ensure that the diaphragm 5763 does not tear or crack when actuated over multiple operating cycles. It bears noting that the air-side recess 5030 defines the volumetric pumping capacity of the micropump which is expelled with each diaphragm actuation of the micropump.

Air layer 5004 includes pneumatic air pressure signal port 5768 which in fluid communication with the air-side recess 5030 for pressuring the chamber and actuating the micropump 5015 during the slurry intake and discharge pumping stroke. Liquid layer 5003 includes fluid inlet port 5766 and fluid outlet port 5767 which are in fluid communication with the liquid-side recess 5031 for introducing and discharging fluids such as the slurry, extractant, flushing water, calibration standard liquids, etc. Similarly to micropump 5760 previously described herein, the inlet and outlet ports are formed at diametrically opposite ends of the recess 5031.

In the present embodiment, micropumps 5015 also include anti-stall grooves 5769 recessed into the wall surfaces of both the air-side and liquid-side recesses 5030 and 5031. The grooves in the air-side recess may be shallower in depth than those in the liquid-side recess. As previously noted herein, the anti-stall grooves 5769 are configured to prevent adherence of the diaphragm 5763 to the pump chambers 5030, 5031 during operation of the pump. This advantageously allows the diaphragm 5763 to fully and reliably displace substantially the entire volumetric fluid contents of the liquid-side chamber with each pumping cycle, thereby ensuring accuracy of the amount of fluid dispensed and ultimate soil slurry analysis. The anti-stall grooves 5769 may be generally patterned in a two-directional perpendicularly intersecting rectilinear grid array of grooves as shown as previously described herein in relation to micropump 5760.

In one embodiment, it bears noting that the anti-stall grooves 5769 intersect both the perimeter flow groove 5040 and fluid inlet and outlet ports 5766, 5767 to better flush the slurry through and out of the micropumps 5015 during the discharge pumping stroke to prevent particulate retention and accumulations in the liquid-side recess 5031.

Structurally, the present micropumps 5015 may further include two additional features including a perimeter flow groove 5040 and wide-base diaphragm seal ring 5041 (see, e.g. FIGS. 31-36. The perimeter flow groove facilitates handling slurries such as soil slurries which contain a heavy particulate or solids content within the microfluidic manifold formed by processing substrates 5000. During testing, the inventors observed that the area of lowest diaphragm physical displacement/movement and tight clearance around the perimeter of the diaphragms can be a place for the slurry particulates to become lodged. (e.g., sand-like particles). This may adversely affect proper operation and full volumetric pumping capacity with each pumping stroke. Adding the perimeter flow groove on the liquid side of each pump creates a large open cross sectional area which promotes flow in these otherwise tight areas. This advantageously continually flushes out the peripheral portions of the liquid-side recess 5031 with each pump stroke to prevent particulate and sediment buildup around the perimeter of the chamber.

Figure 36:
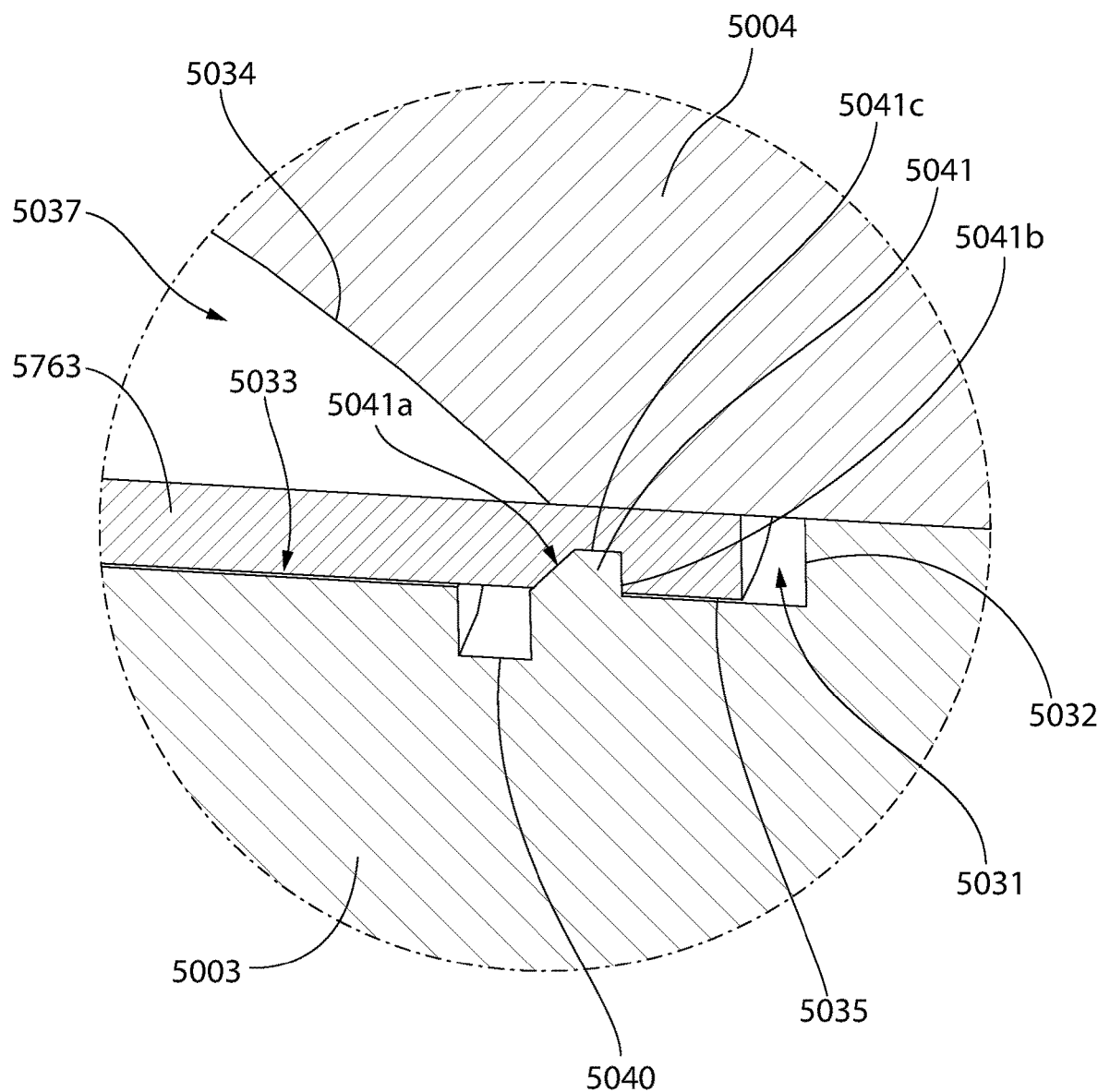
FIG. 36 is an enlarged partial cross-sectional perspective view of the first micropump showing the first embodiment of the diaphragm seal ring in greater detail.
Figure 37:
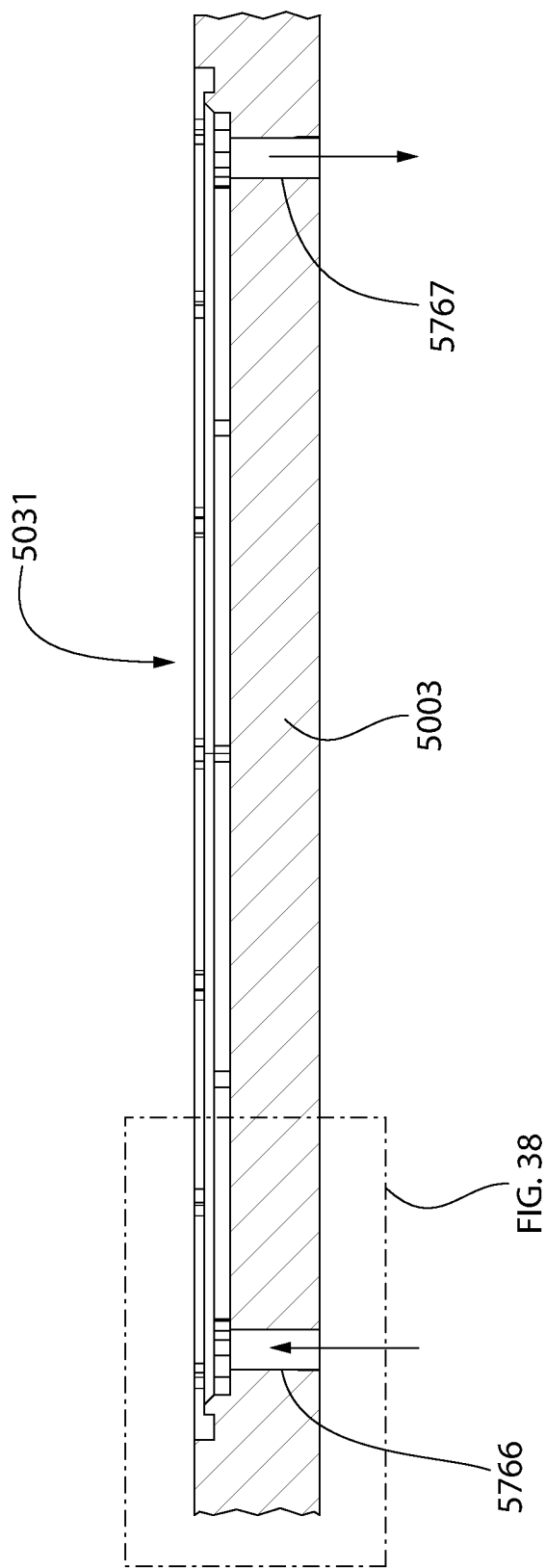
FIG. 37 is a cross-sectional view of the third micropump taken through the liquid layer and the fluid inlet and outlet ports of the micropump.
Figure 38:
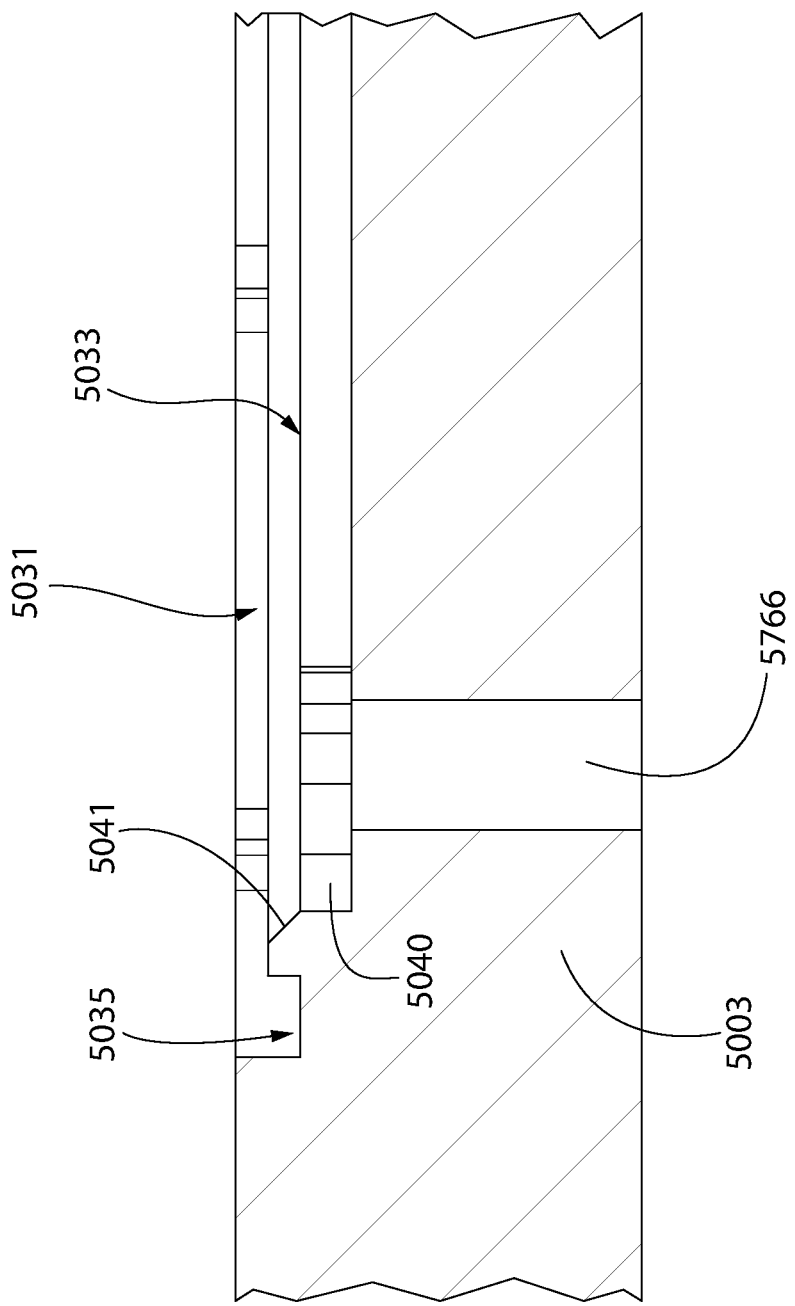
FIG. 38 is an enlarged detail taken from FIG. 37.

Perimeter flow groove 5040 may be a continuous open structure which extends around the entire circumference and perimeter of the liquid-side recess 5031. In one embodiment, the flow groove may have a rectilinear (rectangular or square) transverse cross-sectional shape as best shown in FIG. 36. Flow groove 5040 may be inset from and inwardly spaced apart from peripheral sidewall 5032 and recessed into the flat top surface 5033 of the recess 5031.

The wide-base diaphragm seal ring 5041 functions to prevent the elastomeric pump diaphragm 5763 from plugging the perimeter flow groove 5040 when the diaphragm is sandwiched between the pumping and air layers 5003, 5004 as the layers of the analysis processing substrate 5000 are compressed and sealed together during assembly. The inventors discovered that once the flow groove was implemented, a problem was encountered with the peripheral portion of the diaphragm 5763 creeping down into the flow groove 5040 due deformation of the diaphragm during the high temperatures encountered in the manifold fabrication process necessary to bond the layers of processing substrate together. This caused the diaphragm to "cave" into the perimeter flow groove 5040 which results in two problems: (1) obstruction of the perimeter flow grooves, allowing particulate to become trapped at the perimeter of the micropump; and (2) inadequate retention of the diaphragm in its peripheral sealing pocket 5035 formed adjacent sidewall 5032 and recessed into liquid layer 5003 in the liquid-side recess 5031. This latter condition can lead to the diaphragm pulling out of its sealing pocket thereby adversely creating a leak path between the pneumatic and liquid sides of the micropump 5015. The manifold processing substrate 5000 is no longer functional at this point due to the leakage path.

To overcome the foregoing problems, perimetrically extending seal ring 5041 is provided which prevents ingress of the peripheral region of the diaphragm 5763 into the perimeter flow groove 5040 to keep it clear for flushing slurry sediment/particulate during pumping (see e.g. FIG. 36). In one preferred but non-limiting embodiment, seal ring 5041 is disposed outboard of and immediately adjacent to the flow groove 5040. Seal ring is a raised protrusion which projects upwards from top surface 5033 of the liquid-side recess 5031 to support the diaphragm at the location adjacent to the groove 5040, thereby preventing creep into the groove.

Figure 35A:
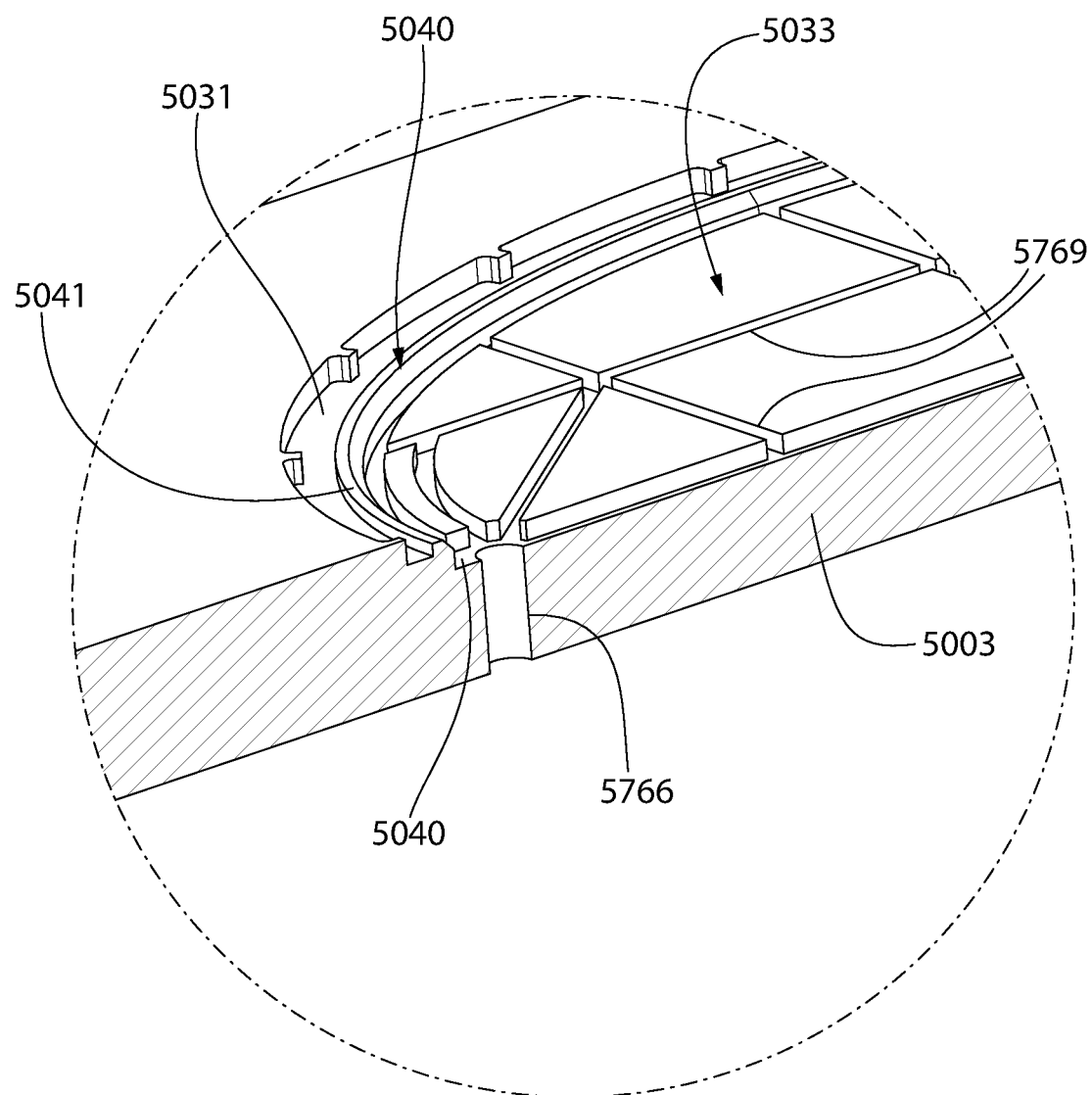
FIG. 35A is a cross-sectional perspective view taken through the fluid inlet port of any of the first, second, or third micropumps showing a perimeter flow groove, diaphragm sealing ring, and anti-stall grooves of the pump chamber.
Figure 35B:
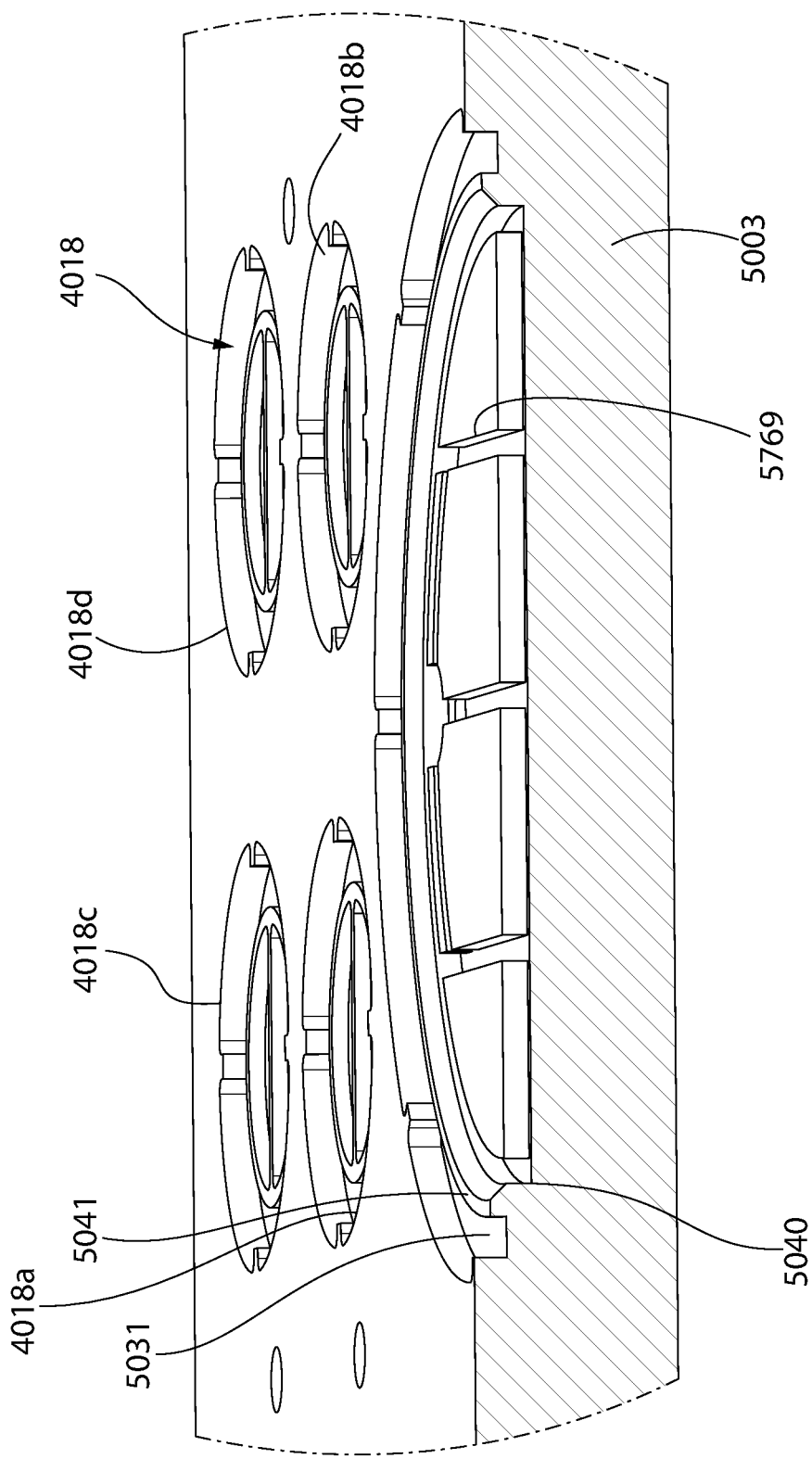
FIG. 35B is a cross-sectional perspective view of the first micropump showing a first embodiment of the diaphragm seal ring.
Figure 35C:
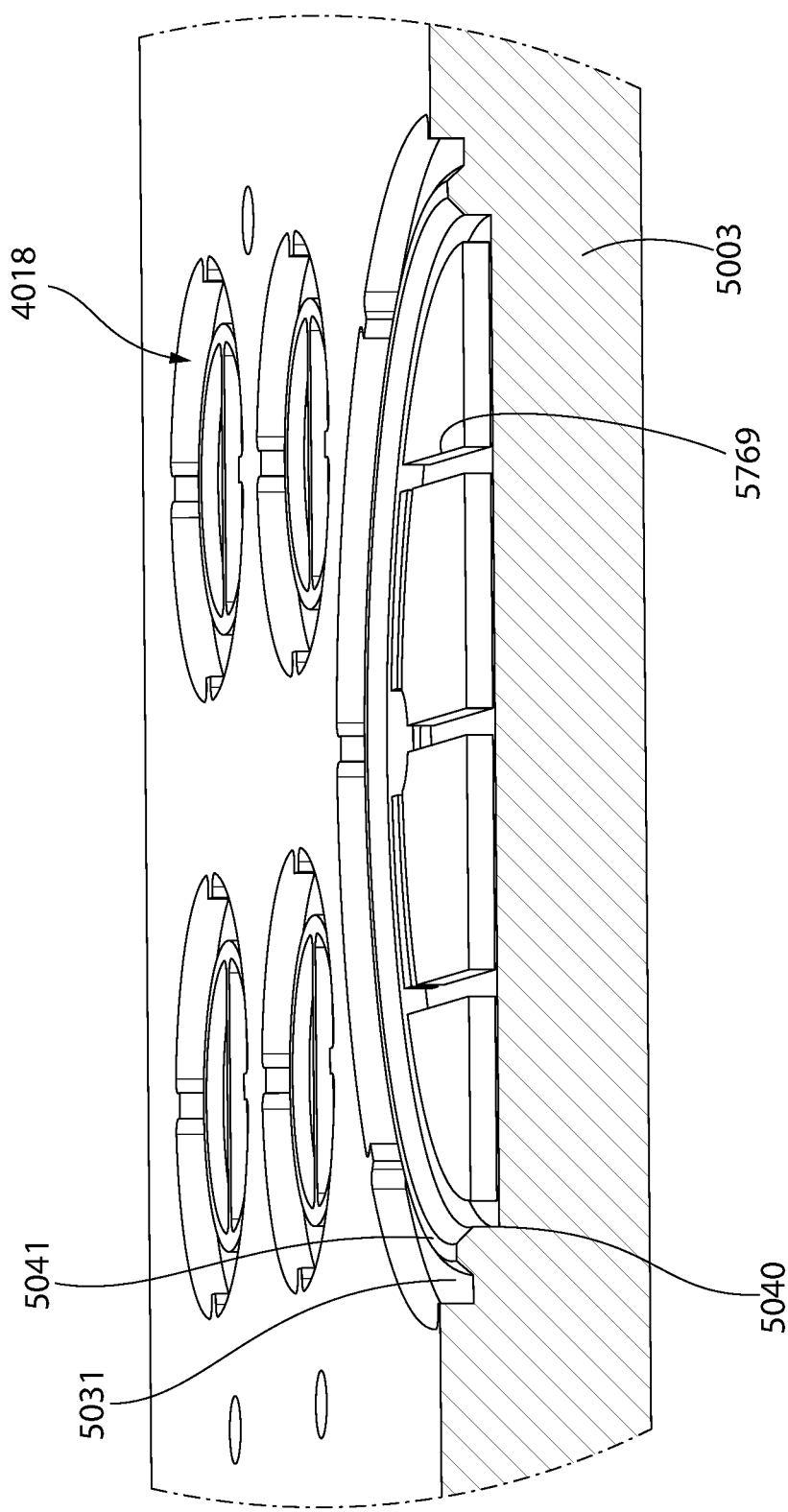
FIG. 35C is a cross-sectional perspective view of the first micropump showing a second embodiment of the diaphragm seal ring.

In one embodiment, seal ring 5041 preferably has a wider base 5041*b* than a terminal top end portion 5041*c* terminated and formed by one or more obliquely angled surfaces 5041*a*. The inventors discovered that the narrower top end portion helps penetrate the diaphragm 5763 to a greater degree than a broad top end. This readily pinches and deforms the diaphragm in the area adjacent to flow groove 5040 which precludes creep and incursion into the groove when liquid layer 5003 is compressed against and thermally bonded to opposing air layer 5004. In addition, the seal ring 5041 ensures proper positioning of the peripheral portions or regions of the diaphragm into its circumferentially extending retention pocket 5035. FIGS. 35A-B and 36 shows an embodiment of seal ring 5041 have a single angled surface 5041*a* forming a partial trapezoidal shaped ring in cross-section. In other embodiments, opposing angled surfaces 5041*a* may be provided forming a full trapezoidal shaped ring in cross-section (see, e.g. FIG. 35C). The angles surface(s) 5041*a* create a cross-sectional profile of the seal ring 5041 which is narrower at top than at the base.

Figure 39:
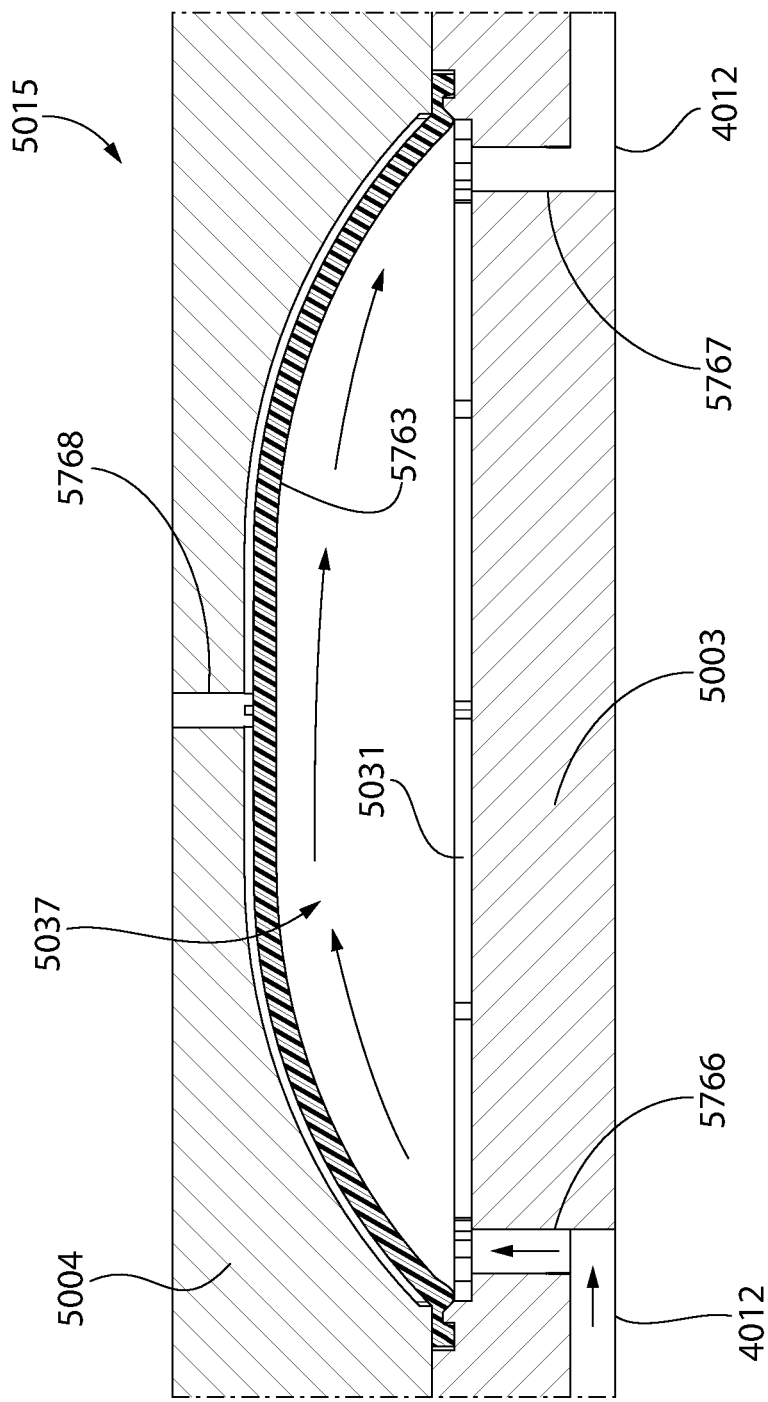
FIG. 39 is a first cross-sectional view of one of the micropumps showing the micropump in the fill or intake stroke of the pump during operation.
Figure 40:
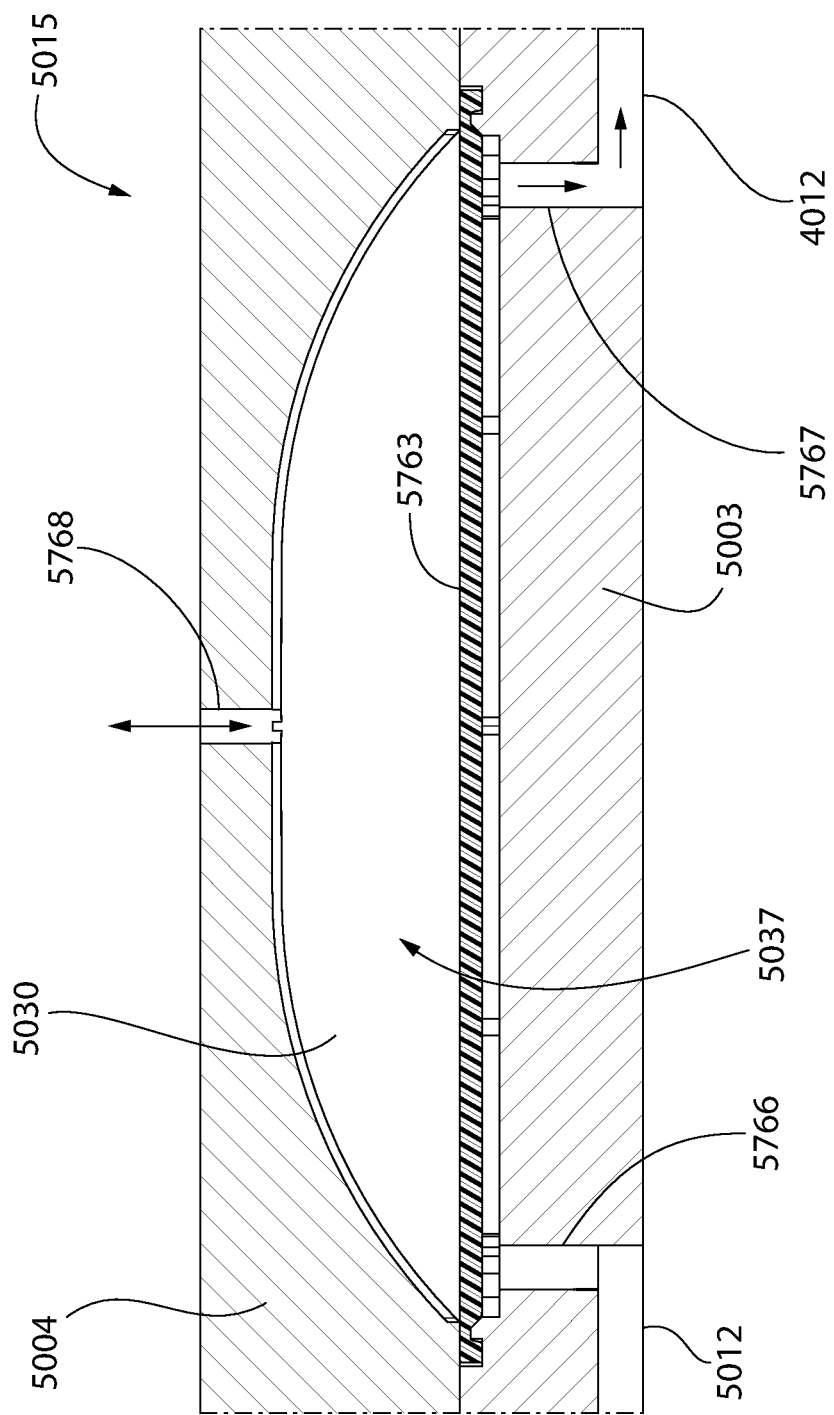
FIG. 40 is a second cross-sectional view thereof showing the micropump in the discharge stroke of the pump during operation.
Figure 41:
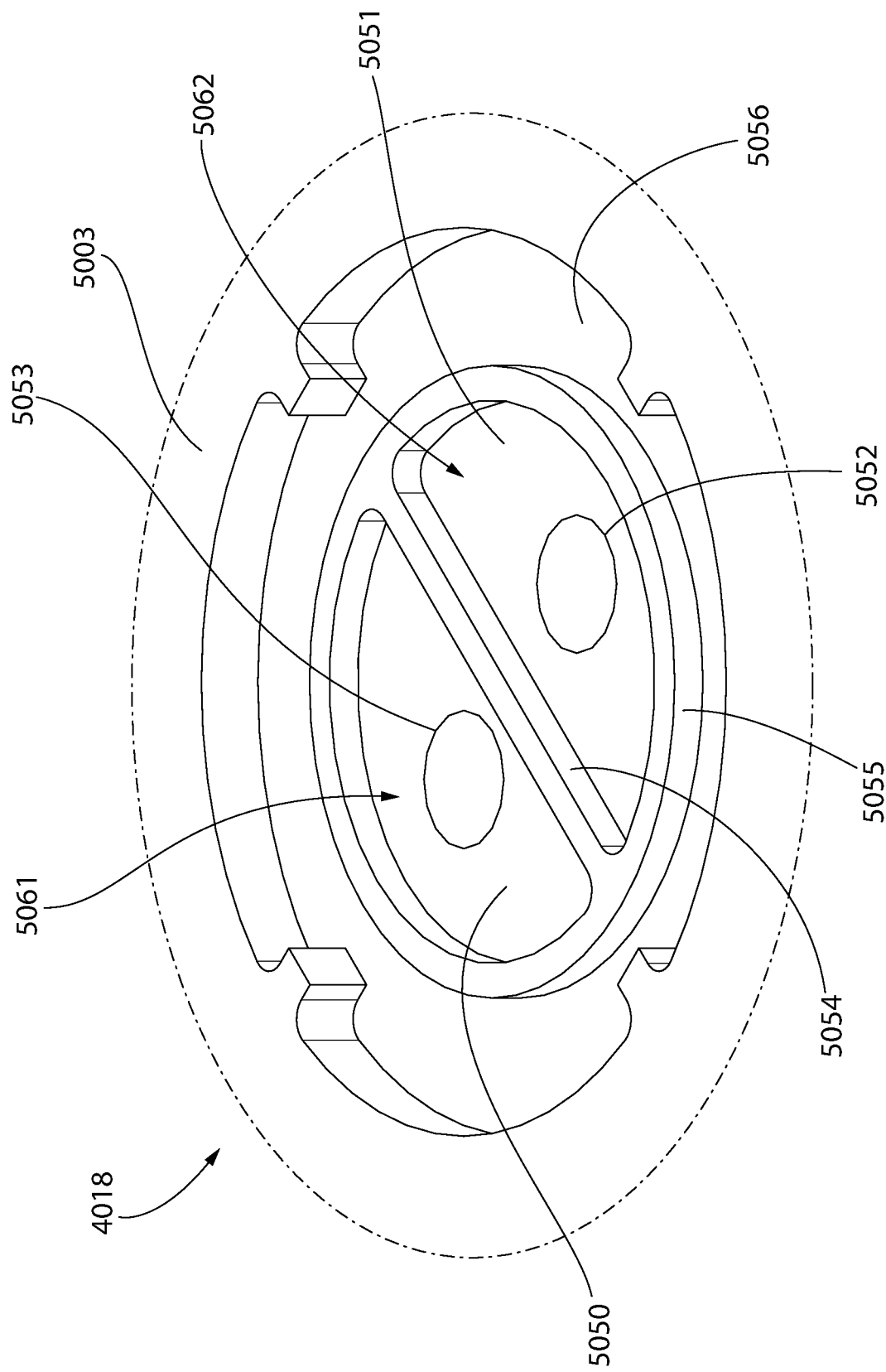
FIG. 41 is a perspective view another microfluidic device comprising a microvalve formed in part in the liquid layer.
Figure 42:
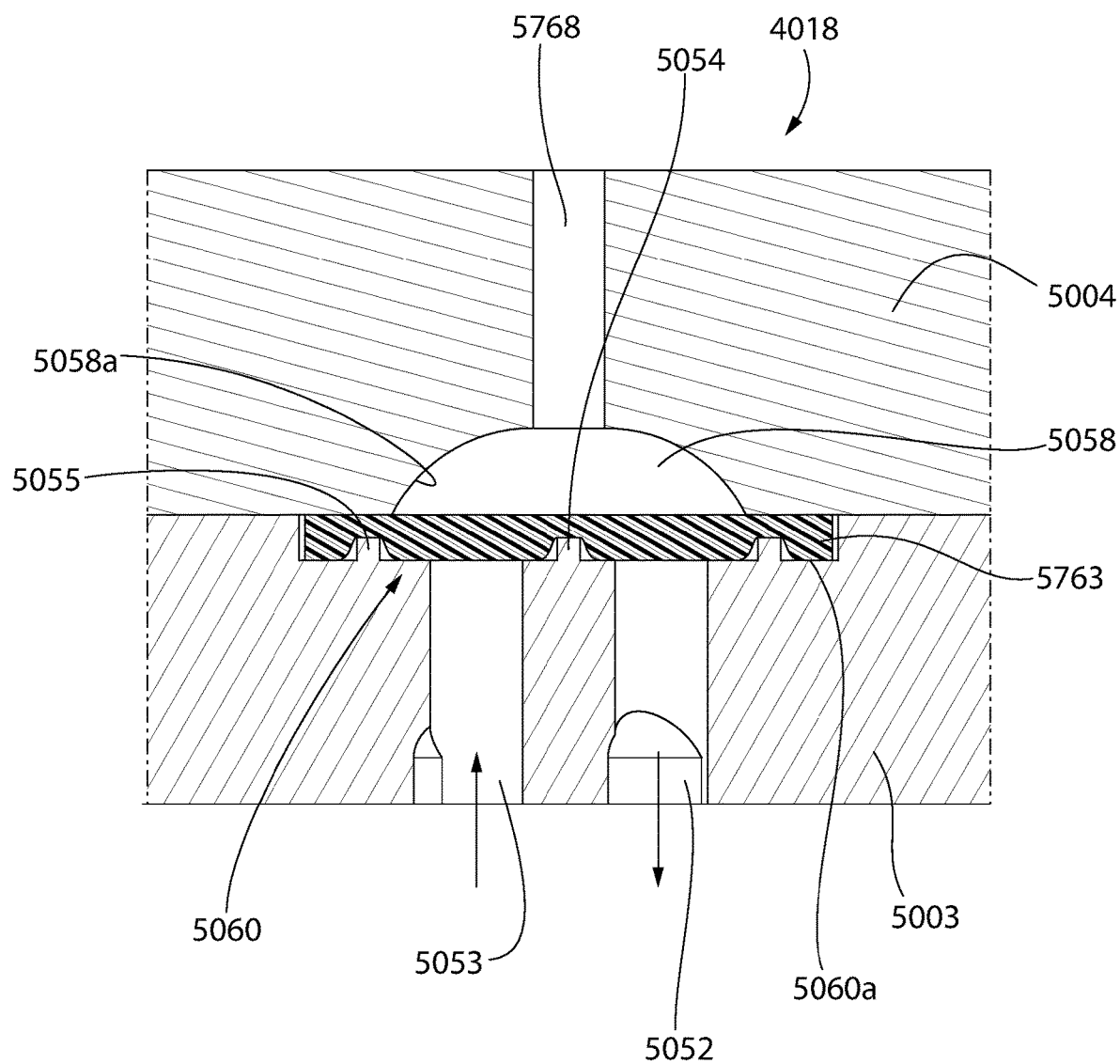
FIG. 42 is a cross-sectional view of the fully assembled microvalve embedded between the liquid layer and an air layer of the microfluidic manifold.

FIGS. 39 and 40 shows one of micropumps 5015 in operation for pumping a liquid such as agricultural slurry or other process liquid through the microfluidic manifold processing substrate 5000. The method of operation will be briefly described. FIG. 39 shows micropump 5015 during the fill or intake stroke. A vacuum is applied to pump chamber 5037 via pneumatic air pressure signal port 5768. Diaphragm 5763 is displaced and drawn upwards into air-side recess 5030 of the micropump, which in turn draws a liquid (e.g., extractant, cleaning/flushing water, calibration standard liquid, etc.) into and fills pump chamber 5037 from fluid inlet port 5766. The inlet port is fluidly coupled to a suction/intake side microchannel 4012 in the substrate. Diaphragm 5763 deforms into an arcuately curved profile and engages dome-shaped wall 5034 in the air-side recess and anti-stall grooves 5769 therein.

FIG. 40 shows micropump 5015 during the subsequent discharge or pumping stroke. Pneumatic (air) pressure is applied to pump chamber 5037 through the pneumatic air pressure signal port 5768. This flattens and forces diaphragm 5763 downwards into contact and engagement with surface 5033 of the liquid-side recess 5031 and anti-stall grooves 5769 therein. The liquid is forced outwards from pump chamber 5037 under pressure through fluid outlet port 5767 and enters a discharge side microchannel 4018 for further processing in microfluidic manifold substrate 5000. This completes one full pumping cycle, which can be repeated each time the slurry or another liquid (e.g., extractant, cleaning/flushing water, calibration standard liquid, etc.) is pumped.

According to another aspect of the microfluidic manifold processing substrate 5000, the arrangement of microfluidic devices (e.g., micropumps 5015, microvalves 4018, etc.) and microchannels 4012 are configured to create a constant downward slurry flow path through the substrate from the initial slurry inlet to the substrate via microvalve 4018*b* to the final slurry outlet via microvalve 4018*e* (see, e.g. FIG. 30). In general, due to gravity, particulates or solids in the slurry are of higher density (weight) than the water carrier fluid. Due to this, the particulates have a tendency to settle out of suspension in the mixture in all fluid chambers and passageways they encounter while flowing through the microfluidic devices and microchannels. Designing a slurry manifold where slurry flows in a "generally" downward direction assisted by gravity continually promotes good cleaning of the flow passages to deter and minimize leftover particulate/sediment deposits. Such an arrangement is shown for example in FIGS. 30-31. The term "generally" is intended to connote that there may be some portions of the slurry flow passage where a slight deviation from vertical may occur. However, the slurry will still flow assisted by gravity in a generally downward direction from the slurry inlet port to the slurry outlet port to prevent any significant accumulation of particulates within the flow passage.

Referring to FIGS. 30-31, microfluidic manifold processing substrate 5000 is preferably vertically oriented in use as shown to form the continuously downward slurry flow path through the substrate. The slurry flow path is shown in emboldened dashed lines. Slurry enters microvalve 4018*b* and flows downwards into the inlet port 5766 of first micropump 5015*a* and out from outlet port 5767 to intermediate microvalve 4018*f* to continue to second and third micropumps 5015*b*, 5015*c*. Extractant may then be drawn into the first micropump via extractant valve 4018*a* in a similar manner to mix with the slurry for forming the slurry extractant mixture. Flushing water microvalve 4018*c* and calibration standard liquid microvalve 4018*d* are also located upstream of the first micropump 5015*a* similarly to the slurry and extractant microvalves 4018*b*, 4018*a*. Water is used between slurry processing runs to clean and flush out the system. The calibration standard liquid is used to perform system calibration runs of the system for test extraction of analytes to ensure accuracy.

According to another aspect, the microvalves 4018 of the microfluidic manifold in the form of processing substrate 5000 are specially configured to form a positive seal between the inlet and outlet sides of the valves. This prevents flow leaking through the microvalves when in the closed position. Each microvalve is formed between liquid layer 5003 and air layer 5004 of the manifold. Microvalve 4018 may have a circular configuration comprising an air-side valve chamber 5058 recessed into air layer 5004, liquid-side valve chamber 5060 recessed therebelow into liquid layer 5003, and a resiliently deformable diaphragm 5763 separating the air-side and liquid-side valve chambers. In one embodiment, air-side valve chamber 5058 may be dome shaped forming a concavity defined by an arcuately curved wall 5058*a* and liquid-side valve chamber 5060 may, comprise a flat base wall 5060*a*. Liquid-side valve chamber 5060 comprises an inlet side 5061 including recessed inlet side sub-chamber 5050 having a flat bottom wall penetrated by an inlet port 5053 for introducing a liquid into the microvalve from the microchannel network. Liquid-side valve chamber 5060 further comprises an outlet side 5062 including recessed outlet side sub-chamber 5051 having a flat bottom wall penetrated by an outlet port 5052 for discharging the liquid back into the microchannel network. Air-side valve chamber 5080 includes a pneumatic air pressure signal port 5057 for actuating the valve. The microvalve is changeable between open and closed positions to allow or shutoff/block liquid flow through the valve (e.g., slurry, extractant, cleaning water, calibration standard liquid, etc.), respectively. Pneumatically operated microvalve 4018 may operate in the same manner as micropump 4018 previously described herein (e.g., vacuum applied to open valve, pressure applied to close the valve). In other embodiments, the microvalve may alternatively open under a pressurized entry of liquid into the valve via inlet port 5053 and close via application of pressure via pneumatic air pressure signal port 5768 to air-side valve chamber 5060.

Each microvalve 4018 may further include a sealing bar 5054 fluidly separating and isolating the inlet and outlet sides 5061, 5062 of the valve when the diaphragm 5763 engages the sealing bar when the microvalve is in a closed position. Sealing bar advantageously creates a positive leak-resistant seal between the liquid inlet and outlet sides of the microvalve to promote positive shutoff in the closed position. Liquid is transferrable from the inlet side to the outlet side of the liquid-side valve chamber when the microvalve is in an open position in which the diaphragm disengages the sealing bar. Slight displacement allows flow to be establish through the microvalve. Liquid-side valve chamber 5060 further comprises an annular protruding sealing ring 5055 circumferentially extending around the inlet and outlet sides of the liquid-side valve chamber. The sealing bar may be a linear structure which extends inside and is connected to the sealing ring between diametrically opposite points of the sealing ring as shown. In one embodiment, sealing ring and sealing bar have the same height such that the diaphragm 5763 engages the top surfaces of the sealing ring and bar when the valve is in the closed position. The sealing ring 5055 is surrounded by an annular diaphragm retention pocket 5056 recessed into the liquid layer 5003 which comprise an integral part of the microvalve 4018.

EXAMPLES

The following are nonlimiting examples.

Example 1—a microfluidic manifold for processing an agricultural slurry comprising: a micropump formed between a liquid layer and an air layer of the manifold, the micropump comprising a pump chamber collectively formed by an air-side recess and a liquid-side recess, and a resiliently deformable diaphragm separating the air-side and liquid-side recesses; the micropump further comprising a perimeter flow groove extending circumferentially around peripheral portions of the pump chamber.

Example 2—the microfluidic manifold according to Example 1, wherein the perimeter flow groove extends circumferentially around the liquid-side recess and is recessed into a top surface of the liquid layer.

Example 3—the microfluidic manifold according to Examples 1 or 2, wherein the diaphragm is formed of fluorosilicone.

Example 4—the microfluidic manifold according to any one of Examples 1-3, wherein the perimeter flow groove intersects and is fluidly coupled to a fluid inlet port and fluid outlet port of the micropump.

Example 5—the microfluidic manifold according to any one of Examples 1-4, wherein the perimeter flow groove is spaced inwards from a circumferentially-extending peripheral sidewall of the liquid-side recess.

Example 6—the microfluidic manifold according Example 5, further comprising a protruding diaphragm seal ring disposed adjacent to the perimeter flow groove.

Example 7—the microfluidic manifold according to Example 6, wherein the seal ring extends circumferentially around and outboard of the flow groove.

Example 8—the microfluidic manifold according to Example 7, wherein the seal is configured to prevent ingress of the diaphragm into the perimeter flow groove when the liquid layer is bonded to the air layer.

Example 9—the microfluidic manifold according to Example 8, wherein the seal ring has a wider base than a terminal top end portion.

Example 10—the seal ring according to Example 9, wherein the seal ring comprises one or two obliquely angled surfaces at the top end portion forming a cross-sectional profile which is narrower than the base.

Example 11—the microfluidic manifold according to Example 9, wherein the seal ring has a trapezoidal or partial trapezoidal cross-sectional shape.

Example 12—the microfluidic manifold according to any one of Examples 6-11, wherein the seal ring is disposed between the peripheral sidewall of the liquid-side recess and the perimeter flow groove.

Example 13—the microfluidic manifold according to Example 12, further comprising a diaphragm seating pocket formed between the seal ring and the peripheral sidewall of the liquid-side pump chamber.

Example 14—the microfluidic manifold according to any one of Examples 1-13, wherein the liquid-side recess comprises a plurality of anti-stall grooves recessed into the liquid layer.

Example 15—the microfluidic manifold according to Example 14, wherein the anti-stall grooves are arranged in an orthogonally intersecting grid array.

Example 16—the microfluidic manifold according to Examples 14 or 15, wherein the anti-stall grooves intersect the perimeter flow groove.

Example 17—the microfluidic manifold according to any one of Examples 14-16, wherein the air-side recess comprises a plurality of intersecting anti-stall grooves recessed into the air layer.

Example 18—the microfluidic manifold according to Example 1, wherein the air-side recess has a domed shape wall and the liquid-side recess has a flat shaped wall.

Example 19—the microfluidic manifold according to any one of Examples 1-18, wherein the microfluidic manifold comprises a block shaped substrate, the liquid and air layers being formed internally within the substrate.

Example 20—a microfluidic manifold for processing an agricultural slurry comprising: a microvalve formed between a liquid layer and an air layer of the manifold, the microvalve comprising an air-side valve chamber, a liquid-side valve chamber, and a resiliently deformable diaphragm separating the air-side and liquid-side valve chambers; the liquid-side valve chamber comprising an inlet side comprising an inlet port for introducing a liquid into the microvalve, and an outlet side comprising an outlet port for discharging the liquid; the microvalve changeable between open and closed positions; and a sealing bar fluidly separating and isolating the inlet and outlet sides when the diaphragm engages the sealing bar when the microvalve is in a closed position.

Example 21—the microfluidic manifold according to Example 20, wherein the liquid is transferrable from the inlet side to the outlet side of the liquid-side valve chamber when the microvalve is in an open position in which the diaphragm disengages the sealing bar.

Example 22—the microfluidic manifold according to Examples 20 or 21, wherein the liquid-side valve chamber further comprises a protruding sealing ring circumferentially extending around the inlet and outlet sides of the liquid-side valve chamber; the sealing bar extending inside the sealing ring between diametrically opposite points of the sealing ring.

Example 23—the microfluidic manifold according to any one of Examples 20-22, wherein the sealing ring and sealing bar have the same height.

Example 24—the microfluidic manifold according to any one of Examples 20-23, wherein the air-side valve chamber has a dome shaped wall and the liquid-side valve chamber has a flat shaped wall.

Example 25—the microfluidic manifold according to any one of Examples 20-24, wherein the liquid is a slurry containing particulates.

Example 26—a microfluidic manifold for processing an agricultural slurry comprising: a substrate; a slurry inlet port formed in the substrate; a slurry outlet port formed in the substrate; and a slurry flow path formed internally within the substrate and fluidly coupling the slurry inlet port to the slurry outlet port; wherein the slurry flow path is configured such that the slurry flows assisted by gravity in a generally downward direction from the slurry inlet port to the slurry outlet port.

Example 27—the microfluidic manifold according to Example 26, wherein the slurry flow path is defined by a plurality of microchannels formed in the substrate.

Example 28—the microfluidic manifold according to Example 27, further comprising a plurality of microfluidic devices fluidly coupled together by the microchannels between the slurry inlet and outlet ports.

Example 29—the microfluidic manifold according to Example 28, wherein the microfluidic devices include at least one micropump and at least one microvalve.

Example 30—the microfluidic manifold according to Example 29, wherein the at least one micropump includes an inlet port and an outlet port, wherein the inlet port is fluidly coupled to a plurality of upstream microvalves by the microchannels.

Example 31—the microfluidic manifold according to any one of Examples 27-30, wherein the substrate has a rectangular cuboid form including opposing first and second major sides which are vertically oriented to produce the downward direction of the slurry in the flow path.

Example 32—the microfluidic manifold according to any one of Examples 27-31, wherein the slurry outlet port is lower in the substrate than the slurry inlet port.

Example 33—the microfluidic manifold according to any one of Examples 27-32, wherein the substrate is comprised of a plurality of polymeric layers bonded together.

Example 34—the microfluidic manifold according to Example 33, wherein the microchannels are formed between adjacent internal layers of the substrate.

While the foregoing description and drawings represent some example systems, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention.

What is claimed is:

1. A microfluidic manifold for processing an agricultural slurry comprising:
   a substrate comprised of a plurality of polymeric planar layers bonded together and having a vertical orientation;
   a slurry inlet port formed in the substrate;
   a slurry outlet port formed in the substrate; and
   a slurry flow path formed internally within the substrate and fluidly coupling the slurry inlet port to the slurry outlet port;
   wherein the slurry flow path is configured such that the slurry always flows assisted by gravity in a constant downward sloping direction in all portions of the slurry flow path from the slurry inlet port to the slurry outlet port.

2. The microfluidic manifold according to claim 1, wherein the slurry flow path is defined by a plurality of microchannels formed in the substrate such that there are no sections of the microchannels that form the slurry flow path which have a horizontal orientation to prevent solids in the slurry from settling out of suspension.

3. The microfluidic manifold according to claim 2, further comprising a plurality of microfluidic devices fluidly coupled together by the microchannels between the slurry inlet and outlet ports.

4. The microfluidic manifold according to claim 3, wherein the microfluidic devices include at least one micropump and at least one microvalve.

5. The microfluidic manifold according to claim 4, wherein the at least one micropump includes an inlet port and an outlet port, wherein the inlet port is fluidly coupled to a plurality of upstream microvalves by the microchannels.

6. The microfluidic nanifold according to claim 5, wherein the upstream microvalves include an extractant microvalve fluidly coupled to an extractant source, a flushing water microvalve fluidly coupled to a water source, a slurry microvalve fluidly coupled to the slurry inlet port, and a calibration standard liquid microvalve all of which are fluidly coupled to the at least one micropump by a single shared branched microchannel section.

7. The microfluidic manifold according to claim 6, wherein micropumps are vertically aligned in the substrate and fluidly isolatable from each other via a microvalve arranged in the slurry flow path between the micropumps.

8. The microfluidic manifold according to claim 5, wherein in the at least one micropump is vertically oriented, the inlet port of the at least one micropump being located at a top thereof and the outlet port of the micropump being located at a bottom thereof such that the slurry flows in a vertical downward direction through the at least one micropump.

9. The microfluidic manifold according to claim 2, wherein the substrate has a rectangular cuboid form including opposing first and second major sides which are vertically oriented to produce the downward direction of the slurry in the flow path.

10. The microfluidic manifold according to claim 2, wherein the slurry outlet port is lower in the substrate than the slurry inlet port.

11. The microfluidic manifold according to claim 1, wherein the microchannels are formed between adjacent internal layers of the substrate.

12. The microfluidic manifold according to claim 11 wherein the microchannels are formed in a fluid distribution layer, the at least one micropump and the at least one microvalve are formed by concave recesses in a liquid layer, and an air layer is interspersed between the fluid distribution and liquid layers to place the at least one micropump and the at least one microvalve in fluid communication with a source of pressurized air which operates the at least one micropump and the at least one microvalve.

13. The microfluidic manifold according to claim 12, further comprising a first outer layer disposed on the fluid distribution layer which defines a planar first major surface and a second outer layer disposed on the liquid layer which defines an opposite planar second major surface.

14. The microfluidic manifold according to claim 13, wherein the first major surface comprises a plurality of external air valves configured for coupling to air tubing, a first air valve being fluidly coupled to the at least one micropump and a second air valve being fluidly coupled to the at least one microvalve through the fluid distribution and air layers.

15. The microfluidic manifold according to claim 13, wherein the first major surface further comprises a plurality of liquid fittings each fluidly coupled to a respective microvalve of a plurality of microvalves disposed in the liquid layer.

16. The microfluidic manifold according to claim 15, wherein one of the liquid fittings on the first major surface forms part of the slurry inlet port and another of the liquid fittings on the first major surface forms part of the slurry outlet port.

17. The microfluidic manifold according to claim 12, wherein the at least one micropump comprises a resiliently deformable diaphragm trapped between the fluid distribution layer and the air layer which seals a first one of the recesses in the liquid layer that defines the at least one micropump, and wherein the at least one microvalve comprises a resiliently deformable diaphragm trapped between the fluid distribution layer and the air layer which seals a second one of the recesses in the liquid layer that defines the at least one microvalve.

18. The microfluidic manifold according to claim 17, further comprising a plurality of micropumps arranged in and forming part of the slurry flow path, the micropumps each being oriented so that the slurry flows in the vertical downward direction through each of the micropumps.

19. The microfluidic manifold according to claim 1, wherein the substrate is vertically oriented.

* * * * *